US012582654B2

(12) United States Patent
Zhang et al.

(10) Patent No.: US 12,582,654 B2
(45) Date of Patent: Mar. 24, 2026

(54) CYANO-SUBSTITUTED PYRIDINE AND CYANO-SUBSTITUTED PYRIMIDINE COMPOUND AND PREPARATION METHOD THEREFOR AND APPLICATION THEREOF

(71) Applicant: BEIJING SCITECH-MQ PHARMACEUTICALS LIMITED, Beijing (CN)

(72) Inventors: Qiang Zhang, Beijing (CN); Leifu Yang, Beijing (CN); Nanqiao Zheng, Beijing (CN); Shannan Yu, Beijing (CN); Yueming Sun, Beijing (CN); Zhenke Guo, Beijing (CN)

(73) Assignee: BEIJING SCITECH-MQ PHARMACEUTICALS LIMITED, Beijing (CN)

( * ) Notice: Subject to any disclaimer, the term of this patent is extended or adjusted under 35 U.S.C. 154(b) by 869 days.

(21) Appl. No.: 17/788,663

(22) PCT Filed: Dec. 21, 2020

(86) PCT No.: PCT/CN2020/137938

§ 371 (c)(1),
(2) Date: Jun. 23, 2022

(87) PCT Pub. No.: WO2021/129561

PCT Pub. Date: Jul. 1, 2021

(65) Prior Publication Data

US 2023/0125046 A1 Apr. 20, 2023

(30) Foreign Application Priority Data

Dec. 23, 2019 (CN) ......................... 201911337644.9

(51) Int. Cl.

| | |
|---|---|
| *A61K 31/506* | (2006.01) |
| *A61K 31/4545* | (2006.01) |
| *A61K 31/496* | (2006.01) |
| *A61K 31/5377* | (2006.01) |
| *A61K 31/541* | (2006.01) |
| *C07D 213/84* | (2006.01) |
| *C07D 239/48* | (2006.01) |
| *C07D 401/12* | (2006.01) |
| *C07D 401/14* | (2006.01) |
| *C07D 405/14* | (2006.01) |
| *C07D 417/14* | (2006.01) |

(52) U.S. Cl.

CPC ........ *A61K 31/506* (2013.01); *A61K 31/4545* (2013.01); *A61K 31/496* (2013.01); *A61K 31/5377* (2013.01); *A61K 31/541* (2013.01); *C07D 213/84* (2013.01); *C07D 239/48* (2013.01); *C07D 401/12* (2013.01); *C07D 401/14* (2013.01); *C07D 405/14* (2013.01); *C07D 417/14* (2013.01)

(58) Field of Classification Search

CPC .............. A61K 31/506; A61K 31/4545; A61K 31/496; A61K 31/5377; A61K 31/541; C07D 213/84; C07D 239/48; C07D 401/12; C07D 401/14; C07D 405/14; C07D 417/14

See application file for complete search history.

(56) References Cited

FOREIGN PATENT DOCUMENTS

| | | | | | |
|---|---|---|---|---|---|
| CN | 104540809 | A | | 4/2015 | |
| CN | 106187915 | A | | 12/2016 | |
| CN | 110467638 | A | | 11/2019 | |
| EP | 3398939 | A1 | * | 11/2018 | ........... C07D 403/12 |
| WO | WO-2015057963 | A1 | * | 4/2015 | .............. A61P 35/00 |
| WO | 2016/164703 | A1 | | 10/2016 | |
| WO | 2018/072707 | A1 | | 4/2018 | |
| WO | 2019/242689 | A1 | | 12/2019 | |

OTHER PUBLICATIONS

Organic chemistry / Francis A. Carey.—4th ed. 2000. (Year: 2000).*
By Stella et al., Prodrugs: Challenges and Rewards, Part 1, 2007. (Year: 2007).*
International Search Report and Written Opinion for Application No. PCT/CN2020/137938, dated Mar. 22, 2021, 26 pages.
International Preliminary Report on Patentability for Application No. PCT/CN2020/137938, dated Jul. 7, 2022, 19 pages.

* cited by examiner

*Primary Examiner* — Clinton A Brooks
*Assistant Examiner* — Izabela Schmidt
(74) *Attorney, Agent, or Firm* — McCarter & English, LLP; Xin Zhang

(57) ABSTRACT

A cyano-substituted pyridine and cyano-substituted pyrimidine compound and a preparation method therefor and an application thereof, which specifically relate to a compound represented by formula (I) and an isomer, a hydrate, a solvate, a pharmaceutically acceptable salt, and a prodrug thereof, and a preparation method therefor and an application thereof in the preparation of a drug as a kinase inhibitor. The compound has good inhibitory activity against kinases such as FGFR4 and mutant FGFR4$^{V550L}$.

(I)

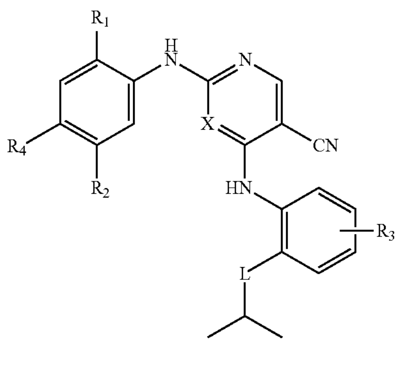

20 Claims, No Drawings

CYANO-SUBSTITUTED PYRIDINE AND CYANO-SUBSTITUTED PYRIMIDINE COMPOUND AND PREPARATION METHOD THEREFOR AND APPLICATION THEREOF

CROSS REFERENCE TO RELATED APPLICATIONS

The present application is a national application of PCT/CN2020/137938 filed on Dec. 21, 2020, which claims the priority of the Chinese Patent Application No. 201911337644.9 filed on Dec. 23, 2019. The Chinese Patent Application No. 201911337644.9 is incorporated herein by reference as part of the disclosure of the present application.

FIELD OF THE INVENTION

The present disclosure relates to cyano-substituted pyridine and cyano-substituted pyrimidine compounds, pharmaceutically acceptable salts, isomers, hydrates, solvates, or prodrugs thereof, and preparation methods and uses thereof.

BACKGROUND OF THE INVENTION

The activating mutation or amplification of FGFRs in cells can lead to overactivation of the FGF-FGFR signaling pathway, enabling cells to acquire oncogenic properties such as hyperproliferation, escape from apoptosis, and easy migration. Therefore, FGFRs can be used as targets for direct or indirect tumor therapy. FGFR is mainly divided into 4 subtypes, namely FGFR1, FGFR2, FGFR3 and FGFR4. Each subtype has the general structural features of receptor tyrosine kinases: an extracellular domain for ligand binding, a transmembrane domain, and an intracellular domain for receptor phosphorylation. When a ligand specifically binds to a receptor, FGFR is induced to autophosphorylate and then dimerize, making its domain transform from an inactive state to an active state. Further, activated FGFR and intracellular kinases are close to each other and phosphorylate each other, thereby activating a series of downstream related signaling pathways, and ultimately stimulating cell proliferation and differentiation, and inhibiting cell apoptosis. Since FGFR plays a critical role in tumorigenesis and development of tumors, targeted therapy for FGFR has become a hot field in clinical research. Existing drugs targeting FGFR can be divided into two categories according to their sources: the first category is chemical small molecule inhibitors, which can competitively or non-competitively bind to the intracellular kinase domain of FGFR and inhibit abilities of autophosphorylation, dimerization, and catalyzing downstream protein phosphorylation of FGFR, thereby inhibiting the FGFR signaling pathway. The second category is a biological monoclonal antibody or a polypeptide inhibitor, which can bind to the extracellular region of FGFR and prevent the binding of FGF to FGFR, thereby inhibiting the activation of FGFR and blocking FGFR signal transduction (Seiji Mori, Yoshikazu Takada, Med. Sci. 2013, 1, 20-36).

Small molecule tyrosine kinase inhibitors block cell proliferation signaling by blocking the binding activity of intracellular kinases to ATP. Due to similar structures of kinase domains of FGFR1, FGFR2, and FGFR3, the effects of inhibitors against these three kinases developed at this stage are not much different. However, FGFR4 kinase domain is somewhat different from FGFR1-3 kinase domains, so that many inhibitors that can effectively inhibit FGFR1-3 do not work well against FGFR4. For example, AZD-4547, Infigratinib, CH-5183284, E-7090, BAY-1163877, INCB-54828, etc., which are in clinical trials in recent years, target FGFR1/2/3 targets, while FGF-401 and BLU-554 target FGFR4 target. Small molecule FGFR inhibitors can be divided into: 1) ATP-competitive reversible inhibitors, 2) covalently bound irreversible inhibitors, 3) ATP-non-competitive inhibitors (Wu Daichao et al., Cancer Prevention and Treatment Research 2017, 44(1): 61-65).

AZD-4547 is a small molecule selective ATP-competitive reversible inhibitor that acts on FGFR in a linear configuration. It can be seen from a co-crystal structure of a protein-ligand complex of FGFR1/AZD-4547 that: the 3-aminopyrazole parent ring of AZD-4547 has three hydrogen bond interactions with Ala564 and Glu562 in the hinge region; the 3,5-dimethoxyphenyl side chain extends into the inward hydrophobic pocket of the hinge region; and the para-chiral piperazine substituted benzoyl group has a hydrophilic or hydrophobic interaction with the near-solvent end domain extending out of the hinge region. Under these actions, the entire molecule is inserted into the ATP-binding region of FGFR1 in a linear configuration, and binds tightly to the FGFR1 protein. Compounds with linear-like actions also include BGJ-398, CH-5183284 and ASP-5878.

JNJ-42756493 is a small molecule selective ATP-competitive reversible inhibitor that acts on FGFR in a T-shaped configuration. It can be seen from the co-crystal structure of JNJ-42756493/FGFR1 that: the N at 1-position of the quinoxaline parent ring of JNJ-42756493 forms a hydrogen bond to Ala564 of the hinge region; the 3,5-dimethoxyphenyl side chain occupies the inward hydrophobic pocket of the hinge region, the isopropylamine side chain has a hydrophilic or hydrophobic interaction with the downward pocket of the hinge region; and the NH of the isopropylamine also has a hydrogen bond interaction with Asp641.

The hinge region of the ATP-binding site of the protein has a cysteine residue, while differently, FGFR1, 2, and 3 have a tyrosine residue at this site. Starting from this small difference in structure, PD173074, a selective FGFR inhibitor with nanomolar inhibitory activity, was found. On this basis, 2-aminoquinazoline derivatives that can specifically inhibit FGFR4 were found. Compound BLU-9931 was obtained when one acrylamide substituent was introduced into the beta position of the amino group. It was found that the acrylamide of BLU-9931 can irreversibly covalently bind to Cys552 of FGFR4. $IC_{50}$ for FGFR4 inhibitory activity of BLU-9931 is 3 nmol/L, and the selectivity is 297, 184 and 50 times higher than those of FGFR1/2/3, respectively. Through further structural optimization of BLU-9931, BLU-554 was found to be a selective covalent irreversible inhibitor of FGFR4, which was approved by the FDA for clinical trials in the treatment of hepatocellular carcinoma in September 2015. TAS-120 and PRN-1371 are also covalent inhibitors of FGFR, with nanomolar levels of enzymatic inhibitory activity against each subtype of FGFR.

ARQ-087 is a non-ATP-competitive inhibitor with more than 8-fold selectivity for FGFR1, 2 and 3 over FGFR4.

Alterations in FGFR have been associated with a variety of human cancers, including myeloma, breast, gastric, colon, bladder, pancreatic, and hepatocellular carcinoma. Small molecule inhibitors of FGFR can be divided into pan-FGFR and FGFR4-specific small molecule inhibitors. Due to similar structures of kinase domains of FGFR1, FGFR2, and FGFR3, the effects of inhibitors against these three kinases developed at this stage are not much different. FGFR4 has been reported to play an important role in liver cancer in particular (PLoS One, 2012, Vol. 7, 36713). The FGFR4 kinase domain is somewhat different from the FGFR1-3 kinase domains, so that many inhibitors that can effectively inhibit FGFR1-3 do not work well against FGFR4.

In order to improve the selectivity of small-molecule inhibitors to the FGFR4 kinase domain and reduce adverse reactions, H3 Biopharmaceutical Co., Ltd. disclosed in patents (WO 2015057938 A1 (published date 20150423) Pyrimidines as FGFR4 inhibitors and their preparation and WO 2015057963 A1 (published date 20150423)N-Aryl-heteroarylamines as FGFR4 inhibitors and their preparation) FGFR4-specific inhibitors, of which H3B-6527 that has entered the FDA Phase I clinical stage and has obtained orphan drug qualification has a structure of:

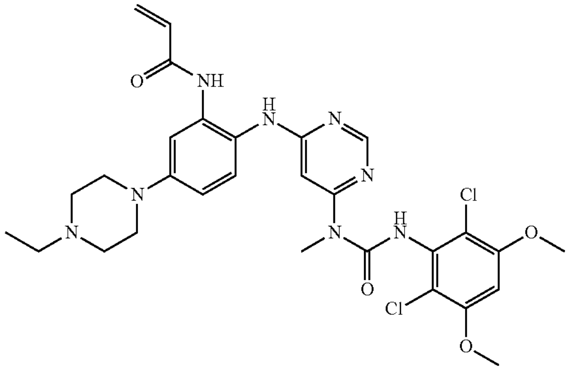 [SMILES: C=CC(=O)Nc1cc(N2CCN(CC)CC2)ccc1Nc1cc(N(C)C(=O)Nc2c(Cl)c(OC)cc(OC)c2Cl)ncn1]

H3B6527 has strong antitumor activity against FGF19 gene-amplified cells without bile acid-related adverse effects in mouse and monkey animal models. However, a single administration of H3B-6527 only controls cancer cell growth but cannot eliminate cancer cells (Cancer Res; 77(24) Dec. 15, 2017). The drug resistance resulting from the key site V550L or V550 mutation reduces or invalidates the efficacy of H3B-6527. How to break through the limitations of these gene mutations that lead to drug resistance will become the focus of the next phase of FGFR4 inhibitor research.

Inhibitors targeting FGFR4 target have many advantages, especially their excellent selectivity and resistance to mutagenesis. There are very few drugs currently on the market, and therefore, the discovery of such small-molecule inhibitors targeting FGFR4 will have better therapeutic effects and application prospects. The development of new, highly selective and potent inhibitors of FGFR4 has become an urgent clinical problem.

SUMMARY OF THE INVENTION

The present disclosure provides a compound represented by formula (I), or a pharmaceutically acceptable salt, an isomer, a hydrate, a solvate, or a prodrug thereof, which can be used for the treatment or prevention of diseases caused by tyrosine kinase FGFR4, including some variants of tyrosine kinase FGFR4 receptor, Formula (I)

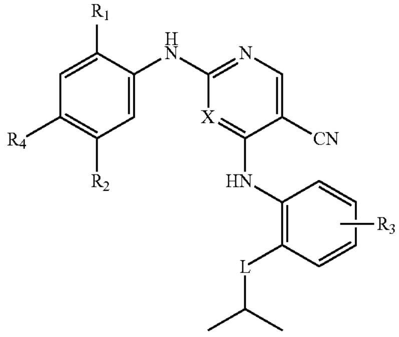

In formula (I),

X is N or CH;

L is —O—, —S—,

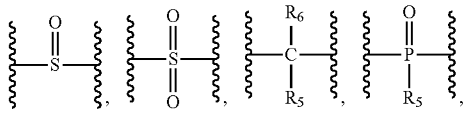

or —$NR_5$—, wherein $R_5$ and $R_6$ are each independently hydrogen, methyl, ethyl, propyl or isopropyl;

$R^1$ is

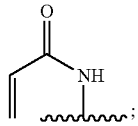 [SMILES: *NC(=O)C=C]

;

$R_2$ is hydrogen, halogen, $C_1$-$C_3$ alkoxy, or $C_1$-$C_3$ alkyl;

$R_3$ is selected from hydrogen, halogen, hydroxyl, amino, cyano, carboxyl, $C_1$-$C_6$ alkyl, $C_1$-$C_6$ haloalkyl, $C_1$-$C_3$ haloalkoxy, $C_3$-$C_6$ cycloalkyl, $C_2$-$C_3$ alkynyl, $C_2$-$C_3$ alkenyl, $C_1$-$C_3$ alkoxy, $C_1$-$C_3$ alkylthio, mono- or di-$C_1$-$C_3$ alkylamino, $C_3$-$C_4$ cycloalkyloxy, $C_3$-$C_4$ cycloalkyl-substituted $C_1$-$C_3$ alkyl, cyano-substituted $C_1$-$C_3$ alkyl, carbamoyl-substituted $C_1$-$C_3$ alkyl, or the following groups:

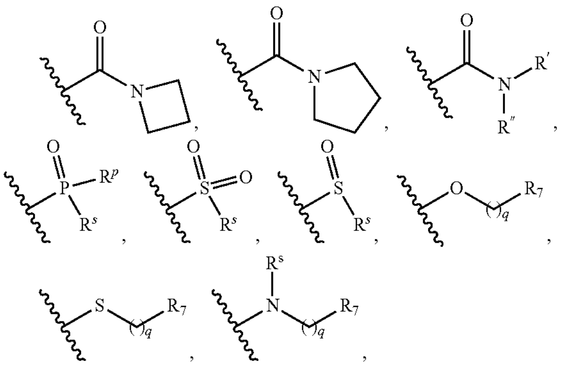

q is an integer of 1-3, $R^s$ is selected from —H, or $C_1$-$C_3$ alkyl, and $R^p$ is selected from —H, or $C_1$-$C_3$ alkyl, R' and R" are each independently —H, $C_1$-$C_3$ alkyl, or $C_3$-$C_4$ cycloalkyl, $R_7$ is selected from —H, halogen, hydroxyl, cyano, amino, carboxyl, $C_1$-$C_3$ alkyl, $C_3$-$C_4$ cycloalkyl, $C_1$-$C_3$ alkoxy, or mono- or di-$C_1$-$C_3$ alkyl-substituted amino;

$R_4$ is -$T_1$-$R_8$ or -$T_2$-$R_9$, $T_1$ is:

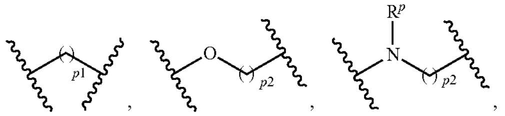

$T_2$ is:

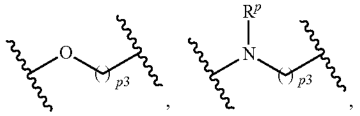

p1 is an integer of 0-4, p2 is an integer of 2-4, and p3 is an integer of 0-1, $R^p$ is —H or $C_1$-$C_3$ alkyl, $R_8$ is selected from —H, halogen, hydroxyl, amino, cyano, $C_1$-$C_6$ alkyl, $C_1$-$C_6$ haloalkyl, $C_1$-$C_3$ haloalkoxy, $C_3$-$C_6$ cycloalkyl, $C_1$-$C_3$ alkoxy, $C_1$-$C_3$ alkylthio, mono- or di-$C_1$-$C_3$ alkylamino, or a 4- to 6-membered heteroalicyclic group, wherein the 4- to 6-membered heteroalicyclic group is unsubstituted or substituted with 1-2 identical or different substituents selected from hydroxyl, $C_1$-$C_6$ alkyl, $C_1$-$C_3$ alkoxy, formyl, acetyl, propionyl, isopropionyl, hydroxyl-substituted $C_1$-$C_3$ alkyl, carboxy-substituted $C_1$-$C_3$ alkyl, oxo, $C_1$-$C_3$ alkyl-substituted or unsubstituted 4- to 6-membered heteroalicyclic group, or —$NR^{10}R^{11}$, $R^{10}$ and $R^{11}$ are each independently selected from —H, $C_1$-$C_6$ alkyl, $C_3$-$C_4$ cycloalkyl, hydroxyl-substituted $C_2$-$C_6$ alkyl, cyano-substituted $C_1$-$C_2$ alkyl, $C_1$-$C_3$ alkoxy-substituted $C_1$-$C_3$alkyl, $C_1$-$C_3$ alkylthio-substituted $C_1$-$C_3$ alkyl, $C_1$-$C_3$ haloalkyl, methylsulfonyl-substituted $C_1$-$C_3$ alkyl, mono- or di-$C_1$-$C_3$ alkylamino-substituted $C_1$-$C_3$ alkyl, or $C_1$-$C_3$ alkyl-substituted or unsubstituted 4- to 6-membered heteroalicyclic group, or $R^{10}$ and $R^{11}$ together with the nitrogen atom to which they are attached form a 4- to 6-membered heteroalicyclic group, wherein the 4- to 6-membered heteroalicyclic group is unsubstituted or substituted with 1-2 identical or different substituents selected from —H, hydroxyl, oxo, halogen, $C_1$-$C_3$ alkoxy-substituted $C_1$-$C_3$ alkyl, $C_1$-$C_3$ alkylsulfonyl, cyano, amino, $C_1$-$C_3$ acyl, $C_1$-$C_3$ alkyl, mono- or di-$C_1$-$C_3$ alkylamino, hydroxyl-substituted $C_2$-$C_3$ alkyl, or $C_1$-$C_3$ alkoxy, the 4- to 6-membered heteroalicyclic group contains 1-2 heteroatoms selected from N, O or S;

$R^9$ is selected from —H, $C_1$-$C_6$ alkyl, $C_3$-$C_6$ cycloalkyl, or a 4- to 6-membered heteroalicyclic group, wherein the 4- to 6-membered heteroalicyclic group is unsubstituted or substituted with 1-2 identical or different substituents selected from hydroxyl, $C_1$-$C_3$ alkyl, $C_1$-$C_3$alkoxy, formyl, acetyl, propionyl, or isopropionyl, the 4- to 6-membered heteroalicyclic group in $R^9$ contains 1-2 heteroatoms selected from N, O or S;

and, when $R^1$ is

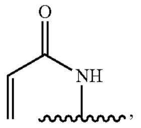

$R_4$ is 4-ethyl-piperazin-1-yl and L is —O— or

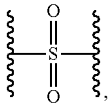

$R_2$ and $R_3$ are not both hydrogen.

In an alternative embodiment, $R_2$ is —H, —F, —Cl, methyl or methoxy.

In an alternative embodiment, $R_3$ is selected from —H, —F, —Cl, —Br, hydroxyl, carboxyl, cyano, methyl, ethyl, propyl, isopropyl, tert-butyl, methoxy, ethoxy, propoxy, isopropoxy, cyclopropyloxy, cyclobutyloxy, methylthio, ethylthio, propylthio, isopropylthio, fluoromethyl, difluoromethyl, trifluoromethyl, fluoromethoxy, difluoromethoxy, trifluoromethoxy, ethynyl, ethenyl, cyclopropyl, cyclobutyl, cyclopropylmethyl, cyclobutylmethyl, amino, methylamino, ethylamino, dimethylamino, diethylamino, N-methyl-N-ethylamino, or the following groups:

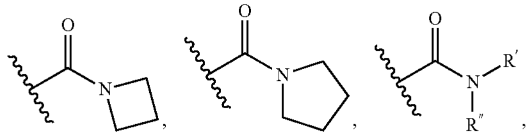

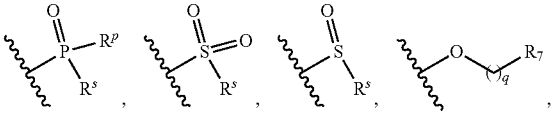

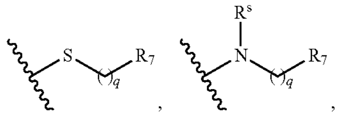

q is an integer of 2-3, $R^s$ is selected from —H, methyl, or ethyl, and $R^p$ is selected from —H, methyl, or ethyl, R' and R" are each independently selected from —H, methyl, ethyl, propyl, isopropyl, cyclopropyl, or cyclobutyl, $R_7$ is selected from —H, —F, hydroxyl, cyano, carboxyl, amino, methyl, ethyl, propyl, isopropyl, methoxy, ethoxy, propoxy, isopropoxy, methylamino, ethylamino, or dimethylamino.

In a further alternative embodiment, $R_3$ is selected from —H, —F, —Cl, hydroxyl, carboxyl, cyano, methyl, ethyl, propyl, isopropyl, tert-butyl, methoxy, ethoxy, propoxy, isopropoxy, cyclopropyloxy, cyclobutyloxy, methylthio, ethylthio, propylthio, isopropylthio, fluoromethyl, difluoromethyl, trifluoromethyl, cyclopropyl, cyclobutyl, cyclopropylmethyl, cyclobutylmethyl, amino, methylamino, ethylamino, dimethylamino, diethylamino, N-methyl-N-ethylamino, methoxyethoxy, ethoxyethoxy, carbamoyl ($NH_2CO$—), or methylsulfonyl.

In an alternative embodiment, $R^4$ is $-T_1-R_8$, $T_1$ is selected from:

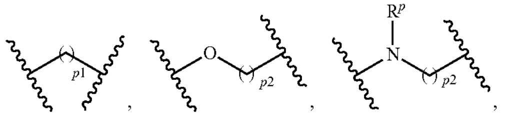

p1 is an integer of 0-3, and p2 is an integer of 2-3;

$R^p$ is selected from —H, methyl, or ethyl;

$R^8$ is selected from —H, —F, —Cl, hydroxyl, amino, cyano, fluoromethoxy, difluoromethoxy, trifluoromethoxy, methyl, ethyl, propyl, butyl, hexyl, isopropyl, fluoromethyl, difluoromethyl, trifluoromethyl, cyclopropyl, cyclobutyl, cyclopentyl, cyclohexyl, methoxy, ethoxy, propoxy, butoxy, isopropoxy, methylthio, ethylthio, propylthio, isopropylthio, methylamino, ethylamino, propylamino, dimethylamino, diethylamino, N-methyl-N-ethylamino or the following groups:

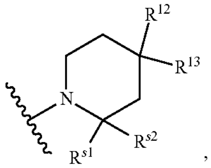 , 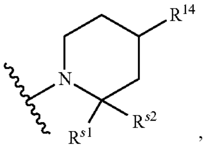 ,

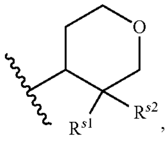 , 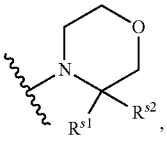 , 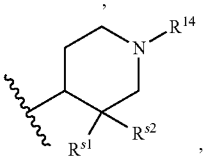 ,

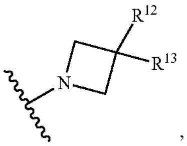 , 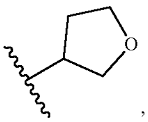 , 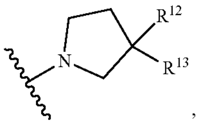 ,

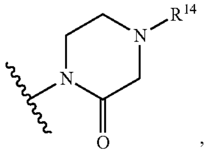 , $R^{12}$ is —H, —F, methyl, or ethyl, $R^{13}$ is —H, —F, hydroxyl, hydroxymethyl, cyano, methyl, ethyl, methoxy, or $-NR^{15}R^{16}$, $R^{14}$ is —H, —F, methyl, ethyl, propyl, isopropyl, or

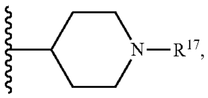

wherein $R^{17}$ is —H, —F, methyl, ethyl, propyl, or isopropyl, $R^{s1}$ and $R^{s2}$ are each independently selected from H, or methyl;

$R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetanyl, tetrahydrofuranyl, or tetrahydropyranyl, or $R^{15}$ and $R^{16}$ together with the nitrogen atom to which they are attached form a substituted or unsubstituted 4- to 6-membered heteroalicyclic group selected from the following groups:

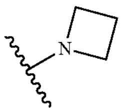 , 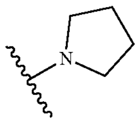 , 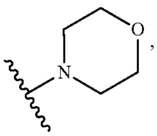 ,

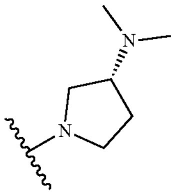 , 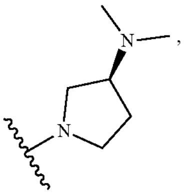 ,

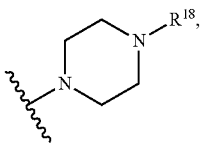 , 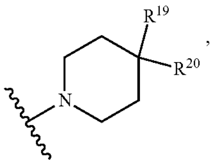 ,

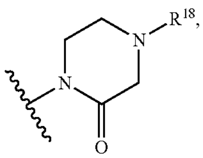 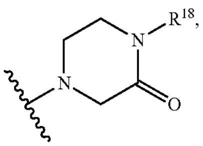

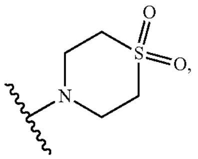

$R^{18}$ is selected from —H, methyl, ethyl, formyl, acetyl, hydroxyethyl, hydroxypropyl, fluoroethyl, fluoropropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, fluoro, formyl, acetyl, hydroxyethyl, hydroxypropyl, fluoroethyl, fluoropropyl, methoxyethyl, methoxypropyl, ethoxyethyl, ethoxypropyl, methylsulfonyl, ethylsulfonyl, amino, methylamino, dimethylamino, methoxy, or ethoxy.

In a further alternative embodiment, $R^4$ is $-T_1-R_8$, $T_1$ is selected from:

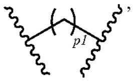

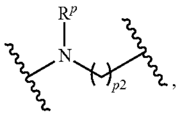

p1 is 0, and p2 is an integer of 2-3;

$R^p$ is selected from —H, methyl, or ethyl;

$R^8$ is selected from methylamino, ethylamino, propylamino, dimethylamino, diethylamino, N-methyl-N-ethylamino or the following groups:

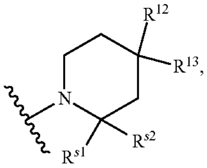

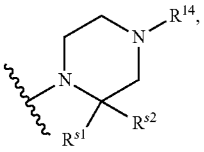

$R^{12}$ is —H, —F, methyl, or ethyl, $R^{13}$ is —H, or $-NR_{15}R^{16}$, $R^{14}$ is —H, methyl, ethyl, propyl, isopropyl, or

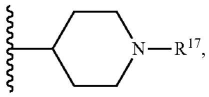

wherein $R^{17}$ is methyl, ethyl, propyl, or isopropyl, $R^{s1}$ and $R^{s2}$ are each independently selected from H, or methyl;

$R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetan-3-yl, tetrahydrofuran-3-yl, or tetrahydro-2H-pyran-4-yl, or $R^{15}$ and $R^{16}$ together with the nitrogen atom to which they are attached form a substituted or unsubstituted 4- to 6-membered heteroalicyclic group selected from the following groups:

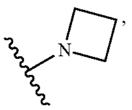

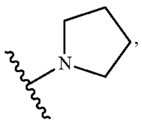

-continued

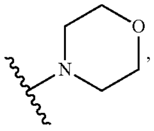

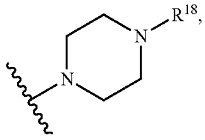

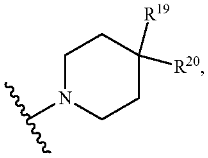

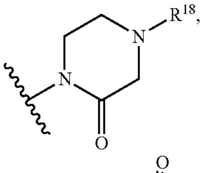

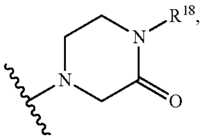

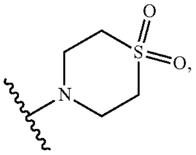

$R^{18}$ is selected from —H, methyl, ethyl, formyl, acetyl, hydroxyethyl, hydroxypropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, fluoro, hydroxyethyl, hydroxypropyl, fluoroethyl, fluoropropyl, methoxyethyl, methoxypropyl, ethoxyethyl, ethoxypropyl, methylsulfonyl, ethylsulfonyl, amino, methylamino, dimethylamino, methoxy, or ethoxy.

In a further alternative embodiment, $R^4$ is

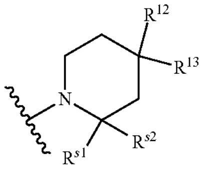

$R^{12}$ is —H, —F, methyl, or ethyl, $R^{13}$ is —H, or $-NR_{15}R^{16}$, $R^{s1}$ and $R^{s2}$ are H, $R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetan-3-yl, tetrahydrofuran-3-yl, or tetrahydro-2H-pyran-4-yl, or $R^{15}$ and $R^{16}$ together with the nitrogen atom to which they are attached form a substituted or unsubstituted 4- to 6-membered heteroalicyclic group selected from the following groups:

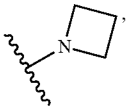
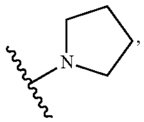
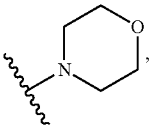
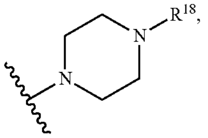
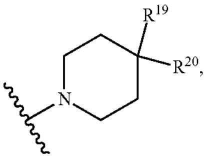
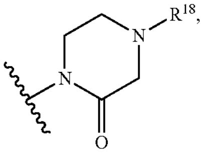
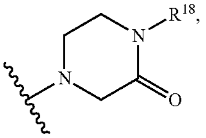
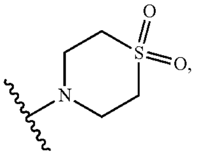

$R^{18}$ is selected from —H, methyl, ethyl, formyl, acetyl, hydroxyethyl, hydroxypropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, or fluoro.

According to one aspect of the present disclosure, there is provided a compound represented by formula (I), or an isomer, a hydrate, a solvate, a pharmaceutically acceptable salt and a prodrug thereof, Formula (I)

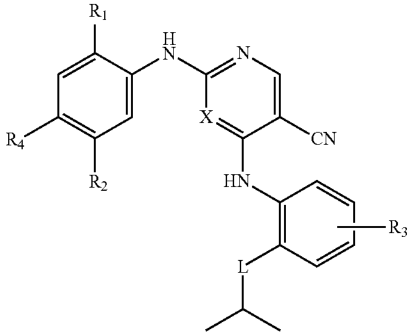

In formula (I),

X is N or CH;

L is —O—, —S—,

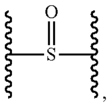
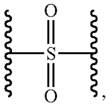

-continued

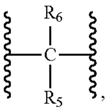
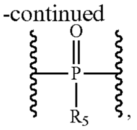

or —$NR_5$—, wherein $R_5$ and $R_6$ are each independently hydrogen, methyl, ethyl, propyl or isopropyl;

$R^1$ is

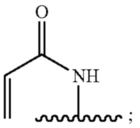

$R_2$ is —H, —F, —Cl, methyl, or methoxy;

$R_3$ is selected from —H, —F, —Cl, —Br, hydroxyl, carboxyl, cyano, methyl, ethyl, propyl, isopropyl, tert-butyl, methoxy, ethoxy, propoxy, isopropoxy, cyclopropyloxy, cyclobutyloxy, methylthio, ethylthio, propylthio, isopropylthio, fluoromethyl, difluoromethyl, trifluoromethyl, fluoromethoxy, difluoromethoxy, trifluoromethoxy, ethynyl, ethenyl, cyclopropyl, cyclobutyl, cyclopropylmethyl, cyclobutylmethyl, amino, methylamino, ethylamino, dimethylamino, diethylamino, N-methyl-N-ethylamino, or the following groups:

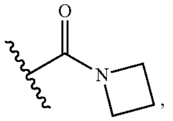
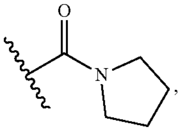
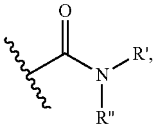
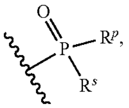
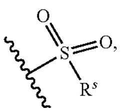
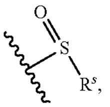
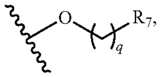
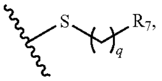
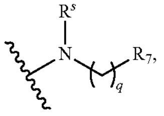

q is an integer of 2-3, $R^s$ is selected from —H, methyl, or ethyl, and $R^p$ is selected from —H, methyl, or ethyl, R' and R" are each independently selected from —H, methyl, ethyl, propyl, isopropyl, cyclopropyl, or cyclobutyl, $R_7$ is selected from —H, —F, hydroxyl, cyano, carboxyl, amino, methyl, ethyl, propyl, isopropyl, methoxy, ethoxy, propoxy, isopropoxy, methylamino, ethylamino, or dimethylamino;

$R^4$ is $-T_1-R_8$, $T_1$ is selected from:

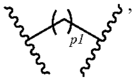

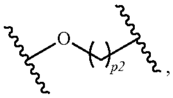

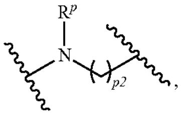

p1 is an integer of 0-3, and p2 is an integer of 2-3;

$R^p$ is selected from —H, methyl, or ethyl;

$R^8$ is selected from —H, —F, —Cl, hydroxyl, amino, cyano, fluoromethoxy, difluoromethoxy, trifluoromethoxy, methyl, ethyl, propyl, butyl, hexyl, isopropyl, fluoromethyl, difluoromethyl, trifluoromethyl, cyclopropyl, cyclobutyl, cyclopentyl, cyclohexyl, methoxy, ethoxy, propoxy, butoxy, isopropoxy, methylthio, ethylthio, propylthio, isopropylthio, methylamino, ethylamino, propylamino, dimethylamino, diethylamino, N-methyl-N-ethylamino or the following groups:

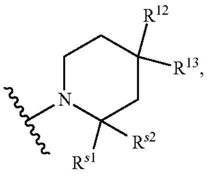

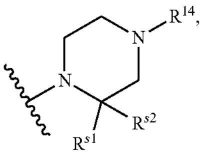

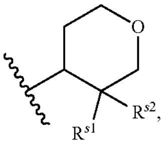

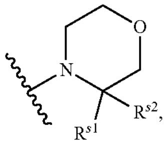

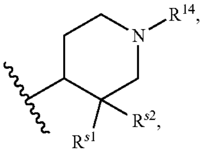

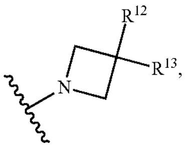

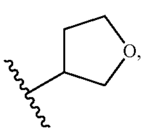

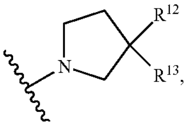

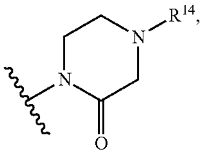

$R^{12}$ is —H, —F, methyl, or ethyl, $R^{13}$ is —H, —F, hydroxyl, hydroxymethyl, cyano, methyl, ethyl, methoxy, or $—NR^{15}R^{16}$, $R^{14}$ is —H, —F, methyl, ethyl, propyl, isopropyl, or

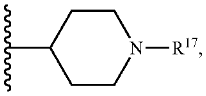

wherein $R^{17}$ is —H, —F, methyl, ethyl, propyl, or isopropyl, $R^{s1}$ and $R^{s2}$ are each independently selected from —H, or methyl;

$R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetanyl, tetrahydrofuranyl, or tetrahydropyranyl, or $R^{15}$ and $R^{16}$ together with the nitrogen atom to which they are attached form a substituted or unsubstituted 4- to 6-membered heteroalicyclic group selected from the following groups:

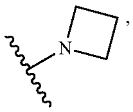

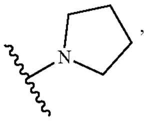

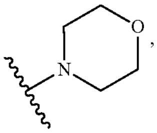

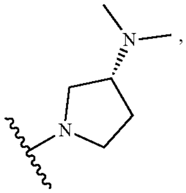

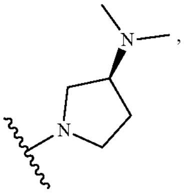

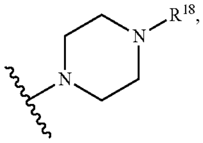

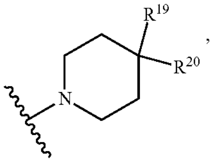

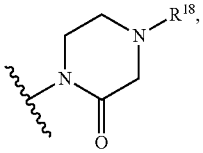

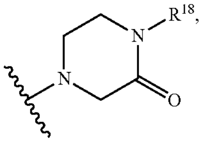

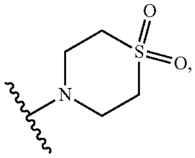

$R^{18}$ is selected from —H, methyl, ethyl, formyl, acetyl, hydroxyethyl, hydroxypropyl, fluoroethyl, fluoropropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, fluoro, formyl, acetyl, hydroxyethyl, hydroxypropyl, fluoroethyl, fluoropropyl, methoxyethyl, methoxypropyl, ethoxyethyl, ethoxypropyl, methylsulfonyl, ethylsulfonyl, amino, methylamino, dimethylamino, methoxy, or ethoxy, and, when $R_4$ is 4-ethyl-piperazin-1-yl, and L is —O— or

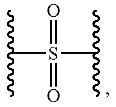 [SMILES: *S(*)(=O)=O]

$R_2$ and $R_3$ are not both hydrogen.

In an alternative embodiment, L is —O—, and, when $R_4$ is 4-ethyl-piperazin-1-yl, $R_2$ and $R_3$ are not both hydrogen.

In a further alternative embodiment, X is N;

L is —O—;

$R^1$ is

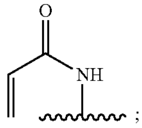 [SMILES: *NC(=O)C=C]

$R_2$ is —H, —F, —Cl, methyl, or methoxy;

$R_3$ is selected from —H, —F, —Cl, hydroxyl, carboxyl, cyano, methyl, ethyl, propyl, isopropyl, tert-butyl, methoxy, ethoxy, propoxy, isopropoxy, cyclopropyloxy, cyclobutyloxy, methylthio, ethylthio, propylthio, isopropylthio, fluoromethyl, difluoromethyl, trifluoromethyl, cyclopropyl, cyclobutyl, cyclopropylmethyl, cyclobutylmethyl, amino, methylamino, ethylamino, dimethylamino, diethylamino, N-methyl-N-ethylamino, methoxyethoxy, ethoxyethoxy, carbamoyl ($NH_2CO$—), or methylsulfonyl;

$R^4$ is $-T_1-R_8$, $T_1$ is selected from:

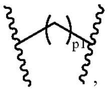

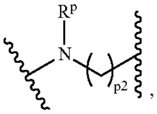

p1 is 0, and p2 is an integer of 2-3;

$R^p$ is selected from —H, methyl, or ethyl;

$R^8$ is selected from methylamino, ethylamino, propylamino, dimethylamino, diethylamino, N-methyl-N-ethylamino or the following groups:

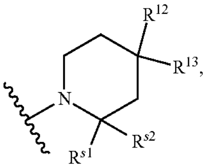

-continued

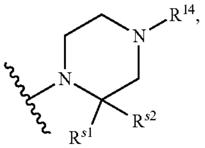

$R^{12}$ is —H, —F, methyl, or ethyl, $R^{13}$ is —H, or $—NR^{15}R^{16}$, $R^{14}$ is —H, methyl, ethyl, propyl, isopropyl, or

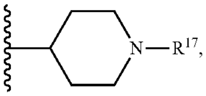

wherein $R^{17}$ is methyl, ethyl, propyl, or isopropyl, $R^{s1}$ and $R^{s2}$ are each independently selected from H, or methyl;

$R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetan-3-yl, tetrahydrofuran-3-yl, or tetrahydro-2H-pyran-4-yl, or $R^{15}$ and $R^{16}$ together with the nitrogen atom to which they are attached form a substituted or unsubstituted 4- to 6-membered heteroalicyclic group selected from the following groups:

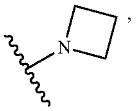

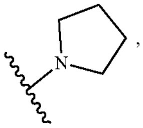

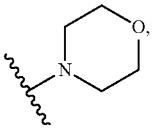

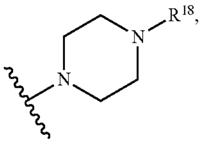

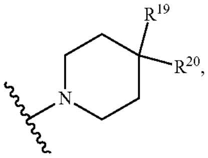

-continued

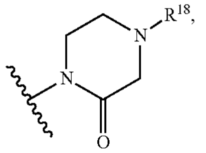

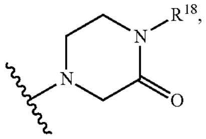

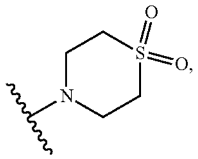

$R^{18}$ is selected from —H, methyl, ethyl, formyl, acetyl, hydroxyethyl, hydroxypropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, fluoro, hydroxyethyl, hydroxypropyl, fluoroethyl, fluoropropyl, methoxyethyl, methoxypropyl, ethoxyethyl, ethoxypropyl, methylsulfonyl, ethylsulfonyl, amino, methylamino, dimethylamino, methoxy, or ethoxy;

and, when $R_4$ is 4-ethyl-piperazin-1-yl, and L is —O— or

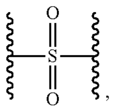

$R_2$ and $R_3$ are not both hydrogen.

In a further alternative embodiment, X is N;

L is —O—;

$R^1$ is

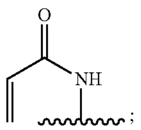 [SMILES: *NC(=O)C=C]

$R_2$ is —H, —F, —Cl, methyl, or methoxy;

$R_3$ is selected from —H, —F, —Cl, hydroxyl, carboxyl, cyano, methyl, ethyl, propyl, isopropyl, tert-butyl, methoxy, ethoxy, propoxy, isopropoxy, cyclopropyloxy, cyclobutyloxy, methylthio, ethylthio, propylthio, isopropylthio, fluoromethyl, difluoromethyl, trifluoromethyl, cyclopropyl, cyclobutyl, cyclopropylmethyl, cyclobutylmethyl, amino, methylamino, ethylamino, dimethylamino, diethylamino, N-methyl-N-ethylamino, methoxyethoxy, ethoxyethoxy, carbamoyl ($NH_2CO$—), or methylsulfonyl;

$R^4$ is

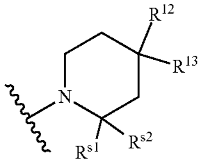

$R^{12}$ is —H, —F, methyl, or ethyl, $R^{13}$ is —H, or —$NR^{15}R^{16}$, $R^{s1}$ and $R^{s2}$ are H, $R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetan-3-yl, tetrahydrofuran-3-yl, or tetrahydro-2H-pyran-4-yl, or $R^{15}$ and $R^{16}$ together with the nitrogen atom to which they are attached form a substituted or unsubstituted 4- to 6-membered heteroalicyclic group selected from the following groups:

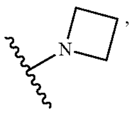

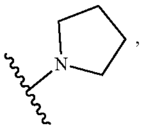

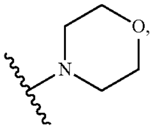

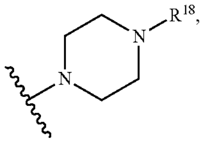

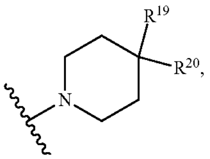

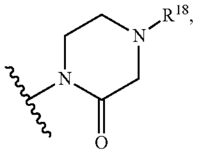

-continued

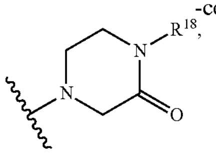

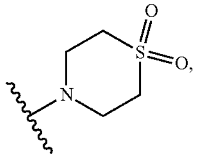

$R^{18}$ is selected from —H, methyl, ethyl, formyl, acetyl, hydroxyethyl, hydroxypropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, or fluoro.

According to some embodiments of the present disclosure, the pharmaceutically acceptable salt of the compound is selected from the group consisting of one or more of the following salts: hydrochloride, hydrobromide, hydroiodide, perchlorate, sulfate, nitrate, phosphate, formate, acetate, propionate, glycolate, lactate, succinate, maleate, tartrate, malate, citrate, fumarate, gluconate, benzoate, mandelate, methanesulfonate, isethionate, benzenesulfonate, oxalate, palmitate, 2-naphthalenesulfonate, p-toluenesulfonate, cyclohexylsulfamate, salicylate, hexonate, trifluoroacetate, aluminum salt, calcium salt, chloroprocaine salt, choline salt, diethanolamine salt, ethylenediamine salt, lithium salt, magnesium salt, potassium salt, sodium salt and zinc salt.

Another aspect of the present disclosure relates to use of the compound of formula (I), or an isomer, a hydrate, a solvate, a pharmaceutically acceptable salt, or a prodrug thereof, in the manufacture of a medicament for treating diseases related to tyrosine kinase FGFR4 or autoimmune diseases, wherein the diseases related to tyrosine kinase FGFR4 or the autoimmune diseases include fundus oculi disease, xerophthalmia, psoriasis, vitiligo, dermatitis, alopecia areata, rheumatoid arthritis, colitis, multiple sclerosis, systemic lupus erythematosus, Crohn's disease, atherosclerosis, pulmonary fibrosis, liver fibrosis, bone marrow fibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myelocytic leukemia, non-Hodgkin's lymphoma, nasopharyngeal cancer, esophageal cancer, brain tumor, B-cell and T-cell lymphoma, lymphoma, multiple myeloma, biliary tract cancerous sarcoma, and cholangiocarcinoma.

Another aspect of the present disclosure provides a pharmaceutical composition comprising the compound represented by formula (I) or an isomer, a hydrate, a solvate, a pharmaceutically acceptable salt, or a prodrug thereof of the present disclosure, and one or more pharmaceutically acceptable carriers or excipients.

According to some embodiments of the present disclosure, the pharmaceutical composition may also include one or more other therapeutic agents.

The present disclosure also relates to a method for treating diseases or conditions mediated by tyrosine kinase FGFR4, which comprises administering a therapeutically effective amount of a compound of formula (I) or a salt thereof to a patient (human or other mammals, especially human) in need thereof, wherein the diseases or conditions mediated by tyrosine kinase FGFR4 include those mentioned above.

DETAILED DESCRIPTION OF THE INVENTION

Unless otherwise stated, the following terms used in this application (including the specification and claims) have the definitions given below. In this application, the use of "or" or "and" means "and/or" unless stated otherwise. In addition, the use of the term "comprising" and other forms such as "including", "containing" and "having" is not limiting. The chapter headings used herein are for organizational purposes only and should not be interpreted as limitations on the topics described.

Unless otherwise specified, an alkyl group refers to a saturated linear and branched hydrocarbon group having a specified number of carbon atoms, and the term $C_1$-$C_6$ alkyl refers to an alkyl moiety containing from 1 to 6 carbon atoms. Similarly, $C_1$-$C_3$ alkyl refers to an alkyl moiety containing from 1 to 3 carbon atoms. For example, $C_1$-$C_6$ alkyl includes methyl, ethyl, propyl, isopropyl, n-butyl, isobutyl, sec-butyl, tert-butyl, n-pentyl, 3-(2-methyl)butyl, 2-pentyl, 2-methylbutyl, neopentyl, n-hexyl, 2-hexyl and 2-methylpentyl, etc.

When a substituent term such as "alkyl" is used in combination with other substituent term, such as in terms "$C_1$-$C_3$ alkoxy-substituted $C_1$-$C_3$ alkyl" or "hydroxyl-substituted $C_2$-$C_6$ alkyl", the linking substituent terms (e.g., alkyl) are intended to encompass a divalent moiety, wherein the point of attachment is through the linking substituent. Examples of "$C_1$-$C_3$ alkoxy-substituted $C_1$-$C_3$ alkyl" include, but are not limited to, methoxymethyl, methoxyethyl and ethoxypropyl, etc. Examples of "hydroxyl-substituted $C_2$-$C_6$ alkyl" include, but are not limited to, hydroxyethyl, hydroxypropyl and hydroxyisopropyl, etc.

An alkoxy group is an alkyl-O— group formed by a linear or branched alkyl group described previously and —O—, e.g., methoxy, ethoxy, and the like. Similarly, an alkylthio group is an alkyl-S— group formed by a linear or branched alkyl group as described previously and —S—, e.g., methylthio, ethylthio, and the like.

Alkenyl and alkynyl groups include linear or branched alkenyl or alkynyl groups, and term $C_2$-$C_3$ alkenyl or $C_2$-$C_3$ alkynyl refers to linear or branched $C_2$-$C_3$ hydrocarbon groups having at least one alkenyl or alkynyl group.

The term "$C_1$-$C_6$ haloalkyl" refers to a group having one or more halogen atoms, which may be the same or different, on one or more carbon atoms of an alkyl moiety comprising 1 to 6 carbon atoms. Examples of "$C_1$-$C_6$ haloalkyl" may include, but are not limited to, —$CF_3$ (trifluoromethyl), —$CCl_3$ (trichloromethyl), 1,1-difluoroethyl, 2,2,2-trifluoroethyl and hexafluoroisopropyl, etc. Similarly, the term "$C_1$-$C_6$ haloalkoxy" refers to a haloalkyl-O— group formed by the $C_1$-$C_6$ haloalkyl and —O—, which can be, for example, trifluoromethoxy, trichloromethoxy, etc.

The term "$C_1$-$C_3$ acyl" includes formyl (—CHO), acetyl ($CH_3CO$—), and propionyl ($C_2H_5CO$—).

"Cycloalkyl" refers to a non-aromatic, saturated, cyclic hydrocarbon group containing a specified number of carbon atoms. For example, the term "($C_3$-$C_6$)cycloalkyl" refers to a non-aromatic cyclic hydrocarbon ring having 3-6 ring carbon atoms. Exemplary "($C_3$-$C_6$)cycloalkyl" includes cyclopropyl, cyclobutyl, cyclopentyl, and cyclohexyl.

The term "aryl" refers to a group or moiety comprising an aromatic monocyclic or bicyclic hydrocarbon radical, which contains from 6 to 12 carbon ring atoms and has at least one aromatic ring. Examples of "aryl" are phenyl, naphthyl, indenyl and dihydroindenyl (indanyl). Generally, in the compounds of the present disclosure, alternatively, the aryl is phenyl.

Unless otherwise specified, the term "4- to 6-membered heteroalicyclic group" as used herein refers to an unsubstituted or substituted stable 4- to 6-membered non-aromatic monocyclic saturated ring system consisting of carbon atoms and 1 to 2 heteroatoms selected from N, O, or S, wherein the N or S heteroatom can be randomly oxidized, and the N heteroatom can also be randomly quaternized. Examples of such heterocycles include, but are not limited to, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, and thiomorpholinyl.

The term "carbonyl" refers to a —C(O)— group. The terms "halogen" and "halo" refer to chlorine, fluorine, bromine or iodine substituent. "Oxo" refers to an oxygen moiety having one double bond; for example, "oxo" may be directly attached to a carbon atom to form a carbonyl moiety (C═O). "Hydroxy" is intended to refer to a radical —OH. The term "cyano" as used herein refers to a group —CN.

The term "each independently" means that where more than one substituent is selected from a number of possible substituents, those substituents may be the same or different.

It is clear that the compound of formula I, or isomer, crystalline form or prodrug thereof, and pharmaceutically acceptable salt thereof, may exist in a solvated or non-solvated form. For example, the solvated form can be a solvated form with water. The present disclosure includes all the solvated and non-solvated forms.

In this disclosure, the term "isomer" refers to different compounds having the same molecular formula, and may include various isomeric forms such as stereoisomers and tautomers. "Stereoisomers" are isomers that differ only in the arrangement of their atoms in space. Some compounds described herein contain one or more asymmetric centers and thus can give rise to enantiomers, diastereomers, and other stereoisomeric forms which can be defined as (R)- or (S)-based on absolute stereochemistry. The chemical entities, pharmaceutical compositions, and methods disclosed herein are intended to include all of these possible isomers, including racemic mixtures, optically pure forms, and intermediate mixtures. Optically active (R)- and (S)-isomers can be prepared using chiral synthons or chiral reagents or resolved using conventional techniques. The optical activity of a compound can be analyzed by any suitable method, including but not limited to chiral chromatography and polarimetry, and the degree of dominance of one stereoisomer over other isomers can be determined.

Individual stereoisomers of a compound of this disclosure may be resolved (or mixtures of stereoisomers may be enriched) using methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

When a compound described herein contains an olefinic double bond, it means that the compound includes various cis- or trans-isomers, unless otherwise stated.

"Tautomers" are structurally different isomers that can be converted to each other through tautomerization. "Tautomerization" is a form of isomerization and includes a proton transfer tautomerization, which can be considered as a subset of acid-base chemistry. "Proton transfer tautomerization" involves the migration of a proton accompanied by a bond-level transformation, which is often exchange of a single bond with an adjacent double bond. When tautomerization is possible (for example, in solution), a chemical equilibrium of tautomers can be reached. An example of tautomerization is keto-enol tautomerization.

The compound of the present disclosure as an active ingredient, and the method of preparing the same, are both included in the present disclosure. Moreover, the crystalline form of some of the compounds may exist as polymorphs, and such forms may also be included in the present disclosure. Additionally, some of the compounds may form solvates with water (i.e., hydrates) or common organic solvents, and such solvates are also included within the scope of the disclosure.

The compounds of the disclosure may be used in the free form for treatment or, when appropriate, in the form of a pharmaceutically acceptable salt or other derivative for treatment. As used herein, the term "pharmaceutically acceptable salt" refers to organic and inorganic salts of the compounds of the present disclosure which are suitable for use in human and lower animals without undue toxicity, irritation, allergic response, etc., and have reasonable benefit/risk ratio. Pharmaceutically acceptable salts of amines, carboxylic acids, phosphonates, and other types of compounds are well known in the art. The salt can be formed by reacting a compound of the disclosure with a suitable free base or acid, including, but not limited to, salts with inorganic acids such as hydrochloric acid, hydrobromic acid, phosphoric acid, sulfuric acid, perchloric acid or with organic acids such as acetic acid, oxalic acid, maleic acid, tartaric acid, citric acid, succinic acid, malonic acid. Or the salts may be obtained by methods well known in the art, such as ion exchange. Other pharmaceutically acceptable salts include adipate, alginate, ascorbate, aspartate, besylate, benzoate, bisulfate, borate, butyrate, camphorate, camphorsulfonate, citrate, digluconate, lauryl sulfate, ethanesulfonate, formate, fumarate, glucoheptonate, glycerol phosphate, glyconate, hemisulfate, hexanoate, hydroiodide, 2-hydroxyethanesulfonate, lactobionate, lactate, laurate, lauryl sulfate, malate, maleate, mesylate, 2-naphthalenesulfonate, nicotinate, nitrate, oleate, palmitate, pamoate, pectate, persulphate, per-3-phenylpropionate, phosphate, picrate, propionate, stearate, sulfate, thiocyanate, p-toluenesulfonate, undecanoate, and the like. Representative alkali or alkaline earth metal salts include salts of sodium, lithium, potassium, calcium, magnesium, and the like. Other pharmaceutically acceptable salts include suitable non-toxic salts of ammonium, quaternary ammonium, and amine cations formed from halides, hydroxides, carboxylates, sulfates, phosphates, nitrates, lower alkyl sulfonates and aryl sulfonates.

Further, the term "prodrug" as used herein means that a compound can be converted into the compound represented by formula (I) of the present disclosure in vivo. Such transformation is affected by hydrolysis of the prodrug in the blood or enzymatic conversion to the parent compound in the blood or tissue.

Pharmaceutical compositions of this disclosure comprise the compounds of formula (I) described herein or a pharmaceutically acceptable salt thereof; an additional agent selected from a kinase inhibitory agent (small molecule, polypeptide, antibody, etc.), an immunosuppressant, an anticancer agent, an anti-viral agent, anti-inflammatory agent, antifungal agent, antibiotic, or an anti-vascular hyper proliferation compound; and any pharmaceutically acceptable carrier, adjuvant or excipient.

The compounds of the present disclosure may be used alone or in combination with one or more of other compounds of the present disclosure or with one or more of other agents. When administered in combination, the therapeutic agents can be formulated for simultaneous or sequential administration at different times, or the therapeutic agents can be administered as a single composition. By "combination therapy", it refers to the use of a compound of the disclosure in combination with another agent in the form of co-administration of each agent or sequential administration of each agent, in either case, for the purpose of achieving the optimal results. Co-administration includes dosage form for simultaneous delivery, as well as separate dosage forms for each compound. Thus, administration of the compounds of the disclosure can be combined with other therapies known in the art, for example, radiation therapy or cytostatic agents, cytotoxic agents, other anticancer agents, and the like as used in the treatment of cancer, in order to improve the symptoms of cancer. The administration sequence is not limited in the present disclosure. The compounds of the present disclosure may be administered before, simultaneously, or after other anticancer or cytotoxic agents.

To prepare the pharmaceutical ingredient of the present disclosure, one or more compounds of Formula (I) or salts thereof as an active ingredient can be intimately mixed with a pharmaceutical carrier, which is carried out according to a conventional pharmaceutical Formulation technique. The carrier can be used in a wide variety of forms depending on the form of preparation which is designed for different administration modes (for example, oral or parenteral administration). Suitable pharmaceutically acceptable carriers are well known in the art. A description of some of these pharmaceutically acceptable carriers can be found in the Handbook of Pharmaceutical Excipients, published jointly by the American Pharmaceutical Association and the Pharmaceutical Society of Great Britain.

The pharmaceutical composition of the present disclosure may have the following forms, for example, those suitable for oral administration, such as tablets, capsules, pills, powders, sustained release forms, solutions or suspensions; those for parenteral injections such as clear solutions, suspensions, emulsion; or those for topical use such as ointments, creams; or as a suppository for rectal administration. The pharmaceutical ingredients may also be presented in unit dosage form for single administration in a precise dosage. The pharmaceutical ingredient will include a conventional pharmaceutical carrier or excipient and a compound as an active ingredient prepared according to the present disclosure, and may also include other medical or pharmaceutical preparations, carriers, adjuvants, and the like.

Therapeutic compounds can also be administered to mammals other than humans. The drug dosage for a mammal will depend on the species of the animal and its disease condition or its disordered condition. The therapeutic compound can be administered to the animal in the form of a capsule, a bolus, or a tablet or liquid. The therapeutic compound can also be introduced into the animal by injection or infusion. These drug forms are prepared in a traditional manner complying with standard veterinary practice. As an alternative, the therapeutic compounds can be mixed with the animal feed and fed to the animal, so that the concentrated feed additive or premix can be prepared by mixing ordinary animal feed.

It is a further object of the present disclosure to provide a method for treating cancer in a subject in need thereof, comprising a method for administering to the subject a therapeutically effective amount of a composition containing the compound of the present disclosure.

The compounds of the present disclosure have better selectivity for FGFR4 than other receptors, especially than other FGF receptors, such as FGFR1, FGFR2 and FGFR3. Accordingly, the present disclosure relates to compounds that are selective FGFR4 inhibitors.

Considering their activity as an inhibitor of FGFR4, the compounds of formula (I) in free or pharmaceutically acceptable salt form are suitable for the treatment of conditions mediated by the activity of FGFR4 proteins (such as cancer) and/or conditions that are responsive to inhibition of FGFR4 (in a therapeutically beneficial manner, in particular), most particularly a disease or disorder as referred to herein below.

The compounds of the present disclosure are useful in the treatment of cancer. In particular, the compounds of the present disclosure can be used for the treatment of indications selected from liver cancer, breast cancer, glioblastoma, prostate cancer, rhabdomyosarcoma, gastric cancer, ovarian cancer, lung cancer, and colon cancer.

The compounds of the present disclosure can also be used to treat solid malignancies characterized by positive FGFR4 expression.

The compounds of the present disclosure can also be used to treat solid malignancies characterized by positive KLB (beta-klotho) expression.

The compounds of the present disclosure can also be used to treat solid malignancies characterized by positive FGF19 expression.

The compounds of the present disclosure can also be used to treat solid malignancies characterized by positive FGFR4 and positive KLB expression.

The compounds of the present disclosure can also be used to treat solid malignancies characterized by positive FGFR4 and positive FGF19 expression.

The compounds of the disclosure can also be used to treat solid malignancies characterized by positive FGFR4, positive KLB and positive FGF19 expression.

Any positive expression in FGFR4, KLB and/or FGF19 as described above can be assessed by methods known to those skilled in the art, e.g., RT-qPCR, Western blotting, ELISA, and immunohistochemistry.

Thus, as a further embodiment, the present disclosure provides use of a compound of formula (I) or a pharmaceutically acceptable salt thereof in treatment of a disease. In a further embodiment, the disease is selected from diseases that can be treated by inhibiting FGFR4. In a further embodiment, the disease is selected from the list mentioned above, suitably liver cancer.

In another embodiment, the present disclosure provides a method of treating a disease that can be treated by inhibition of FGFR4, comprising administering a therapeutically acceptable amount of a compound of formula (I) or a pharmaceutically acceptable salt thereof. In a further embodiment, the disease is selected from the list mentioned above, suitably liver cancer.

Thus, as a further embodiment, the present disclosure provides use of a compound of formula (I) or a pharmaceutically acceptable salt thereof in the manufacture of a medicament. In a further embodiment, the medicament is used for the treatment of a disease that can be treated by inhibiting FGFR4. In a further embodiment, the disease is selected from the list mentioned above, suitably liver cancer.

The present disclosure also provides methods for preparing the corresponding compounds. Various synthetic methods can be used to prepare the compounds described herein, including the methods involved in the following examples. The compounds of the present disclosure, or pharmaceutically acceptable salts, isomers or hydrates thereof can be synthesized using the methods described below, synthetic methods known in the art of organic chemistry synthesis, or variants of these methods understood by those skilled in the art. Alternative methods include, but are not limited to, the methods described below.

The final product of the present disclosure can be prepared by the following scheme, wherein $R_1$, $R_2$, $R_3$, $R_4$, X, and L are as defined above,

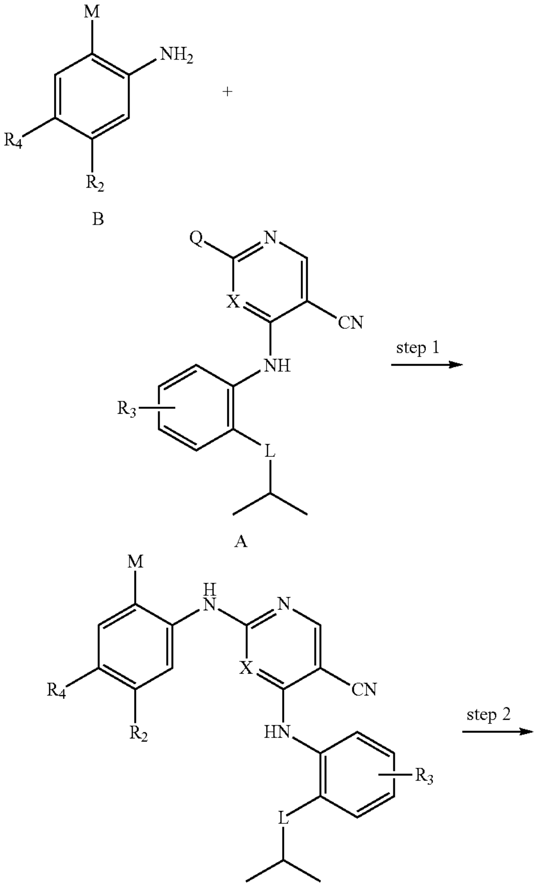

B
A
I'

-continued

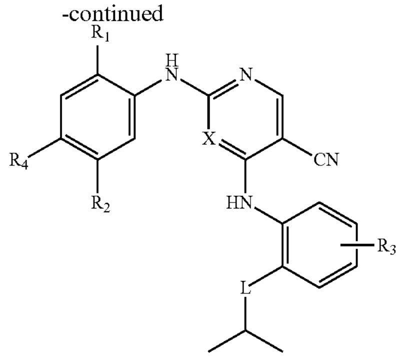

I

In intermediate A, Q may be halogen (alternatively chlorine) or methylsulfonyl (sulfinyl). Where M is BocNH— in intermediate B, the reaction of step 1 can be heated under acid catalysis, neutral conditions or basic conditions to carry out substitution reaction to synthesize compound (I'). Where Q is chlorine in intermediate A, compound (I') can also be synthesized by Buchwald coupling reaction, then treated under acidic conditions to remove the protecting group tert-butyloxycarbonyl, and further reacted with acryloyl chloride to synthesize final product (I).

The preparation method of the compound of the present disclosure comprises the preparation of each of the above intermediates, wherein intermediate (B) is prepared as follows,

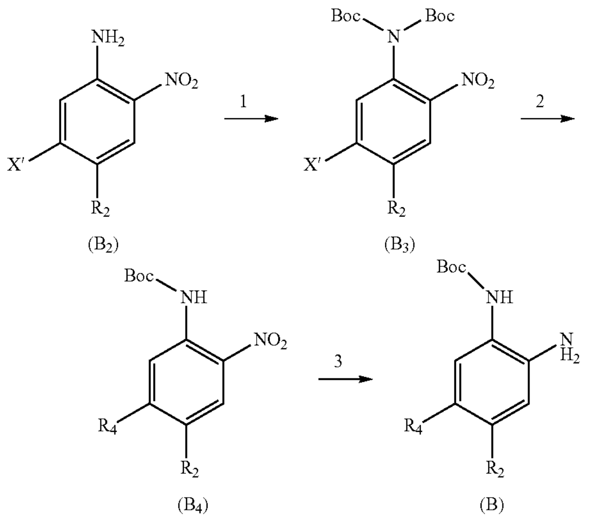

($B_2$) ($B_3$) ($B_4$) (B)

Step 1: Compound ($B_2$) is reacted with $(Boc)_2O$ to give compound ($B_3$), wherein X' can be Cl, F, Br, or I;

Step 2: Compound ($B_3$) is reacted with $R_4$—H (amine or alcohol) under basic or neutral conditions to give compound ($B_4$). Where X' is Cl, Br or I, compound ($B_4$) can also be obtained by Buchwald coupling reaction;

Step 3: Compound ($B_4$) is reacted with a reducing agent to form intermediate (B).

The base described in Step 2 is selected from one or a combination of two or more of inorganic bases or organic bases such as cesium carbonate, triethylamine, sodium hydride, sodium bis(trimethylsilyl)amide, and an alternative condition for Buchwald is a combination of $Pd_2(dba)_3$, XantPhos and cesium carbonate;

The reducing agent described in Step 3 is selected from a combination of stannous chloride, hydrogen gas, and palladium on carbon, a combination of hydrogen gas and Raney nickel, a combination of zinc powder and acid, a combination of iron powder and acid, and other reducing agent systems;

Intermediate (A) is prepared as follows,

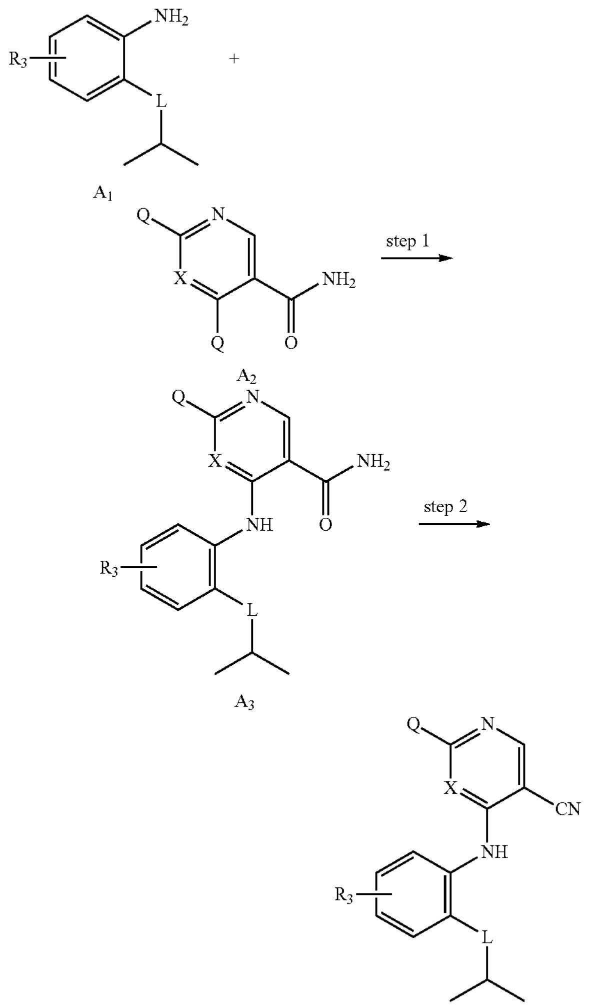

$A_1$, $A_2$, $A_3$

Step 1: Compound ($A_2$) is subjected to substitution reaction with $A_1$ in the presence of a base to give ($A_3$);

Step 2: Compound ($A_3$) is dehydrated from the amide under the condition of a dehydrating agent to give compound (A).

The present disclosure provides alternative embodiments of the above reactions, alternatively, in Step 1, the base is selected from one or a combination of two or more of organic or inorganic bases, such as triethylamine, N,N-diisopropylethylamine, sodium hydride, sodium bis(trimethylsilyl)amide, and n-butyllithium;

alternatively, the dehydrating agent is selected from phosphorus oxychloride, aluminum trichloride, phosphorus pentoxide, phosphorus chloride (phosphorus pentachloride or phosphorus trichloride) and the like.

In order to make the objectives, technical solutions and advantages of the present disclosure more clear, the present disclosure will be further described in detail below in conjunction with specific examples. It should be understood that the specific examples described here are only used to explain the present disclosure and are not intended to limit the present invention. If no specific technology or conditions are indicated in examples, the technology or conditions described in the literature in the art or the product specification shall be followed. If reagents or instruments used do not indicate manufacturers, they are all conventional products that are commercially available. The term "and/or" as used herein includes any and all combinations of one or more related listed items. The names of some compounds in this disclosure are generated by Chemdraw and translated into Chinese.

I. Source of Chemical Reagents

Reaction solvents were provided by Sinopharm Chemical Reagent Co., Ltd.

Common chemical raw materials were provided by Innochem, Energy, Macklin, J&K, PharmaBlock and other suppliers.

Thin-layer chromatography silica gel plates (thickness 0.5 mm, 1 mm, 200×200 mm) were provided by Yantai Xinnuo Chemical Co., Ltd.

Silica gels (200-300 mesh) were provided by Sinopharm Chemical Reagent Co., Ltd.

II. Chemical Abbreviation

DMF: N,N-dimethylformamide
DIEA: N,N-diisopropylethylamine
NMP: N-methylpyrrolidone
$Pd(OAc)_2$: Palladium acetate
$Pd_2(dba)_3$: Tris(dibenzylideneacetone)dipalladium
Xantphos: 4,5-Bis(diphenylphosphino)-9,9-dimethylxanthene
Binap: 2,2'-Bis(diphenylphosphino)-1,1'-binaphthalene
$(Boc)_2O$: Di-tert-butyl dicarbonate

III. Preparation of Intermediates

Intermediates of Series A

Intermediate A1. 2-chloro-4-((2-isopropoxyphenyl)amino)pyrimidine-5-carbonitrile

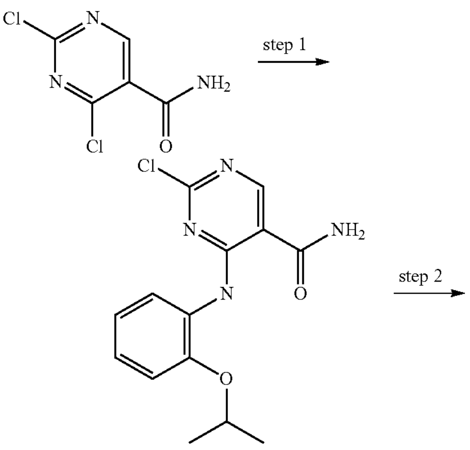

-continued

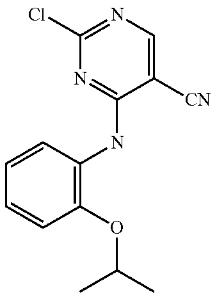

Step 1). Synthesis of 2-chloro-4-((2-isopropoxyphenyl)amino)pyrimidine-5-carboxamide 2,4-Dichloropyrimidine-5-carboxamide (1.9 g, 10 mmol), 2-isopropoxyaniline (1.65 g, 11 mmol) and triethylamine (2 g, 20 mmol) were added to DMF (10 mL), respectively. The reaction solution was stirred at room temperature for 2 hours, and then water was added for slurrying. The resultant slurry was filtered, and the filter cake was dried to give 2.5 g of product as a white solid with a yield of 82%, MS:307 $[M+H]^+$;

Step 2). Synthesis of 2-chloro-4-((2-isopropoxyphenyl)amino)pyrimidine-5-carbonitrile 2-Chloro-4-((2-isopropoxyphenyl)amino)pyrimidine-5-carboxamide (307 mg, 1 mmol) was added to phosphorus oxychloride (2 mL). The mixture was heated to 120° C., and reacted with stirring for 5 hours. The reaction solution was concentrated, and washed with saturated sodium bicarbonate solution to give 220 mg of product as a yellowish solid with a yield of 76%, MS: 289 $[M+H]^+$.

The following intermediates A2-A23 were obtained through the same reaction steps as those of intermediate A1 by replacing the 2-isopropoxyaniline in the above Step 1 with aniline compounds having different substituents. The structures, names and mass spectral data of intermediates A2-A23 are shown in Table 1 below.

TABLE 1

Structures, names and mass spectral data of intermediates A2-A23

| No. | Structure | Name | LCMS m/z = $(M + H)^+$ |
|---|---|---|---|
| A2 | 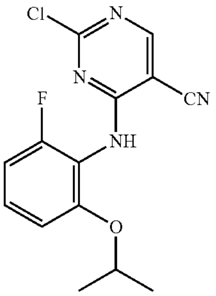 [SMILES: CC(C)Oc1cccc(F)c1Nc1nc(Cl)ncc1C#N] | 2-chloro-4-((2-fluoro-6-isopropoxyphenyl)amino)pyrimidine-5-carbonitrile | 307 |
| A3 | 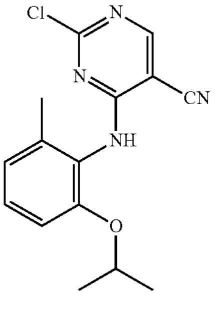 [SMILES: Cc1cccc(OC(C)C)c1Nc1nc(Cl)ncc1C#N] | 2-chloro-4-((2-isopropoxy-6-methylphenyl)amino)pyrimidine-5-carbonitrile | 303 |
| A4 | 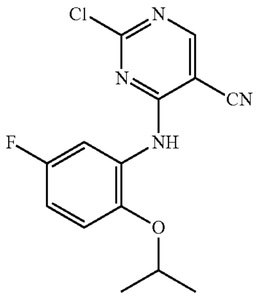 [SMILES: CC(C)Oc1ccc(F)cc1Nc1nc(Cl)ncc1C#N] | 2-chloro-4-((5-fluoro-2-isopropoxyphenyl)amino)pyrimidine-5-carbonitrile | 307 |

TABLE 1-continued

Structures, names and mass spectral data of intermediates A2-A23

| No. | Structure | Name | LCMS m/z = (M + H)$^+$ |
|---|---|---|---|
| A5 | 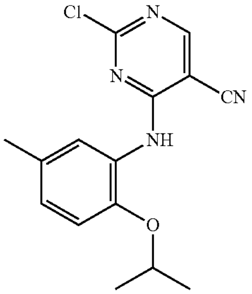 [SMILES: Cc1ccc(OC(C)C)c(Nc2nc(Cl)ncc2C#N)c1] | 2-chloro-4-((2-isopropoxy-5-methylphenyl)amino)pyrimidine-5-carbonitrile | 303 |
| A6 | 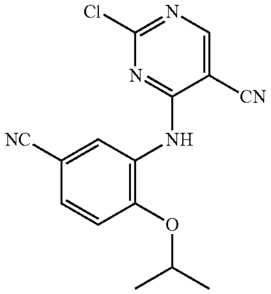 [SMILES: CC(C)Oc1ccc(C#N)cc1Nc1nc(Cl)ncc1C#N] | 2-chloro-4-((5-cyano-2-isopropoxyphenyl)amino)pyrimidine-5-carbonitrile | 314 |
| A7 | 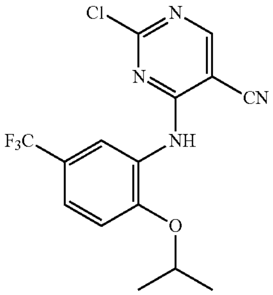 [SMILES: CC(C)Oc1ccc(C(F)(F)F)cc1Nc1nc(Cl)ncc1C#N] | 2-chloro-4-((2-isopropoxy-5-(trifluoromethyl)phenyl)amino) pyrimidine-5-carbonitrile | 357 |
| A8 | 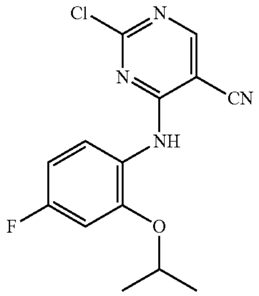 [SMILES: CC(C)Oc1cc(F)ccc1Nc1nc(Cl)ncc1C#N] | 2-chloro-4-((4-fluoro-2-isopropoxyphenyl)amino)pyrimidine-5-carbonitrile | 307 |
| A9 | 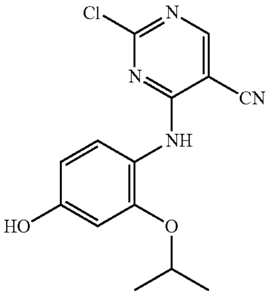 | 2-chloro-4-((4-hydroxy-2-isopropoxyphenyl)amino)pyrimidine-5-carbonitrile | 305 |

TABLE 1-continued

| Structures, names and mass spectral data of intermediates A2-A23 | | | |
|---|---|---|---|
| No. | Structure | Name | LCMS m/z = $(M + H)^+$ |
| A10 | 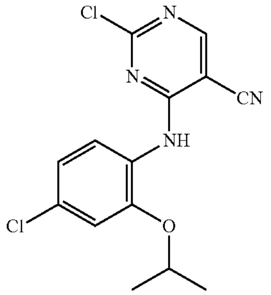 [SMILES: CC(C)Oc1cc(Cl)ccc1Nc1nc(Cl)ncc1C#N] | 2-chloro-4-((4-chloro-2-isopropoxyphenyl)amino)pyrimidine-5-carbonitrile | 323 |
| A11 | 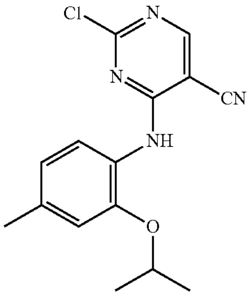 [SMILES: Cc1ccc(Nc2nc(Cl)ncc2C#N)c(OC(C)C)c1] | 2-chloro-4-((2-isopropoxy-4-methylphenyl)amino)pyrimidine-5-carbonitrile | 303 |
| A12 | 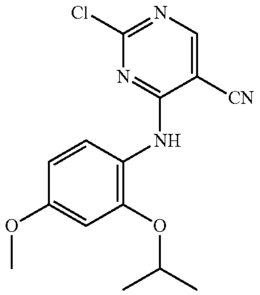 [SMILES: COc1ccc(Nc2nc(Cl)ncc2C#N)c(OC(C)C)c1] | 2-chloro-4-((2-isopropoxy-4-methoxyphenyl)amino)pyrimidine-5-carbonitrile | 319 |
| A13 | 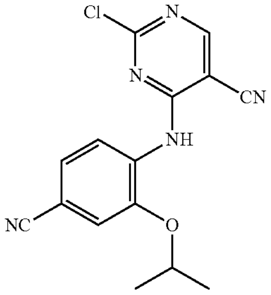 [SMILES: CC(C)Oc1cc(C#N)ccc1Nc1nc(Cl)ncc1C#N] | 2-chloro-4-((4-cyano-2-isopropoxyphenyl)amino)pyrimidine-5-carbonitrile | 314 |

TABLE 1-continued

Structures, names and mass spectral data of intermediates A2-A23

| No. | Structure | Name | LCMS m/z = (M + H)$^+$ |
|---|---|---|---|
| A14 | 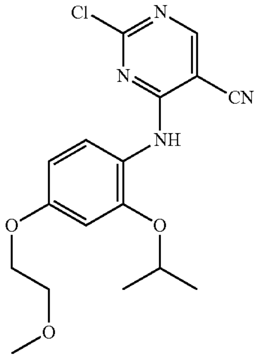 [SMILES: COCCOc1ccc(Nc2nc(Cl)ncc2C#N)c(OC(C)C)c1] | 2-chloro-4-((2-isopropoxy-4-(2-methoxyethoxy)phenyl)amino) pyrimidine-5-carbonitrile | 363 |
| A15 | 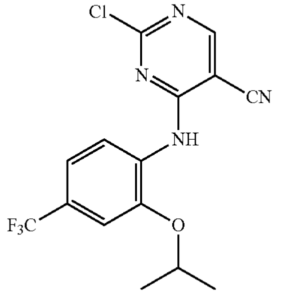 [SMILES: CC(C)Oc1cc(C(F)(F)F)ccc1Nc1nc(Cl)ncc1C#N] | 2-chloro-4-((2-isopropoxy-4-(trifluoromethyl)phenyl)amino) pyrimidine-5-carbonitrile | 357 |
| A16 | 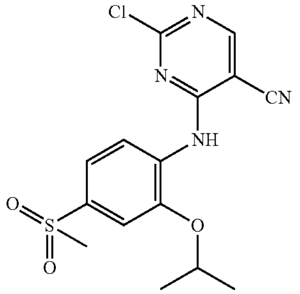 [SMILES: CC(C)Oc1cc(S(C)(=O)=O)ccc1Nc1nc(Cl)ncc1C#N] | 2-chloro-4-((2-isopropoxy-4-(methylsulfonyl)phenyl)amino) pyrimidine-5-carbonitrile | 367 |
| A17 | 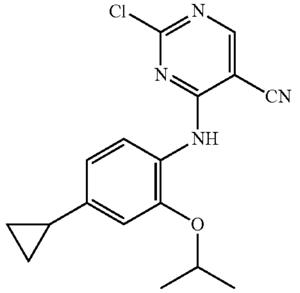 [SMILES: CC(C)Oc1cc(C2CC2)ccc1Nc1nc(Cl)ncc1C#N] | 2-chloro-4-((4-cyclopropyl-2-isopropoxyphenyl)amino)pyrimidine-5-carbonitrile | 329 |

TABLE 1-continued

| Structures, names and mass spectral data of intermediates A2-A23 | | | |
|---|---|---|---|
| No. | Structure | Name | LCMS m/z = $(M + H)^+$ |
| A18 | 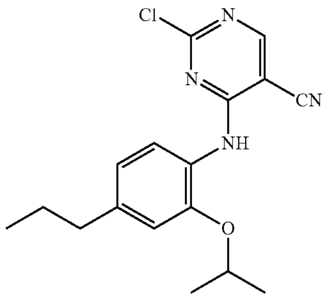 [SMILES: CCCc1ccc(Nc2nc(Cl)ncc2C#N)c(OC(C)C)c1] | 2-chloro-4-((2-isopropoxy-4-propylphenyl)amino)pyrimidine-5-carbonitrile | 331 |
| A19 | 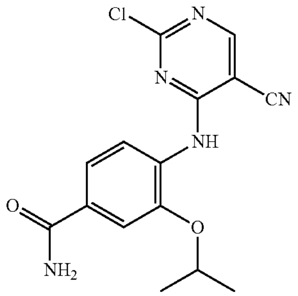 [SMILES: CC(C)Oc1cc(C(N)=O)ccc1Nc1nc(Cl)ncc1C#N] | 4-((2-chloro-5-cyanopyrimidin-4-yl)amino)-3-isopropoxybenzamide | 332 |
| A20 | 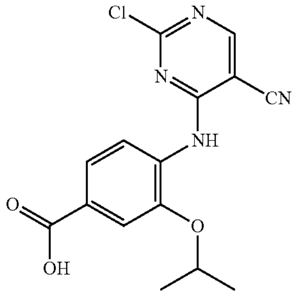 [SMILES: CC(C)Oc1cc(C(=O)O)ccc1Nc1nc(Cl)ncc1C#N] | 4-((2-chloro-5-cyanopyrimidin-4-yl)amino)-3-isopropoxybenzoic acid | 333 |
| A21 | 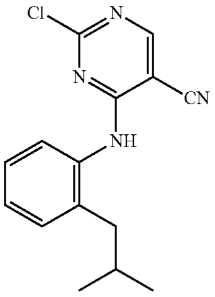 [SMILES: CC(C)Cc1ccccc1Nc1nc(Cl)ncc1C#N] | 2-chloro-4-((2-isobutylphenyl)amino)pyrimidine-5-carbonitrile | 287 |
| A22 | 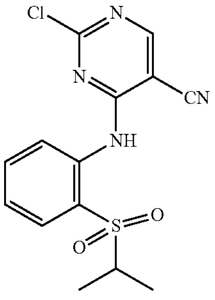 [SMILES: CC(C)S(=O)(=O)c1ccccc1Nc1nc(Cl)ncc1C#N] | 2-chloro-4-((2-(isopropylsulfonyl)phenyl)amino) pyrimidine-5-carbonitrile | 337 |

TABLE 1-continued

| Structures, names and mass spectral data of intermediates A2-A23 | | | |
|---|---|---|---|
| No. | Structure | Name | LCMS m/z = (M + H)$^+$ |
| A23 | 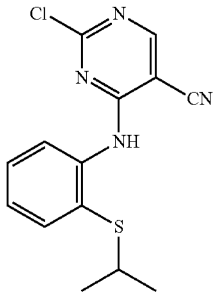 [SMILES: CC(C)Sc1ccccc1Nc1nc(Cl)ncc1C#N] | 2-chloro-4-((2-(isopropylthio)phenyl)amino) pyrimidine-5-carbonitrile | 305 |

Intermediates of Series B

Intermediate B1. Preparation of tert-butyl (2-amino-5-(4-ethylpiperazin-1-yl)phenyl)carbamate

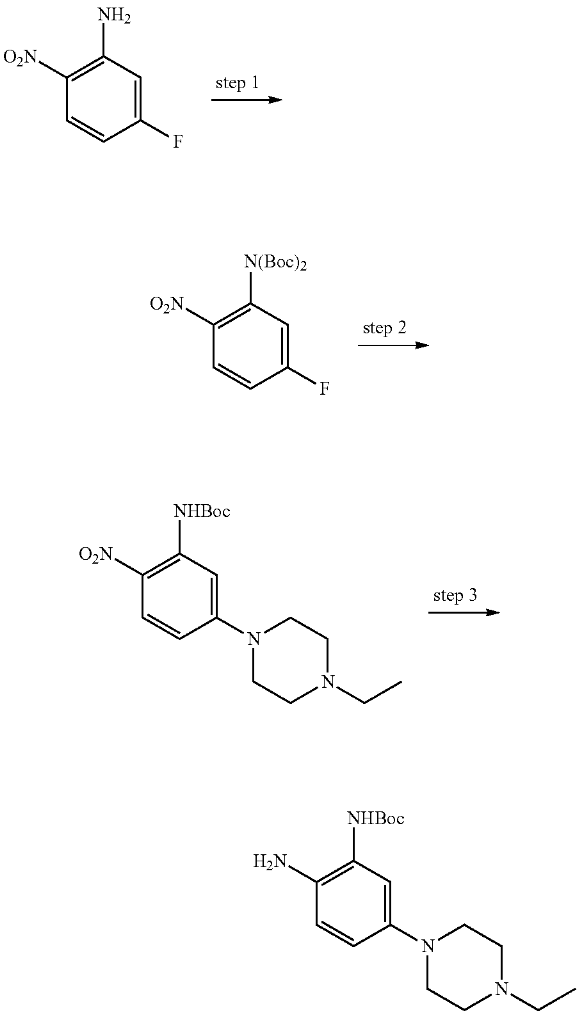

Step 1) Preparation of N,N-di-tert-butoxycarbonyl-2-nitro-5-fluoroaniline

5-Fluoro-2-nitroaniline (1.6 g, 10 mmol), $(Boc)_2O$ (4.7 g, 22 mmol), and DMAP (0.37 g, 3 mmol) were added to dichloromethane respectively, and the mixture was stirred at room temperature overnight. The reaction solution was concentrated, and purified by column chromatography (silica gel, mobile phase: petroleum ether/ethyl acetate=10/1) to give 3.3 g of product as a bright yellow solid, MS:357[M+H]$^+$;

Step 2) Preparation of tert-butyl (5-(4-ethylpiperazin-1-yl)-2-nitrophenyl)carbamate N,N-di-tert-butoxycarbonyl-2-nitro-5-fluoroaniline (3.3 g, 9.2 mmol) and ethylpiperazine (3 mL) were added to DMF respectively, and the mixture was heated to 120° C. and reacted for 8 hours. The reaction solution was cooled, and concentrated, and the residue was purified by column chromatography to give 3.1 g of yellow solid, MS: 351[M+H]$^+$;

Step 3) Preparation of tert-butyl (2-amino-5-(4-ethylpiperazin-1-yl)phenyl)carbamate Tert-butyl (5-(4-ethylpiperazin-1-yl)-2-nitrophenyl)carbamate (3.1 g, 8.9 mmol) was added to a solution of Pd/C in methanol. The atmosphere was replaced twice with hydrogen gas. The mixture was stirred at room temperature for 3 hours. The reaction solution was filtered, concentrated, and slurried with dichloromethane. The slurry was filtered to give 2.5 g of white solid, MS:321[M+H]$^+$.

The following intermediates B2-B56 were obtained through similar reaction steps to those of intermediate B1 by replacing the 5-fluoro-2-nitroaniline in the above Step 1 with 5-fluoro-2-nitroaniline compounds having different substituents, and replacing the ethylpiperazine in Step 2 with different bases. The structures, names and mass spectral data of intermediates B2-B56 are shown in Table 2 below.

TABLE 2

| Structures, names and mass spectrometry data of intermediates B2-B56 | | | |
|---|---|---|---|
| No. | Structure | Name | LCMS m/z = (M + H)+ |
| B2 | 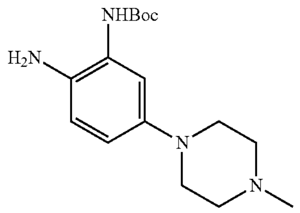 [SMILES: CN1CCN(c2ccc(N)c(NC(=O)OC(C)(C)C)c2)CC1] | tert-butyl(2-amino-5-(4-methylpiperazin-1-yl)phenyl)carbamate | 307 |
| B3 | 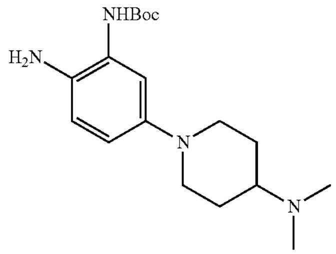 [SMILES: CN(C)C1CCN(c2ccc(N)c(NC(=O)OC(C)(C)C)c2)CC1] | tert-butyl(2-amino-5-(4-(dimethylamino)piperidin-1-yl)phenyl)carbamate | 335 |
| B4 | 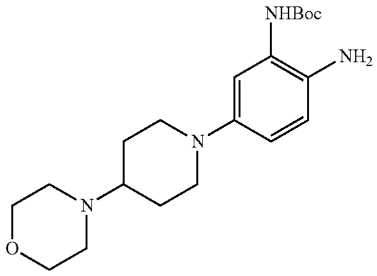 [SMILES: CC(C)(C)OC(=O)Nc1cc(N2CCC(N3CCOCC3)CC2)ccc1N] | tert-butyl(2-amino-5-(4-morpholinopiperidin-1-yl)phenyl)carbamate | 377 |
| B5 | 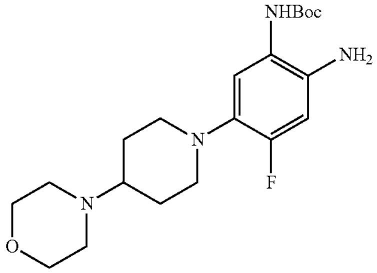 [SMILES: CC(C)(C)OC(=O)Nc1cc(N2CCC(N3CCOCC3)CC2)c(F)cc1N] | tert-butyl(2-amino-4-fluoro-5-(4-morpholinopiperidin-1-yl)phenyl)carbamate | 395 |
| B6 | 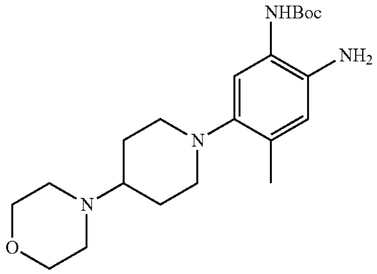 [SMILES: Cc1cc(N)c(NC(=O)OC(C)(C)C)cc1N1CCC(N2CCOCC2)CC1] | tert-butyl(2-amino-4-methyl-5-(4-morpholinopiperidin-1-yl)phenyl)carbamate | 391 |

TABLE 2-continued

Structures, names and mass spectrometry data of intermediates B2-B56

| No. | Structure | Name | LCMS m/z = (M + H)+ |
|---|---|---|---|
| B7 | 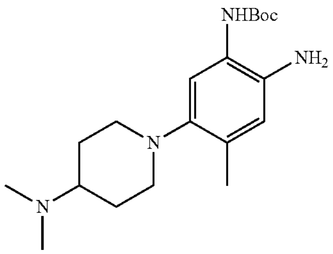 [SMILES: Cc1cc(N)c(NC(=O)OC(C)(C)C)cc1N1CCC(N(C)C)CC1] | tert-butyl(2-amino-5-(4-(dimethylamino)piperidin-1-yl)-4-methylphenyl)carbamate | 349 |
| B8 | 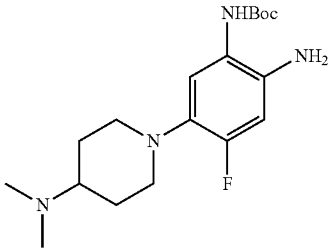 [SMILES: CN(C)C1CCN(c2cc(NC(=O)OC(C)(C)C)c(N)cc2F)CC1] | tert-butyl(2-amino-5-(4-(dimethylamino)piperidin-1-yl)-4-fluorophenyl)carbamate | 353 |
| B9 | 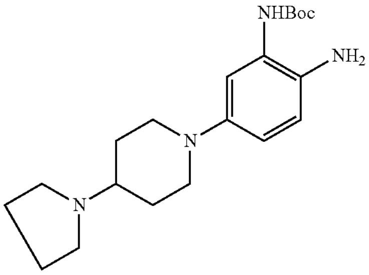 [SMILES: CC(C)(C)OC(=O)Nc1cc(N2CCC(N3CCCC3)CC2)ccc1N] | tert-butyl(2-amino-5-(4-(pyrrolidin-1-yl)piperidin-1-yl)phenyl)carbamate | 361 |
| B10 | 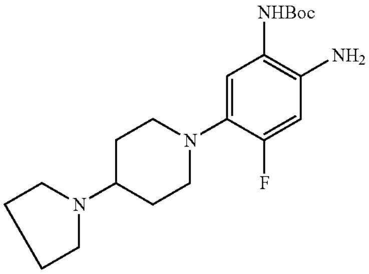 [SMILES: CC(C)(C)OC(=O)Nc1cc(N2CCC(N3CCCC3)CC2)c(F)cc1N] | tert-butyl(2-amino-4-fluoro-5-(4-(pyrrolidin-1-yl)piperidin-1-yl)phenyl)carbamate | 379 |
| B11 | 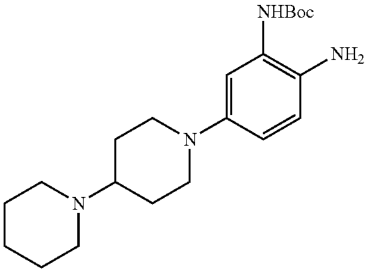 [SMILES: CC(C)(C)OC(=O)Nc1cc(N2CCC(N3CCCCC3)CC2)ccc1N] | tert-butyl(5-([1,4'-bipiperidin]-1'-yl)-2-aminophenyl)carbamate | 375 |

TABLE 2-continued

Structures, names and mass spectrometry data of intermediates B2-B56

| No. | Structure | Name | LCMS m/z = (M + H)+ |
|---|---|---|---|
| B12 | 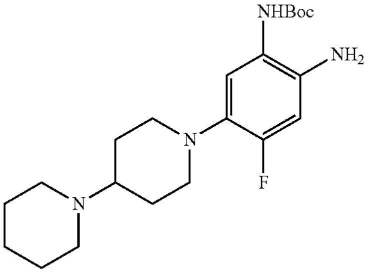 [SMILES: CC(C)(C)OC(=O)Nc1cc(N2CCC(N3CCCCC3)CC2)c(F)cc1N] | tert-butyl(5-([1,4'-bipiperidin]-1'-yl)-2-amino-4-fluorophenyl)carbamate | 393 |
| B13 | 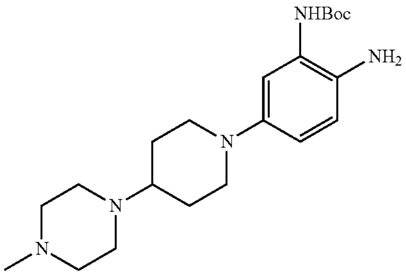 [SMILES: CN1CCN(C2CCN(c3ccc(N)c(NC(=O)OC(C)(C)C)c3)CC2)CC1] | tert-butyl(2-amino-5-(4-(4-methylpiperazin-1-yl)piperidin-1-yl)phenyl)carbamate | 390 |
| B14 | 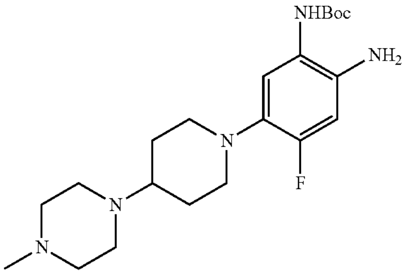 [SMILES: CN1CCN(C2CCN(c3cc(NC(=O)OC(C)(C)C)c(N)cc3F)CC2)CC1] | tert-butyl(2-amino-4-fluoro-5-(4-(4-methylpiperazin-1-yl)piperidin-1-yl)phenyl)carbamate | 408 |
| B15 | 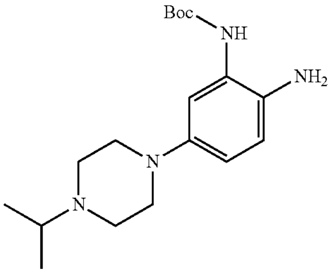 [SMILES: CC(C)N1CCN(c2ccc(N)c(NC(=O)OC(C)(C)C)c2)CC1] | tert-butyl(2-amino-5-(4-isopropylpiperazin-1-yl)phenyl)carbamate | 335 |
| B16 | 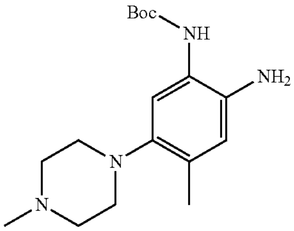 [SMILES: Cc1cc(N)c(NC(=O)OC(C)(C)C)cc1N1CCN(C)CC1] | tert-butyl(2-amino-4-methyl-5-(4-methylpiperazin-1-yl)phenyl)carbamate | 321 |

TABLE 2-continued

| Structures, names and mass spectrometry data of intermediates B2-B56 | | | |
|---|---|---|---|
| No. | Structure | Name | LCMS m/z = $(M + H)^+$ |
| B17 | 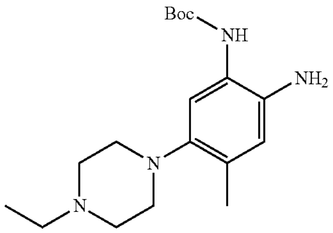 [SMILES: CCN1CCN(c2cc(NC(=O)OC(C)(C)C)c(N)cc2C)CC1] | tert-butyl(2-amino-5-(4-ethylpiperazin-1-yl)-4-methylphenyl)carbamate | 335 |
| B18 | 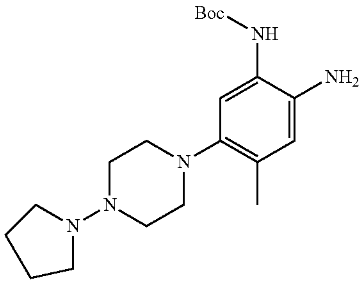 [SMILES: Cc1cc(N)c(NC(=O)OC(C)(C)C)cc1N1CCN(N2CCCC2)CC1] | tert-butyl(2-amino-4-methyl-5-(4-(pyrrolidin-1-yl)piperidin-1-yl)phenyl)carbamate | 375 |
| B19 | 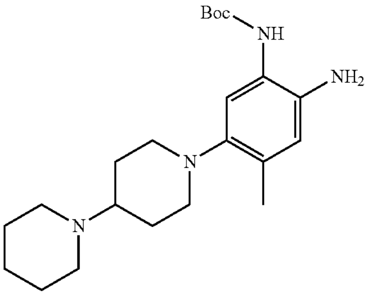 [SMILES: Cc1cc(N)c(NC(=O)OC(C)(C)C)cc1N1CCC(N2CCCCC2)CC1] | tert-butyl(5-([1,4'-bipiperidin]-1'-yl)-2-amino-4-methylphenyl)carbamate | 389 |
| B20 | 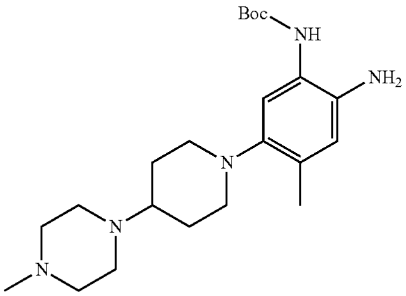 [SMILES: Cc1cc(N)c(NC(=O)OC(C)(C)C)cc1N1CCC(N2CCN(C)CC2)CC1] | tert-butyl(2-amino-4-methyl-5-(4-(4-methylpiperazin-1-yl)piperidin-1-yl)phenyl)carbamate | 404 |
| B21 | 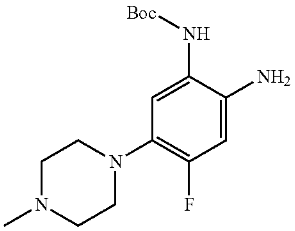 | tert-butyl(2-amino-4-fluoro-5-(4-methylpiperazin-1-yl)phenyl)carbamate | 325 |

TABLE 2-continued

Structures, names and mass spectrometry data of intermediates B2-B56

| No. | Structure | Name | LCMS m/z = $(M + H)^+$ |
|---|---|---|---|
| B22 | 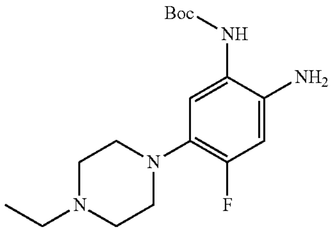 [SMILES: CCN1CCN(c2cc(NC(=O)OC(C)(C)C)c(N)cc2F)CC1] | tert-butyl(2-amino-5-(4-ethylpiperazin-1-yl)-4-fluorophenyl)carbamate | 339 |
| B23 | 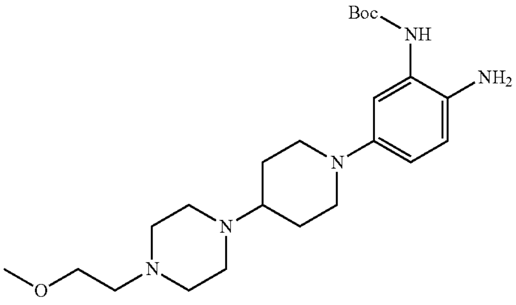 [SMILES: COCCN1CCN(C2CCN(c3ccc(N)c(NC(=O)OC(C)(C)C)c3)CC2)CC1] | tert-butyl(2-amino-5-(4-(4-(2-methoxyethyl)piperazin-1-yl)piperidin-1-yl)phenyl)carbamate | 434 |
| B24 | 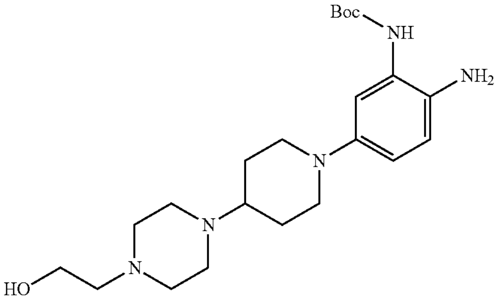 [SMILES: CC(C)(C)OC(=O)Nc1cc(N2CCC(N3CCN(CCO)CC3)CC2)ccc1N] | tert-butyl(2-amino-5-(4-(4-(2-hydroxyethyl)piperazin-1-yl)piperidin-1-yl)phenyl)carbamate | 420 |
| B25 | 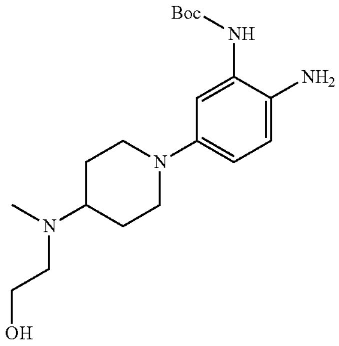 [SMILES: CN(CCO)C1CCN(c2ccc(N)c(NC(=O)OC(C)(C)C)c2)CC1] | tert-butyl(2-amino-5-(4-((2-hydroxyethyl)(methyl)amino)piperidin-1-yl)phenyl)carbamate | 365 |

TABLE 2-continued

| Structures, names and mass spectrometry data of intermediates B2-B56 | | | |
|---|---|---|---|
| No. | Structure | Name | LCMS m/z = $(M + H)^+$ |
| B26 | 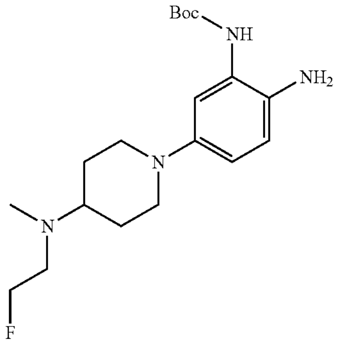 [SMILES: CN(CCF)C1CCN(c2ccc(N)c(NC(=O)OC(C)(C)C)c2)CC1] | tert-butyl(2-amino-5-(4-((2-fluoroethyl)(methyl)amino)piperidin-1-yl)phenyl)carbamate | 367 |
| B27 | 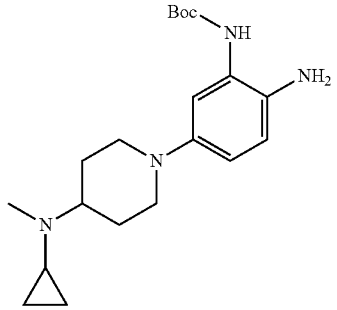 [SMILES: CN(C1CC1)C1CCN(c2ccc(N)c(NC(=O)OC(C)(C)C)c2)CC1] | tert-butyl(2-amino-5-(4-(cyclopropyl(methyl)amino)piperidin-1-yl)phenyl)carbamate | 361 |
| B28 | 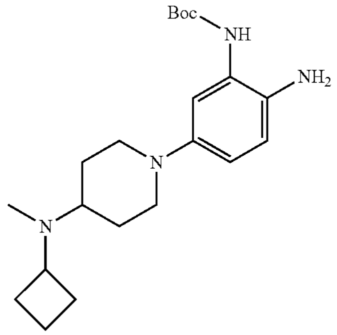 [SMILES: CN(C1CCC1)C1CCN(c2ccc(N)c(NC(=O)OC(C)(C)C)c2)CC1] | tert-butyl(2-amino-5-(4-(cyclobutyl(methyl)amino)piperidin-1-yl)phenyl)carbamate | 375 |
| B29 | 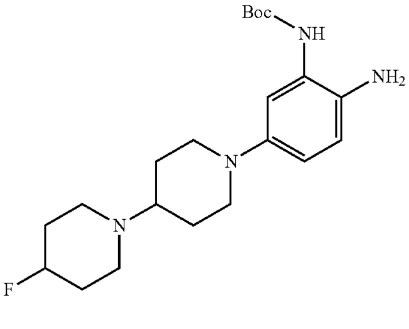 [SMILES: CC(C)(C)OC(=O)Nc1cc(N2CCC(N3CCC(F)CC3)CC2)ccc1N] | tert-butyl(2-amino-5-(4-fluoro-[1,4'-bipiperidin]-1'-yl)phenyl)carbamate | 393 |

TABLE 2-continued

| Structures, names and mass spectrometry data of intermediates B2-B56 | | | |
|---|---|---|---|
| No. | Structure | Name | LCMS m/z = $(M + H)^+$ |
| B30 | 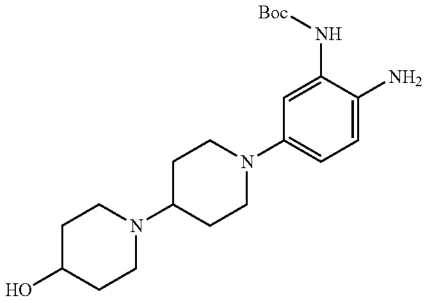 [SMILES: CC(C)(C)OC(=O)Nc1cc(N2CCC(N3CCC(C#N)CC3)CC2)ccc1N] | tert-butyl(2-amino-5-(4-hydroxy-[1,4'-bipiperidin]-1'-yl)phenyl)carbamate | 391 |
| B31 | 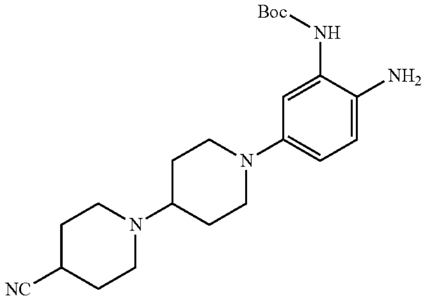 | tert-butyl(2-amino-5-(4-cyano-[1,4'-bipiperidin]-1'-yl)phenyl)carbamate | 400 |
| B32 | 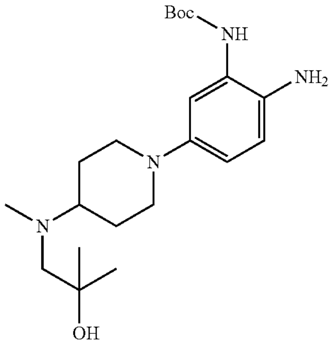 [SMILES: CN(CC(C)(C)O)C1CCN(c2ccc(N)c(NC(=O)OC(C)(C)C)c2)CC1] | tert-butyl(2-amino-5-(4-((2-hydroxy-2-methylpropyl)(methyl)amino)piperidin-1-yl)phenyl)carbamate | 393 |
| B33 | 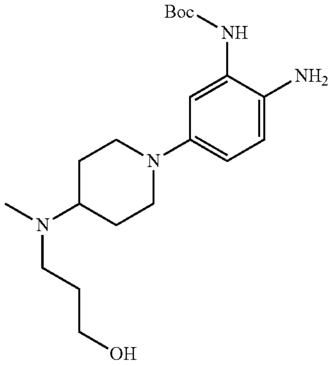 [SMILES: CN(CCCO)C1CCN(c2ccc(N)c(NC(=O)OC(C)(C)C)c2)CC1] | tert-butyl(2-amino-5-(4-((3-hydroxypropyl)(methyl)amino)piperidin-1-yl)phenyl)carbamate | 379 |

TABLE 2-continued
| Structures, names and mass spectrometry data of intermediates B2-B56 | | | |
|---|---|---|---|
| No. | Structure | Name | LCMS m/z = $(M + H)^+$ |
| B34 | 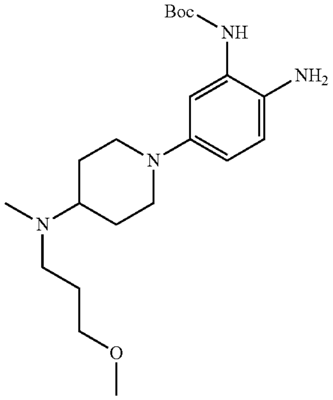 [SMILES: COCCCN(C)C1CCN(c2ccc(N)c(NC(=O)OC(C)(C)C)c2)CC1] | tert-butyl(2-amino-5-(4-((3-methoxypropyl)(methyl)amino)piperidin-1-yl)phenyl)carbamate | 393 |
| B35 | 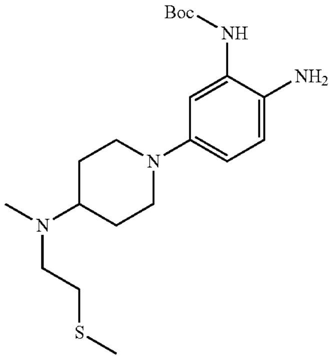 [SMILES: CSCCN(C)C1CCN(c2ccc(N)c(NC(=O)OC(C)(C)C)c2)CC1] | tert-butyl(2-amino-5-(4-(methyl(2-(methylthio)ethyl)amino)piperidin-1-yl)phenyl)carbamate | 395 |
| B36 | 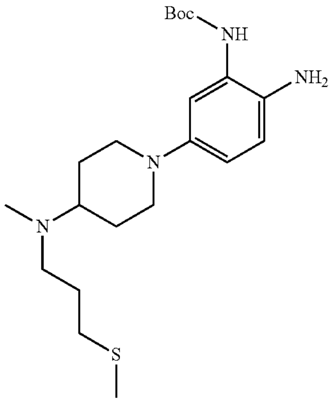 [SMILES: CSCCCN(C)C1CCN(c2ccc(N)c(NC(=O)OC(C)(C)C)c2)CC1] | tert-butyl(2-amino-5-(4-(methyl(3-(methylthio)propyl)amino)piperidin-1-yl)phenyl)carbamate | 409 |

TABLE 2-continued

| Structures, names and mass spectrometry data of intermediates B2-B56 | | | |
|---|---|---|---|
| No. | Structure | Name | LCMS m/z = $(M + H)^+$ |
| B37 | 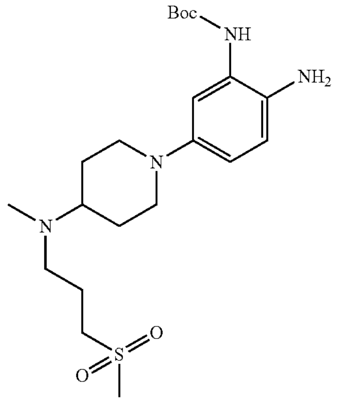 [SMILES: CN(CCCS(C)(=O)=O)C1CCN(c2ccc(N)c(NC(=O)OC(C)(C)C)c2)CC1] | tert-butyl(2-amino-5-(4-(methyl(3-(methylsulfonyl)propyl)amino)piperidin-1-yl)phenyl)carbamate | 441 |
| B38 | 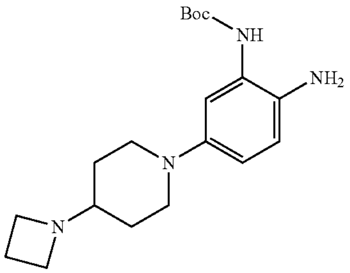 [SMILES: CC(C)(C)OC(=O)Nc1cc(N2CCC(N3CCC3)CC2)ccc1N] | tert-butyl(2-amino-5-(4-(azetidin-1-yl)piperidin-1-yl)phenyl)carbamate | 347 |
| B39 | 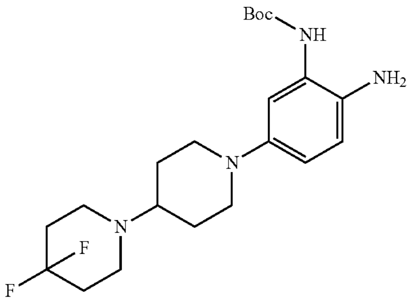 | tert-butyl(2-amino-5-(4,4-difluoro-[1,4'-bipiperidin]-1'-yl)phenyl)carbamate | 411 |
| B40 | 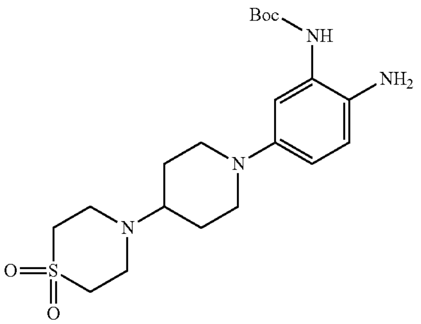 [SMILES: CC(C)(C)OC(=O)Nc1cc(N2CCC(N3CCS(=O)(=O)CC3)CC2)ccc1N] | tert-butyl(2-amino-5-(4-(1,1-dioxidothiomorpholino)piperidin-1-yl)phenyl)carbamate | 425 |

TABLE 2-continued

Structures, names and mass spectrometry data of intermediates B2-B56

| No. | Structure | Name | LCMS m/z = $(M + H)^+$ |
|---|---|---|---|
| B41 | 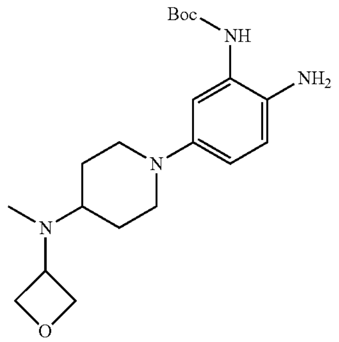 [SMILES: CN(C1CCN(c2ccc(N)c(NC(=O)OC(C)(C)C)c2)CC1)C1COC1] | tert-butyl(2-amino-5-(4-(methyl(oxetan-3-yl)amino)piperidin-1-yl)phenyl)carbamate | 377 |
| B42 | 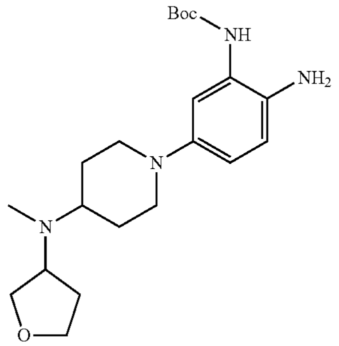 [SMILES: CN(C1CCN(c2ccc(N)c(NC(=O)OC(C)(C)C)c2)CC1)C1CCOC1] | tert-butyl(2-amino-5-(4-(methyl(tetrahydrofuran-3-yl)amino)piperidin-1-yl)phenyl)carbamate | 391 |
| B43 | 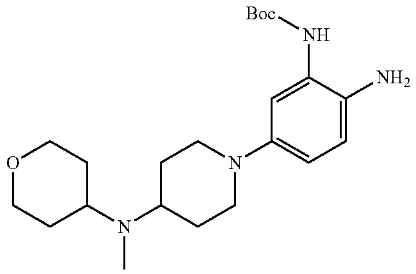 [SMILES: CN(C1CCOCC1)C1CCN(c2ccc(N)c(NC(=O)OC(C)(C)C)c2)CC1] | tert-butyl(2-amino-5-(4-(methyl(tetrahydro-2H-pyran-4-yl)amino)piperidin-1-yl)phenyl)carbamate | 405 |
| B44 | 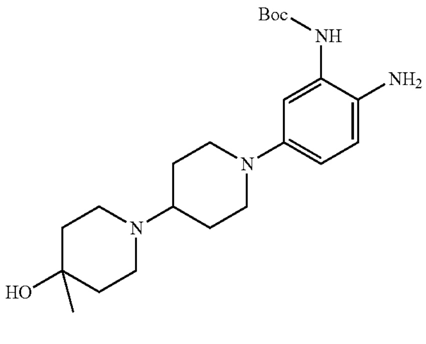 [SMILES: CC1(O)CCN(C2CCN(c3ccc(N)c(NC(=O)OC(C)(C)C)c3)CC2)CC1] | tert-butyl(2-amino-5-(4-hydroxy-4-methyl-[1,4'-bipiperidin]-1'-yl)phenyl)carbamate | 405 |

TABLE 2-continued

| Structures, names and mass spectrometry data of intermediates B2-B56 | | | |
|---|---|---|---|
| No. | Structure | Name | LCMS m/z = (M + H)+ |
| B45 | 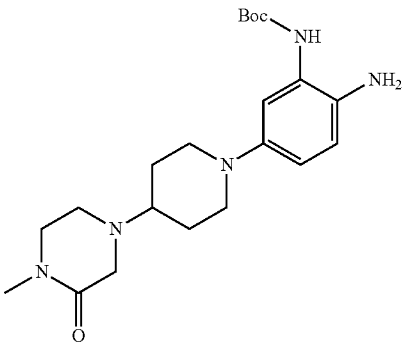 [SMILES: CN1CCN(C2CCN(c3ccc(N)c(NC(=O)OC(C)(C)C)c3)CC2)CC1=O] | tert-butyl(2-amino-5-(4-(4-methyl-3-oxopiperazin-1-yl)piperidin-1-yl)phenyl)carbamate | 404 |
| B46 | 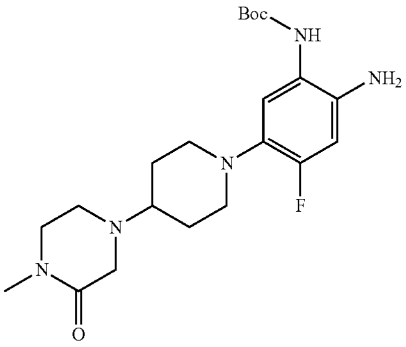 [SMILES: CN1CCN(C2CCN(c3cc(NC(=O)OC(C)(C)C)c(N)cc3F)CC2)CC1=O] | tert-butyl(2-amino-4-fluoro-5-(4-(4-methyl-3-oxopiperazin-1-yl)piperidin-1-yl)phenyl)carbamate | 422 |
| B47 | 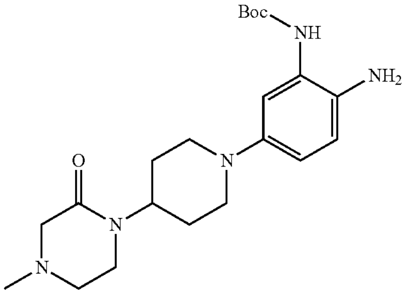 [SMILES: CN1CCN(C2CCN(c3ccc(N)c(NC(=O)OC(C)(C)C)c3)CC2)C(=O)C1] | tert-butyl(2-amino-5-(4-(4-methyl-2-oxopiperazin-1-yl)piperidin-1-yl)phenyl)carbamate | 404 |
| B48 | 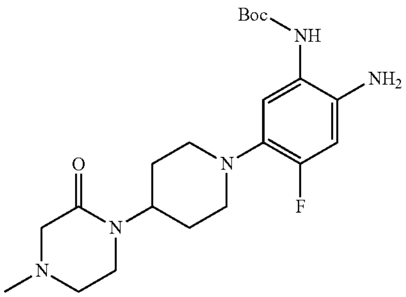 [SMILES: CN1CCN(C2CCN(c3cc(NC(=O)OC(C)(C)C)c(N)cc3F)CC2)C(=O)C1] | tert-butyl(2-amino-4-fluoro-5-(4-(4-methyl-2-oxopiperazin-1-yl)piperidin-1-yl)phenyl)carbamate | 422 |

TABLE 2-continued

| Structures, names and mass spectrometry data of intermediates B2-B56 | | | |
|---|---|---|---|
| No. | Structure | Name | LCMS m/z = $(M + H)^+$ |
| B49 | 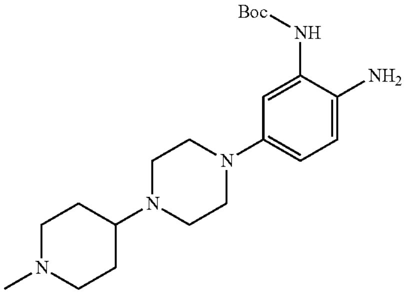 [SMILES: CN1CCC(N2CCN(c3ccc(N)c(NC(=O)OC(C)(C)C)c3)CC2)CC1] | tert-butyl(2-amino-5-(4-(1-methylpiperidin-4-yl)piperazin-1-yl)phenyl)carbamate | 390 |
| B50 | 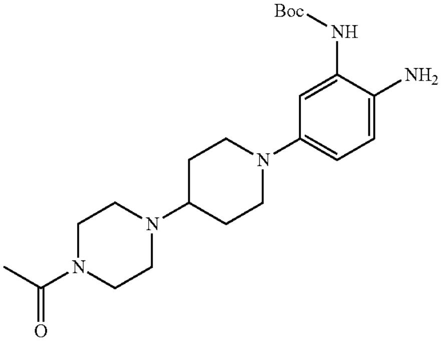 [SMILES: CC(=O)N1CCN(C2CCN(c3ccc(N)c(NC(=O)OC(C)(C)C)c3)CC2)CC1] | tert-butyl(5-(4-(4-acetylpiperazin-1-yl)piperidin-1-yl)-2-aminophenyl)carbamate | 418 |
| B51 | 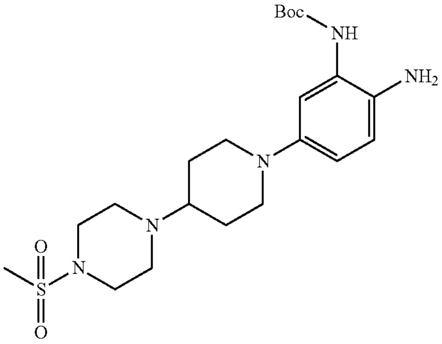 [SMILES: CC(C)(C)OC(=O)Nc1cc(N2CCC(N3CCN(S(C)(=O)=O)CC3)CC2)ccc1N] | tert-butyl(2-amino-5-(4-(4-(methylsulfonyl)piperazin-1-yl)piperidin-1-yl)phenyl)carbamate | 454 |
| B52 | 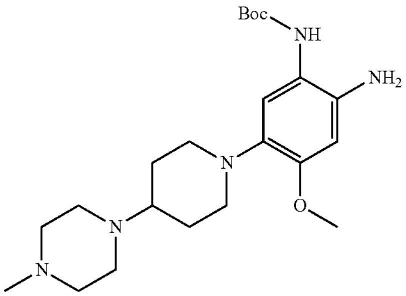 [SMILES: COc1cc(N)c(NC(=O)OC(C)(C)C)cc1N1CCC(N2CCN(C)CC2)CC1] | tert-butyl(2-amino-4-methoxy-5-(4-(4-methylpiperazin-1-yl)piperidin-1-yl)phenyl)carbamate | 420 |

TABLE 2-continued

| Structures, names and mass spectrometry data of intermediates B2-B56 | | | |
|---|---|---|---|
| No. | Structure | Name | LCMS m/z = $(M + H)^+$ |
| B53 | 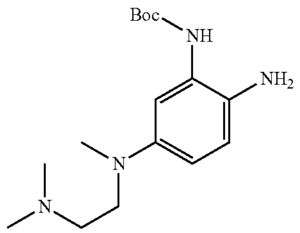 [SMILES: CN(C)CCN(C)c1ccc(N)c(NC(=O)OC(C)(C)C)c1] | tert-butyl(2-amino-5-((2-(dimethylamino)ethyl)(methyl)amino)phenyl)carbamate | 309 |
| B54 | 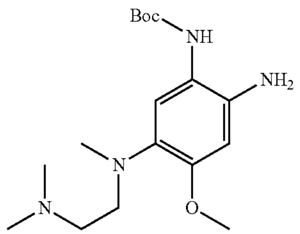 [SMILES: COc1cc(N)c(NC(=O)OC(C)(C)C)cc1N(C)CCN(C)C] | tert-butyl(2-amino-5-((2-(dimethylamino)ethyl)(methyl)amino)-4-methoxyphenyl)carbamate | 339 |
| B55 | 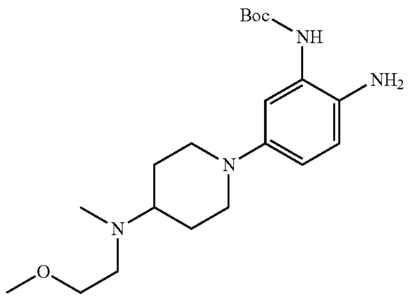 [SMILES: COCCN(C)C1CCN(c2ccc(N)c(NC(=O)OC(C)(C)C)c2)CC1] | tert-butyl(2-amino-5-(4-((2-methoxyethyl)(methyl)amino)piperidin-1-yl)phenyl)carbamate | 379 |
| B56 | 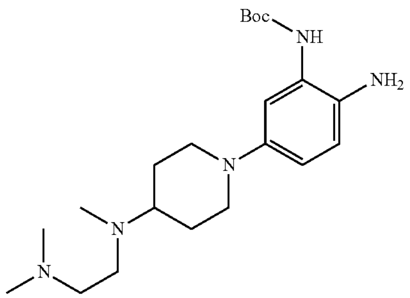 [SMILES: CN(C)CCN(C)C1CCN(c2ccc(N)c(NC(=O)OC(C)(C)C)c2)CC1] | tert-butyl(2-amino-5-(4-((2-(dimethylamino)ethyl)(methyl)amino)piperidin-1-yl)phenyl)carbamate | 392 |

IV. Preparation of Specific Examples

Example 1: N-(2-((5-cyano-4-((2-isopropoxyphenyl) amino)pyrimidin-2-yl)amino)-5-(4-methylpiperazin-1-yl)phenyl)acrylamide

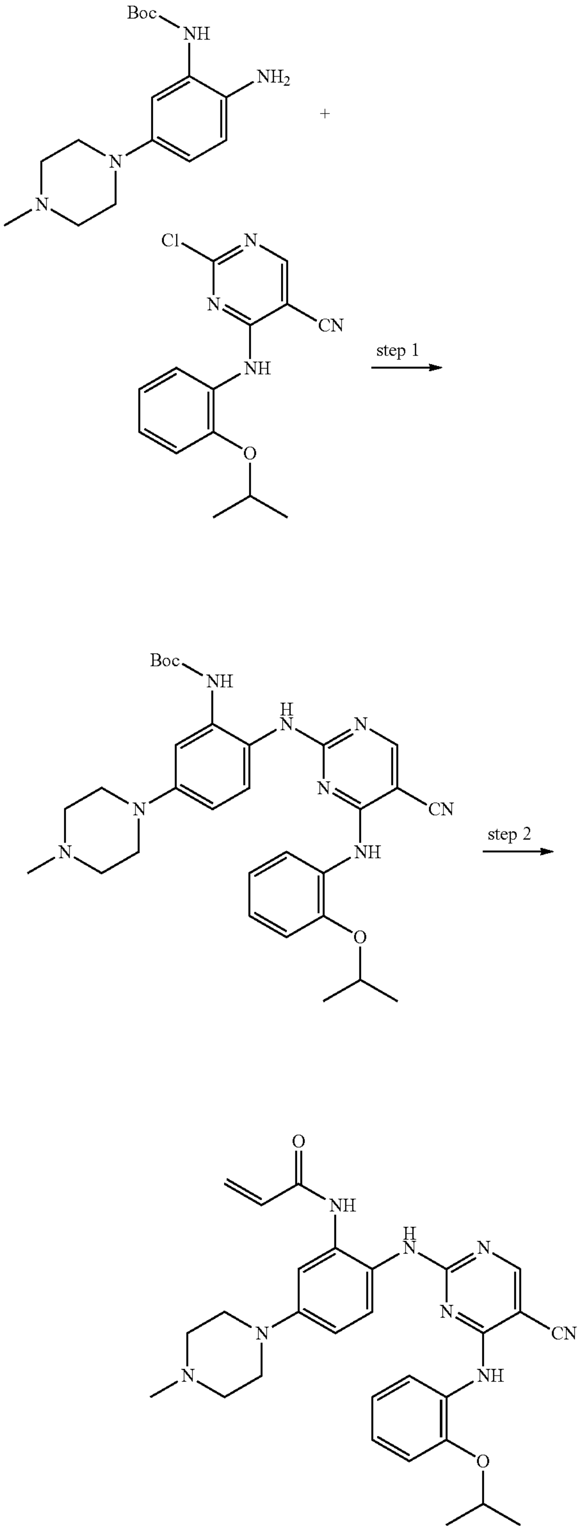

Step 1: Synthesis of tert-butyl (2-((5-cyano-4-((2-isopropoxyphenyl)amino)pyrimidin-2-yl)amino)-5-(4-methylpiperazin-1-yl)phenyl)carbamate The intermediate 2-chloro-4-((2-isopropoxyphenyl) amino)pyrimidine-5-carbonitrile (160 mg, 0.55 mmol), tert-butyl (2-amino-5-(4-methylpiperazin-1-yl)phenyl)carbamate (155 mg, 0.5 mmol) and trifluoroacetic acid (catalytic amount, 20 1) were added to sec-butanol, and the mixture was reacted with heating for 12 hours. The reaction solution was cooled, concentrated, and washed with saturated sodium carbonate solution. The organic phase was concentrated and purified by silica gel column chromatography to give 240 mg of product as a white solid with a yield of 86%, MS: 559[M+H]$^+$;

Step 2: Synthesis of N-(2-((5-cyano-4-((2-isopropoxyphenyl)amino)pyrimidin-2-yl)amino)-5-(4-methylpiperazin-1-yl)phenyl)acrylamide Tert-butyl (2-((5-cyano-4-((2-isopropoxyphenyl)amino) pyrimidin-2-yl)amino)-5-(4-methylpiperazin-1-yl)phenyl) carbamate (120 mg, 0.2 mmol) was added to a solvent of trifluoroacetic acid (1 mL) and dichloromethane (2 mL). The mixture was reacted with stirring at room temperature for 3 hours. The reaction solution was concentrated to give a gray oil. The oil was dissolved in anhydrous tetrahydrofuran (1 mL). Acryloyl chloride (28 mg, 0.3 mmol) was slowly added dropwise under ice-water bath, and the reaction solution was stirred for another 0.5 hours. The reaction mixture was quenched by adding water, washed with saturated sodium bicarbonate solution, and extracted with dichloromethane. The organic phase was dried, concentrated, and purified by preparative silica gel plate (mobile phase: methanol/dichloromethane with a volume ratio of 8/100) to give 45 mg of product as a white solid. $^1$H NMR (400 MHz, DMSO-$d_6$) δ 9.66 (s, 1H), 8.97 (s, 1H), 8.47 (s, 1H), 8.24 (s, 1H), 7.94 (s, 1H), 7.33 (d, J=25.8 Hz, 2H), 7.08 (s, 2H), 6.82 (d, J=9.1 Hz, 1H), 6.72 (s, 1H), 6.50 (dd, J=16.9, 10.2 Hz, 1H), 6.24 (dd, J=17.0, 2.0 Hz, 1H), 5.78-5.70 (m, 1H), 4.74-4.47 (m, 1H), 3.14 (s, 4H), 2.47 (d, J=5.2 Hz, 4H), 2.24 (s, 3H), 1.33-1.21 (m, 6H). MS:513[M+H]$^+$.

Compounds in the following Table were prepared with reference to the preparation method of Example 1 using the corresponding intermediates. The structures, names, and hydrogen NMR and mass spectrometry characterization data of the compounds prepared in Examples 2-81 are shown in Table 3 below.

TABLE 3

| Structures, names and hydrogen NMR and mass spectrometry characterization data of the compounds prepared in Examples 2-81. | | | |
|---|---|---|---|
| No. | Structure | Name | Characterization |
| Example 2 | 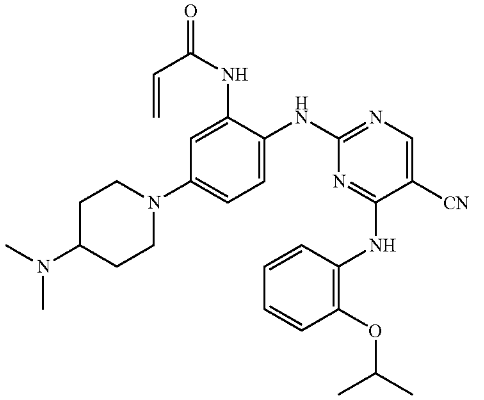 [SMILES: C=CC(=O)Nc1cc(N2CCC(N(C)C)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(dimethylamino)piperidin-1-yl)phenyl)acrylamide | $^1$H NMR (400 MHz, DMSO-$d_6$) δ 9.67 (s, 1H), 8.95 (s, 1H), 8.79 (s, 1H), 8.47 (s, 1H), 8.25 (s, 1H), 7.96 (s, 1H), 7.35 (s, 1H), 7.29 (s, 1H), 7.15-7.00 (m, 2H), 6.85-6.77 (m, 1H), 6.50 (dd, J = 17.0, 10.1 Hz, 1H), 6.24 (dd, J = 16.9, 2.0 Hz, 1H), 5.79-5.70 (m, 1H), 4.68-4.60 (m, 1H), 3.70 (d, J = 12.3 Hz, 2H), 2.71 (t, J = 11.8 Hz, 2H), 2.21 (s, 6H), 2.00 (q, J = 7.2 Hz, 1H), 1.85 (d, J = 12.2 Hz, 2H), 1.56-1.42 (m, 2H), 1.28 (d, J = 6.0 Hz, 6H). MS: 541 $[M + H]^+$ |
| Example 3 | 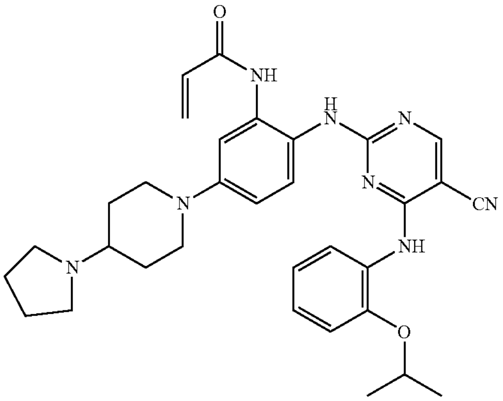 [SMILES: C=CC(=O)Nc1cc(N2CCC(N3CCCC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(pyrrolidin-1-yl)piperidin-1-yl)phenyl)acrylamide | $^1$H NMR (400 MHz, DMSO-$d_6$) δ 9.68 (s, 1H), 8.97 (s, 1H), 8.47 (s, 1H), 8.25 (s, 1H), 7.95 (s, 1H), 7.35 (s, 1H), 7.30 (s, 1H), 7.07 (t, J = 13.3 Hz, 2H), 6.81 (dd, J = 9.2, 2.7 Hz, 1H), 6.73 (s, 1H), 6.50 (dd, J = 16.9, 10.2 Hz, 1H), 6.24 (dd, J = 17.0, 2.1 Hz, 1H), 5.74 (dd, J = 10.2, 2.0 Hz, 1H), 4.68-4.60 (m, 1H), 3.64 (d, J = 12.2 Hz, 2H), 2.77 (t, J = 11.8 Hz, 2H), 2.58 (s, 4H), 2.23 (s, 1H), 1.95 (d, J = 11.9 Hz, 2H), 1.75-1.67 (m, 4H), 1.54 (d, J = 11.5 Hz, 2H), 1.28 (d, J = 5.9 Hz, 6H). MS: 567 $[M + H]^+$ |
| Example 4. | 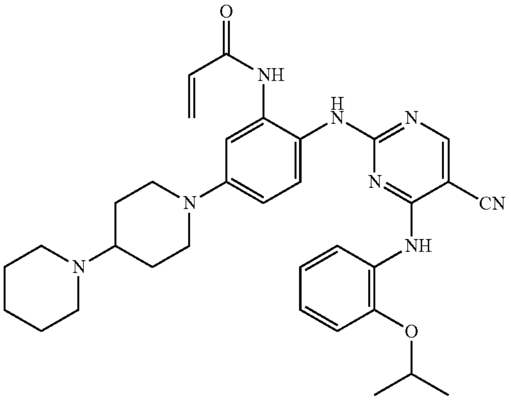 [SMILES: C=CC(=O)Nc1cc(N2CCC(N3CCCCC3)CC2)ccc1Nc1ncc(C#N)c(Nc2ccccc2OC(C)C)n1] | N-(5-([1,4'-bipiperidin]-1'-yl)-2-((5-cyano-4-((2-isopropoxyphenyl)amino)pyrimidin-2-yl)amino)phenyl)acrylamide | $^1$H NMR (400 MHz, DMSO-$d_6$) δ 9.65 (s, 1H), 8.96 (s, 1H), 8.47 (s, 1H), 8.24 (s, 1H), 7.96 (s, 1H), 7.32 (d, J = 18.0 Hz, 2H), 7.06 (d, J = 18.2 Hz, 2H), 6.84-6.77 (m, 1H), 6.69 (d, J = 19.3 Hz, 1H), 6.50 (dd, J = 16.9, 10.1 Hz, 1H), 6.24 (dd, J = 17.0, 2.0 Hz, 1H), 5.79-5.70 (m, 1H), 4.68-4.60 (m, 1H), 3.72 (d, J = 12.2 Hz, 2H), 2.69 (t, J = 11.9 Hz, 2H), 2.51-2.31 (m, 4H), 1.99 (p, J = 7.1, 6.6 Hz, 1H), 1.80 (d, J = 12.3 Hz, 2H), 1.58-1.44 (m, 6H), 1.39 (s, 2H), 1.28 (d, J = 6.0 Hz, 6H). MS: 581 $[M + H]^+$ |

TABLE 3-continued

Structures, names and hydrogen NMR and mass spectrometry characterization data of the compounds prepared in Examples 2-81.

| No. | Structure | Name | Characterization |
| --- | --- | --- | --- |
| Example 5. | 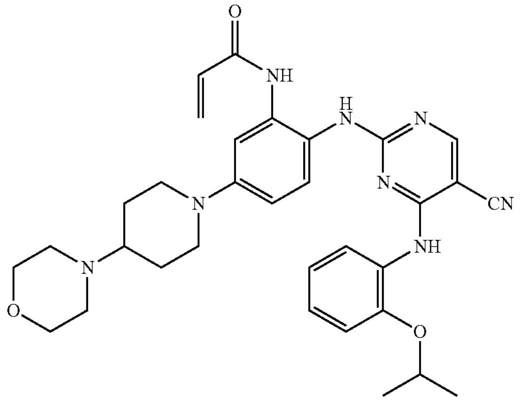 [SMILES: C=CC(=O)Nc1cc(N2CCC(N3CCOCC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-morpholinopiperidin-1-yl)phenyl)acrylamide | $^1$H NMR (400 MHz, DMSO-$d_6$) δ 9.65 (s, 1H), 8.96 (s, 1H), 8.47 (s, 1H), 8.24 (s, 1H), 7.95 (s, 1H), 7.43-7.21 (m, 2H), 7.06 (d, J = 17.7 Hz, 2H), 6.81 (d, J = 8.8 Hz, 1H), 6.71 (s, 1H), 6.50 (dd, J = 17.0, 10.2 Hz, 1H), 6.24 (dd, J = 16.9, 2.0 Hz, 1H), 5.74 (dd, J = 10.2, 2.0 Hz, 1H), 4.68-4.60 (m, 1H), 3.71 (d, J = 12.3 Hz, 2H), 3.58 (t, J = 4.6 Hz, 4H), 3.34 (br, 4H), 2.72 (t, J = 12.3 Hz, 2H), 2.31 (s, 1H), 1.88 (d, J = 12.3 Hz, 2H), 1.52 (t, J = 11.2 Hz, 2H), 1.28 (d, J = 6.0 Hz, 6H). MS: 583 $[M + H]^+$ |
| Example 6. | 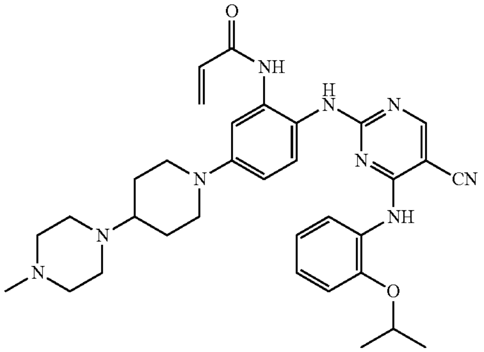 [SMILES: C=CC(=O)Nc1cc(N2CCC(N3CCN(C)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(4-methylpiperazin-1-yl)piperidin-1-yl)phenyl)acrylamide | $^1$H NMR (400 MHz, DMSO-$d_6$) δ 9.65 (s, 1H), 8.96 (s, 1H), 8.47 (s, 1H), 8.24 (s, 1H), 7.95 (s, 1H), 7.37-7.27 (m, 2H), 7.07 (t, J = 13.1 Hz, 2H), 6.80 (dd, J = 8.9, 2.8 Hz, 1H), 6.71 (s, 1H), 6.50 (dd, J = 16.9, 10.2 Hz, 1H), 6.24 (dd, J = 17.0, 2.1 Hz, 1H), 5.74 (dd, J = 10.1, 2.0 Hz, 1H), 4.64 (p, J = 6.1 Hz, 1H), 3.70 (d, J = 12.1 Hz, 2H), 3.35 (br, 4H), 2.71 (t, J = 12.1 Hz, 2H), 2.50 (br, 1H), 2.40-2.24 (m, 4H), 2.14 (s, 3H), 1.85 (d, J = 12.2 Hz, 2H), 1.51 (tt, J = 12.3, 6.2 Hz, 2H), 1.28 (d, J = 6.0 Hz, 6H). MS: 596 $[M + H]^+$ |
| Example 7. | 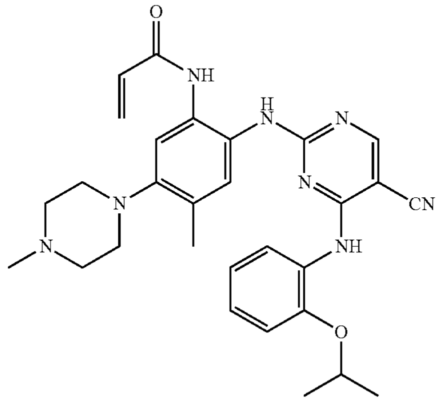 [SMILES: C=CC(=O)Nc1cc(N2CCN(C)CC2)c(C)cc1Nc1ncc(C#N)c(Nc2ccccc2OC(C)C)n1] | N-(2-((5-cyano-4-((2-isopropoxyphenyl)amino)pyrimidin-2-yl)amino)-4-methyl-5-(4-methylpiperazin-1-yl)phenyl)acrylamide | $^1$H NMR (400 MHz, DMSO-$d_6$) δ 9.80 (s, 1H), 9.03 (s, 1H), 8.48 (s, 1H), 8.30 (s, 1H), 7.99 (s, 1H), 7.38 (s, 1H), 7.31 (s, 1H), 7.08 (s, 2H), 6.75 (s, 1H), 6.50 (dd, J = 16.9, 10.2 Hz, 1H), 6.25 (dd, J = 17.0, 2.0 Hz, 1H), 5.75 (dd, J = 10.3, 1.9 Hz, 1H), 4.63 (p, J = 6.0 Hz, 1H), 2.85 (t, J = 4.7 Hz, 4H), 2.52 (br, 4H), 2.25 (s, 3H), 2.20 (s, 3H), 1.27 (d, J = 6.0 Hz, 6H). MS: 527 $[M + H]^+$ |

TABLE 3-continued

Structures, names and hydrogen NMR and mass spectrometry characterization data of the compounds prepared in Examples 2-81.

| No. | Structure | Name | Characterization |
|---|---|---|---|
| Example 8. | 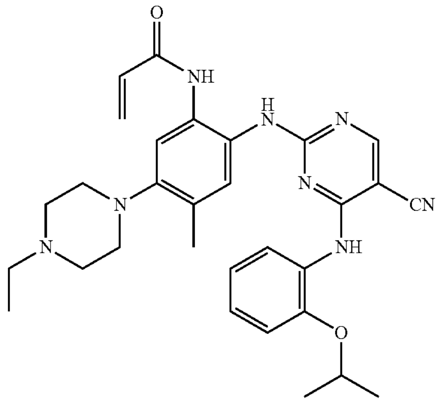 [SMILES: C=CC(=O)Nc1cc(N2CCN(CC)CC2)c(C)cc1Nc1ncc(C#N)c(Nc2ccccc2OC(C)C)n1] | N-(2-((5-cyano-4-((2-isopropoxyphenyl)amino)pyrimidin-2-yl)amino)-5-(4-ethylpiperazin-1-yl)-4-methylphenyl)acrylamide | $^1$H NMR (400 MHz, DMSO-$d_6$) δ 9.81 (s, 1H), 9.02 (s, 1H), 8.48 (s, 1H), 8.30 (s, 1H), 7.99 (s, 1H), 7.38 (s, 1H), 7.30 (s, 1H), 7.13-7.03 (m, 2H), 6.74 (s, 1H), 6.50 (dd, J = 16.9, 10.2 Hz, 1H), 6.25 (dd, J = 17.0, 2.0 Hz, 1H), 5.75 (dd, J = 10.2, 2.0 Hz, 1H), 4.63 (p, J = 6.0 Hz, 1H), 2.85 (t, J = 4.6 Hz, 4H), 2.55 (s, 4H), 2.41 (q, J = 7.1 Hz, 2H), 2.20 (s, 3H), 1.27 (d, J = 6.0 Hz, 6H), 1.05 (t, J = 7.2 Hz, 3H). MS: 541 $[M + H]^+$ |
| Example 9. | 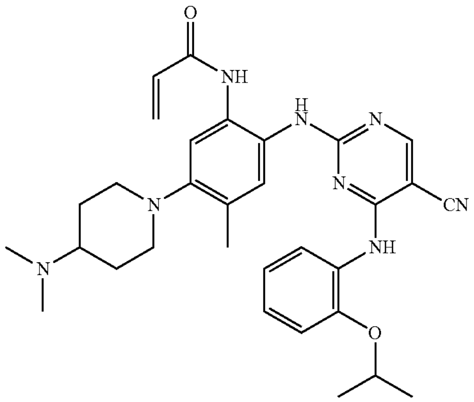 [SMILES: C=CC(=O)Nc1cc(N2CCC(N(C)C)CC2)c(C)cc1Nc1ncc(C#N)c(Nc2ccccc2OC(C)C)n1] | N-(2-((5-cyano-4-((2-isopropoxyphenyl)amino)pyrimidin-2-yl)amino)-5-(4-(dimethylamino)piperidin-1-yl)-4-methylphenyl)acrylamide | $^1$H NMR (400 MHz, DMSO-$d_6$) δ 9.76 (s, 1H), 9.02 (s, 1H), 8.48 (s, 1H), 8.30 (s, 1H), 7.99 (s, 1H), 7.35 (d, J = 16.0 Hz, 2H), 7.07 (d, J = 10.3 Hz, 2H), 6.74 (s, 1H), 6.49 (dd, J = 17.0, 10.2 Hz, 1H), 6.24 (dd, J = 16.9, 2.0 Hz, 1H), 5.75 (dd, J = 10.4, 2.1 Hz, 1H), 4.63 (p, J = 6.0 Hz, 1H), 3.12 (d, J = 11.5 Hz, 2H), 2.59-2.55 (m, 3H), 2.26 (s, 6H), 2.20 (s, 3H), 1.88 (d, J = 12.1 Hz, 2H), 1.58 (q, J = 11.2 Hz, 2H), 1.27 (d, J = 6.0 Hz, 6H). MS: 555 $[M + H]^+$ |
| Example 10. | 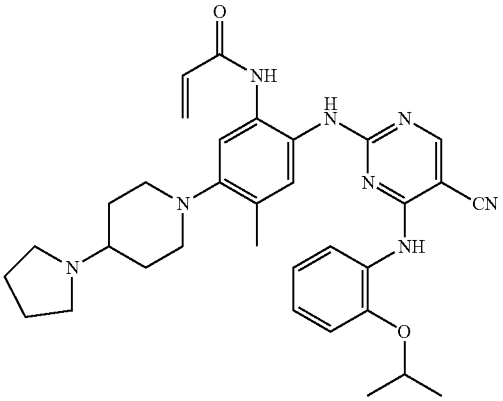 [SMILES: C=CC(=O)Nc1cc(N2CCC(N3CCCC3)CC2)c(C)cc1Nc1ncc(C#N)c(Nc2ccccc2OC(C)C)n1] | N-(2-((5-cyano-4-((2-isopropoxyphenyl)amino)pyrimidin-2-yl)amino)-4-methyl-5-(4-(pyrrolidin-1-yl)piperidin-1-yl)phenyl)acrylamide | $^1$H NMR (400 MHz, DMSO-$d_6$) δ 9.74 (s, 1H), 9.03 (s, 1H), 8.48 (s, 1H), 8.30 (s, 1H), 8.12-7.79 (m, 1H), 7.47-7.27 (m, 2H), 7.13-7.03 (m, 2H), 6.74 (s, 1H), 6.49 (dd, J = 17.0, 10.2 Hz, 1H), 6.24 (dd, J = 17.0, 2.1 Hz, 1H), 5.75 (dd, J = 10.1, 2.0 Hz, 1H), 4.64 (p, J = 6.1 Hz, 1H), 3.10 (d, J = 11.4 Hz, 2H), 2.72 (s, 4H), 2.66-2.55 (m, 3H), 2.20 (s, 3H), 2.00 (s, 2H), 1.76 (s, 4H), 1.64 (d, J = 10.2 Hz, 2H), 1.27 (d, J = 6.0 Hz, 6H). MS: 581 $[M + H]^+$ |

TABLE 3-continued

Structures, names and hydrogen NMR and mass spectrometry characterization data of the compounds prepared in Examples 2-81.

| No. | Structure | Name | Characterization |
|---|---|---|---|
| Example 11. | 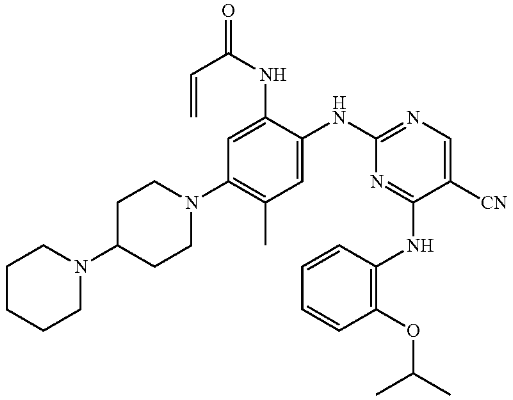 [SMILES: C=CC(=O)Nc1cc(N2CCC(N3CCCCC3)CC2)c(C)cc1Nc1ncc(C#N)c(Nc2ccccc2OC(C)C)n1] | N-(5-([1,4'-bipiperidin]-1'-yl)-2-((5-cyano-4-((2-isopropoxyphenyl)amino)pyrimidin-2-yl)amino)-4-methylphenyl)acrylamide | $^1$H NMR (400 MHz, DMSO-$d_6$) δ 9.74 (s, 1H), 9.03 (s, 1H), 8.48 (s, 1H), 8.29 (s, 1H), 7.99 (s, 1H), 7.42-7.31 (m, 2H), 7.15-7.06 (m, 2H), 6.74 (s, 1H), 6.49 (dd, J = 16.9, 10.1 Hz, 1H), 6.24 (dd, J = 17.0, 2.0 Hz, 1H), 5.78-5.70 (m, 1H), 4.67-4.58 (m, 1H), 3.13 (d, J = 11.3 Hz, 2H), 2.68-2.55 (m, 7H), 2.19 (s, 3H), 1.85 (s, 2H), 1.65 (d, J = 12.1 Hz, 2H), 1.54 (s, 4H), 1.42 (s, 2H), 1.27 (d, J = 6.0 Hz, 6H). MS: 595 [M + H]$^+$ |
| Example 12. | 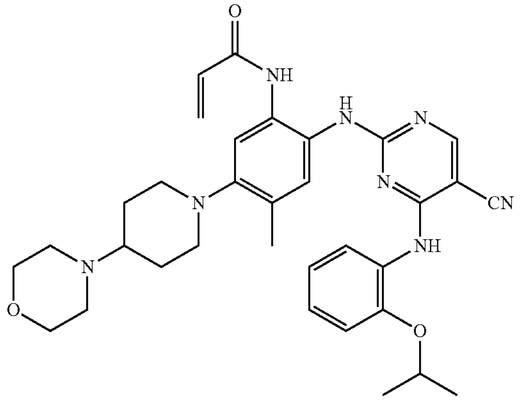 [SMILES: C=CC(=O)Nc1cc(N2CCC(N3CCOCC3)CC2)c(C)cc1Nc1ncc(C#N)c(Nc2ccccc2OC(C)C)n1] | N-(2-((5-cyano-4-((2-isopropoxyphenyl)amino)pyrimidin-2-yl)amino)-4-methyl-5-(4-morpholinopiperidin-1-yl)phenyl)acrylamide | $^1$H NMR (400 MHz, DMSO-$d_6$) δ 9.75 (s, 1H), 9.03 (s, 1H), 8.48 (s, 1H), 8.30 (s, 1H), 7.99 (s, 1H), 7.35 (d, J = 14.1 Hz, 2H), 7.13-7.03 (m, 2H), 6.74 (s, 1H), 6.49 (dd, J = 16.9, 10.2 Hz, 1H), 6.24 (dd, J = 17.0, 2.0 Hz, 1H), 5.74 (dd, J = 10.4, 2.1 Hz, 1H), 4.63 (p, J = 6.1 Hz, 1H), 3.63-3.56 (m, 4H), 3.36 (s, 4H), 3.12 (d, J = 11.4 Hz, 2H), 2.58 (t, J = 11.5 Hz, 2H), 2.35-2.23 (m, 1H), 2.19 (s, 3H), 1.90 (d, J = 11.8 Hz, 2H), 1.58 (d, J = 11.0 Hz, 2H), 1.27 (d, J = 6.0 Hz, 6H). MS: 597 [M + H]$^+$ |
| Example 13. | 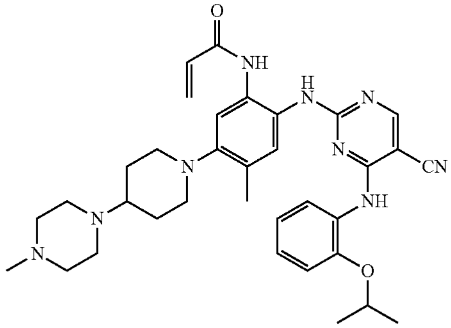 [SMILES: C=CC(=O)Nc1cc(N2CCC(N3CCN(C)CC3)CC2)c(C)cc1Nc1ncc(C#N)c(Nc2ccccc2OC(C)C)n1] | N-(2-((5-cyano-4-((2-isopropoxyphenyl)amino)pyrimidin-2-yl)amino)-4-methyl-5-(4-(4-methylpiperazin-1-yl)piperidin-1-yl)phenyl)acrylamide | $^1$H NMR (400 MHz, DMSO-$d_6$) δ 9.75 (s, 1H), 9.02 (s, 1H), 8.48 (s, 1H), 8.29 (s, 1H), 7.98 (s, 1H), 7.34 (d, J = 15.4 Hz, 2H), 7.08 (t, J = 9.5 Hz, 2H), 6.73 (s, 1H), 6.49 (dd, J = 17.0, 10.2 Hz, 1H), 6.24 (dd, J = 17.0, 2.1 Hz, 1H), 5.78-5.70 (m, 1H), 4.63 (p, J = 6.1 Hz, 1H), 3.39 (s, 4H), 3.12 (d, J = 11.4 Hz, 2H), 2.67-2.55 (m, 3H), 2.33 (d, J = 10.4 Hz, 4H), 2.19 (s, 3H), 2.16 (s, 3H), 1.87 (d, J = 12.1 Hz, 2H), 1.59 (d, J = 10.7 Hz, 2H), 1.27 (d, J = 6.0 Hz, 6H). MS: 610 [M + H]$^+$ |
| Example 14. | 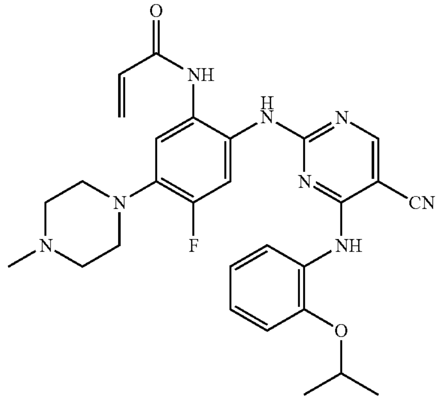 [SMILES: C=CC(=O)Nc1cc(N2CCN(C)CC2)c(F)cc1Nc1ncc(C#N)c(Nc2ccccc2OC(C)C)n1] | N-(2-((5-cyano-4-((2-isopropoxyphenyl)amino)pyrimidin-2-yl)amino)-4-fluoro-5-(4-methylpiperazin-1-yl)phenyl)acrylamide | $^1$H NMR (400 MHz, DMSO-$d_6$) δ 9.79 (s, 1H), 9.06 (s, 1H), 8.47 (d, J = 17.9 Hz, 2H), 7.92 (s, 1H), 7.43 (d, J = 14.2 Hz, 1H), 7.26 (d, J = 9.1 Hz, 1H), 7.10 (d, J = 4.3 Hz, 2H), 6.81 (s, 1H), 6.48 (dd, J = 17.0, 10.2 Hz, 1H), 6.25 (dd, J = 17.0, 2.0 Hz, 1H), 5.77 (dd, J = 10.1, 2.0 Hz, 1H), 4.63 (p, J = 6.0 Hz, 1H), 3.00 (t, J = 4.7 Hz, 4H), 2.50-2.45 (m, 4H), 2.24 (s, 3H), 1.26 (d, J = 6.0 Hz, 6H). MS: 531 [M + H]$^+$ |

TABLE 3-continued

Structures, names and hydrogen NMR and mass spectrometry characterization data of the compounds prepared in Examples 2-81.

| No. | Structure | Name | Characterization |
| --- | --- | --- | --- |
| Example 15. | 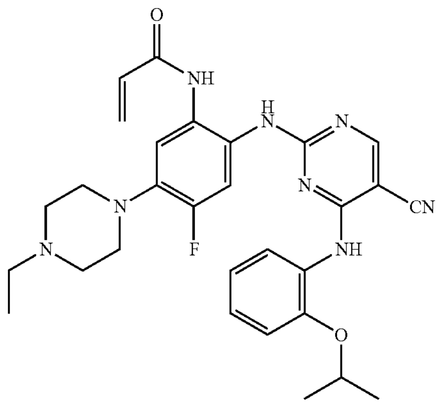 [SMILES: C=CC(=O)Nc1cc(N2CCN(CC)CC2)c(F)cc1Nc1ncc(C#N)c(Nc2ccccc2OC(C)C)n1] | N-(2-((5-cyano-4-((2-isopropoxyphenyl)amino)pyrimidin-2-yl)amino)-5-(4-ethylpiperazin-1-yl)-4-fluorophenyl)acrylamide | $^1$H NMR (400 MHz, DMSO-$d_6$) δ 9.80 (s, 1H), 9.06 (s, 1H), 8.47 (d, J = 18.2 Hz, 2H), 7.92 (s, 1H), 7.43 (d, J = 14.1 Hz, 1H), 7.25 (d, J = 9.1 Hz, 1H), 7.10 (d, J = 4.3 Hz, 2H), 6.81 (s, 1H), 6.48 (dd, J = 17.0, 10.1 Hz, 1H), 6.26 (dd, J = 17.0, 2.0 Hz, 1H), 5.77 (dd, J = 10.1, 2.0 Hz, 1H), 4.63 (p, J = 6.0 Hz, 1H), 3.01 (t, J = 4.7 Hz, 4H), 2.64-2.55 (m, 4H), 2.39 (q, J = 7.2 Hz, 2H), 1.26 (d, J = 6.0 Hz, 6H), 1.04 (t, J = 7.2 Hz, 3H). MS: 545 $[M + H]^+$ |
| Example 16. | 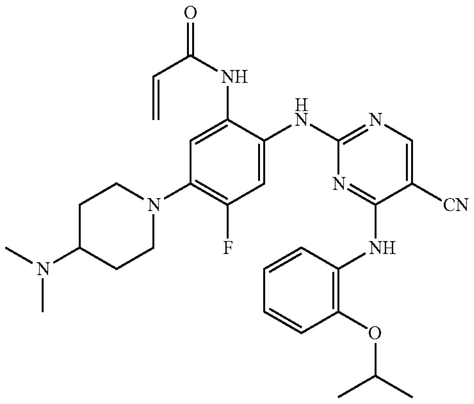 [SMILES: C=CC(=O)Nc1cc(N2CCC(N(C)C)CC2)c(F)cc1Nc1ncc(C#N)c(Nc2ccccc2OC(C)C)n1] | N-(2-((5-cyano-4-((2-isopropoxyphenyl)amino)pyrimidin-2-yl)amino)-5-(4-(dimethylamino)piperidin-1-yl)-4-fluorophenyl)acrylamide | $^1$H NMR (400 MHz, DMSO-$d_6$) δ 9.77 (s, 1H), 9.06 (s, 1H), 8.47 (d, J = 18.3 Hz, 2H), 7.92 (s, 1H), 7.42 (d, J = 14.0 Hz, 1H), 7.29 (d, J = 9.2 Hz, 1H), 7.10 (d, J = 4.3 Hz, 2H), 6.81 (s, 1H), 6.48 (dd, J = 17.0, 10.1 Hz, 1H), 6.25 (dd, J = 17.0, 2.0 Hz, 1H), 5.76 (dd, J = 10.1, 2.0 Hz, 1H), 4.63 (p, J = 6.0 Hz, 1H), 3.48-3.38 (m, 2H), 2.65 (td, J = 11.7, 2.1 Hz, 2H), 2.33-2.30 (m, 1H), 2.27 (s, 6H), 1.89 (d, J = 10.9 Hz, 2H), 1.58 (qd, J = 12.0, 3.8 Hz, 2H), 1.26 (d, J = 6.0 Hz, 6H). MS: 559 $[M + H]^+$ |
| Example 17. | 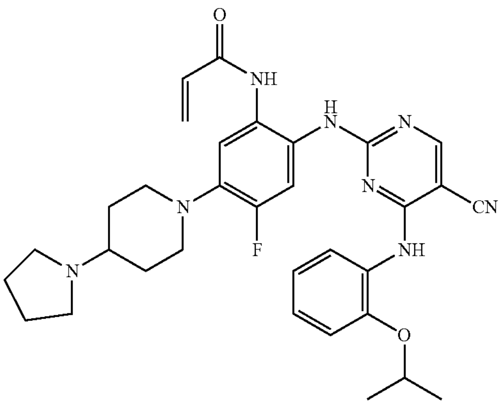 [SMILES: C=CC(=O)Nc1cc(N2CCC(N3CCCC3)CC2)c(F)cc1Nc1ncc(C#N)c(Nc2ccccc2OC(C)C)n1] | N-(2-((5-cyano-4-((2-isopropoxyphenyl)amino)pyrimidin-2-yl)amino)-4-fluoro-5-(4-(pyrrolidin-1-yl)piperidin-1-yl)phenyl)acrylamide | $^1$H NMR (400 MHz, DMSO-$d_6$) δ 9.77 (s, 1H), 9.08 (s, 1H), 8.48 (d, J = 18.6 Hz, 2H), 7.92 (s, 1H), 7.42 (d, J = 14.1 Hz, 1H), 7.31 (d, J = 9.1 Hz, 1H), 7.10 (d, J = 4.2 Hz, 2H), 6.81 (s, 1H), 6.48 (dd, J = 17.0, 10.1 Hz, 1H), 6.25 (dd, J = 16.9, 1.9 Hz, 1H), 5.77 (dd, J = 10.1, 2.0 Hz, 1H), 4.63 (p, J = 6.0 Hz, 1H), 3.38 (s, 4H), 2.88-2.63 (m, 5H), 2.03 (d, J = 12.2 Hz, 2H), 1.78 (s, 4H), 1.65 (d, J = 12.1 Hz, 2H), 1.26 (d, J = 6.0 Hz, 6H). MS: 585 $[M + H]^+$ |

TABLE 3-continued

| Structures, names and hydrogen NMR and mass spectrometry characterization data of the compounds prepared in Examples 2-81. | | | |
|---|---|---|---|
| No. | Structure | Name | Characterization |
| Example 18. | 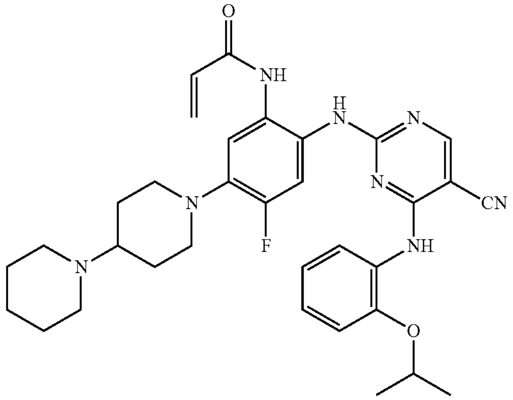 [SMILES: C=CC(=O)Nc1cc(N2CCC(N3CCCCC3)CC2)c(F)cc1Nc1ncc(C#N)c(Nc2ccccc2OC(C)C)n1] | N-(5-([1,4'-bipiperidin]-1'-yl)-2-((5-cyano-4-((2-isopropoxyphenyl)amino)pyrimidin-2-yl)amino)-4-fluorophenyl)acrylamide | $^1$H NMR (400 MHz, DMSO-$d_6$) δ 9.76 (s, 1H), 9.07 (s, 1H), 8.47 (d, J = 19.8 Hz, 2H), 7.92 (s, 1H), 7.41 (d, J = 14.0 Hz, 1H), 7.28 (d, J = 9.2 Hz, 1H), 7.10 (d, J = 4.3 Hz, 2H), 6.81 (s, 1H), 6.48 (dd, J = 17.0, 10.1 Hz, 1H), 6.25 (dd, J = 17.0, 2.0 Hz, 1H), 5.76 (dd, J = 10.1, 2.0 Hz, 1H), 4.63 (p, J = 6.1 Hz, 1H), 3.39 (br, 4H), 2.70-2.59 (m, 2H), 2.48 (d, J = 4.4 Hz, 2H), 2.35 (s, 1H), 1.82 (d, J = 12.0 Hz, 2H), 1.63 (dd, J = 12.6, 9.0 Hz, 2H), 1.62-1.45 (m, 4H), 1.44-1.36 (m, 2H), 1.26 (d, J = 6.0 Hz, 6H). MS: 599 [M + H]$^+$ |
| Example 19. | 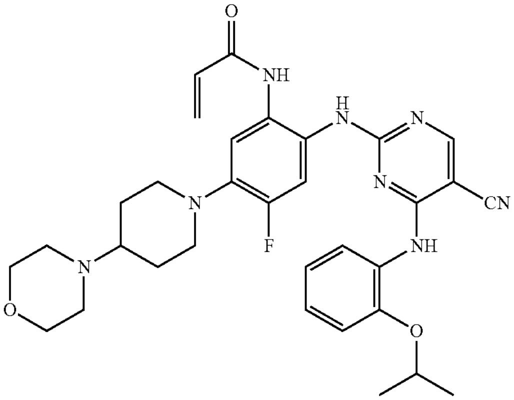 [SMILES: C=CC(=O)Nc1cc(N2CCC(N3CCOCC3)CC2)c(F)cc1Nc1ncc(C#N)c(Nc2ccccc2OC(C)C)n1] | N-(2-((5-cyano-4-((2-isopropoxyphenyl)amino)pyrimidin-2-yl)amino)-4-fluoro-5-(4-morpholinopiperidin-1-yl)phenyl)acrylamide | $^1$H NMR (400 MHz, DMSO-$d_6$) δ 9.77 (s, 1H), 9.07 (s, 1H), 8.47 (d, J = 19.7 Hz, 2H), 7.91 (s, 1H), 7.41 (d, J = 14.0 Hz, 1H), 7.29 (d, J = 9.2 Hz, 1H), 7.10 (d, J = 4.2 Hz, 2H), 6.81 (s, 1H), 6.48 (dd, J = 16.9, 10.2 Hz, 1H), 6.25 (dd, J = 17.0, 2.0 Hz, 1H), 5.76 (dd, J = 10.1, 2.0 Hz, 1H), 4.63 (p, J = 6.0 Hz, 1H), 3.59 (t, J = 4.5 Hz, 4H), 3.45-2.35 (m, 6H), 2.71-2.61 (m, 2H), 2.31 (d, J = 13.1 Hz, 1H), 1.89 (d, J = 12.1 Hz, 2H), 1.57 (q, J = 11.1 Hz, 2H), 1.26 (d, J = 6.0 Hz, 6H). MS: 601 [M + H]$^+$ |
| Example 20. | 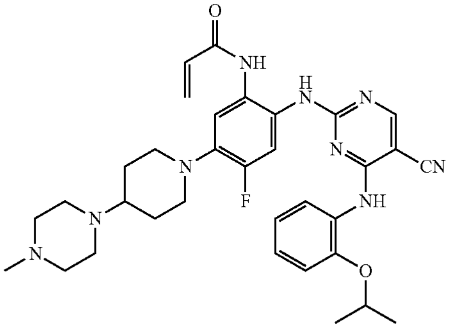 | N-(2-((5-cyano-4-((2-isopropoxyphenyl)amino)pyrimidin-2-yl)amino)-4-fluoro-5-(4-(4-methylpiperazin-1-yl)piperidin-1-yl)phenyl)acrylamide | $^1$H NMR (400 MHz, DMSO-$d_6$) δ 9.77 (s, 1H), 9.07 (s, 1H), 8.47 (d, J = 19.8 Hz, 2H), 7.92 (s, 1H), 7.41 (d, J = 14.0 Hz, 1H), 7.28 (d, J = 9.2 Hz, 1H), 7.10 (d, J = 4.2 Hz, 2H), 6.81 (s, 1H), 6.48 (dd, J = 17.0, 10.1 Hz, 1H), 6.25 (dd, J = 17.0, 2.0 Hz, 1H), 5.76 (dd, J = 10.1, 2.0 Hz, 1H), 4.63 (p, J = 6.0 Hz, 1H), 3.35 (br, 4H), 2.71-2.60 (m, 2H), 2.57 (br, 3H), 2.38-2.26 (m, 4H), 2.15 (s, 3H), 1.86 (d, J = 11.5 Hz, 2H), 1.58 (dt, J = 11.9, 5.9 Hz, 2H), 1.26 (d, J = 6.0 Hz, 6H). MS: 614 [M + H]$^+$ |
| Example 21. | 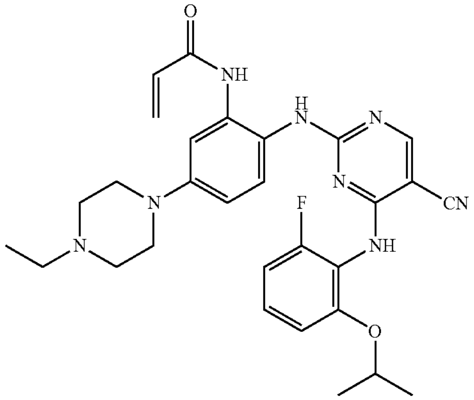 [SMILES: C=CC(=O)Nc1cc(N2CCN(CC)CC2)ccc1Nc1ncc(C#N)c(Nc2c(F)cccc2OC(C)C)n1] | N-(2-((5-cyano-4-((2-fluoro-6-isopropoxyphenyl)amino)pyrimidin-2-yl)amino)-5-(4-ethylpiperazin-1-yl)phenyl)acrylamide | $^1$H NMR (400 MHz, DMSO-$d_6$) δ 9.69 (s, 1H), 8.97 (s, 1H), 8.65 (s, 1H), 8.36 (s, 1H), 7.27 (td, J = 8.3, 6.7 Hz, 2H), 7.00 (s, 1H), 6.95-6.80 (m, 2H), 6.56 (s, 1H), 6.44 (dd, J = 17.0, 10.1 Hz, 1H), 6.28-6.18 (m, 1H), 5.80-5.72 (m, 1H), 4.54 (br, 1H), 3.07 (s, 4H), 2.50 (br, 4H), 2.40 (s, 2H), 1.16 (d, J = 6.0 Hz, 6H), 1.05 (t, J = 7.2 Hz, 3H). MS: 545 [M + H]$^+$ |

TABLE 3-continued

| Structures, names and hydrogen NMR and mass spectrometry characterization data of the compounds prepared in Examples 2-81. | | | |
|---|---|---|---|
| No. | Structure | Name | Characterization |
| Example 22. | 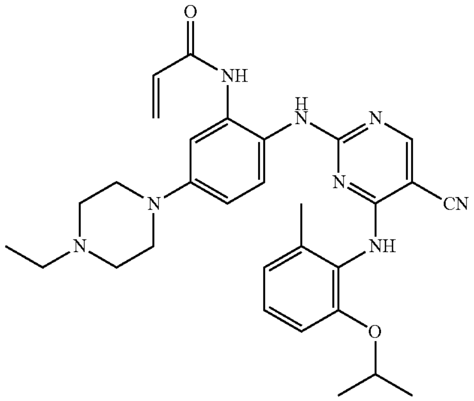 [SMILES: C=CC(=O)Nc1cc(N2CCN(CC)CC2)ccc1Nc1ncc(C#N)c(Nc2c(C)cccc2OC(C)C)n1] | N-(2-((5-cyano-4-((2-isopropoxy-6-methylphenyl)amino)pyrimidin-2-yl)amino)-5-(4-ethylpiperazin-1-yl)phenyl)acrylamide | $^1$H NMR (400 MHz, DMSO-$d_6$) δ 9.68 (s, 1H), 8.80 (s, 1H), 8.53 (s, 1H), 8.31 (s, 1H), 7.28 (d, J = 9.0 Hz, 1H), 7.15 (t, J = 7.9 Hz, 1H), 7.02 (s, 1H), 6.89 (d, J = 8.2 Hz, 1H), 6.80 (d, J = 7.6 Hz, 1H), 6.60 (s, 1H), 6.42 (dd, J = 17.0, 10.1 Hz, 1H), 6.22 (dd, J = 17.0, 2.0 Hz, 1H), 5.75 (dd, J = 9.9, 2.1 Hz, 1H), 4.51-4.43 (m, 1H), 3.06 (d, J = 6.3 Hz, 4H), 2.63-2.51 (m, 4H), 2.39 (d, J = 7.3 Hz, 2H), 2.14 (s, 3H), 1.13 (d, J = 6.0 Hz, 6H), 1.04 (t, J = 7.2 Hz, 3H). MS: 541 $[M + H]^+$ |
| Example 23. | 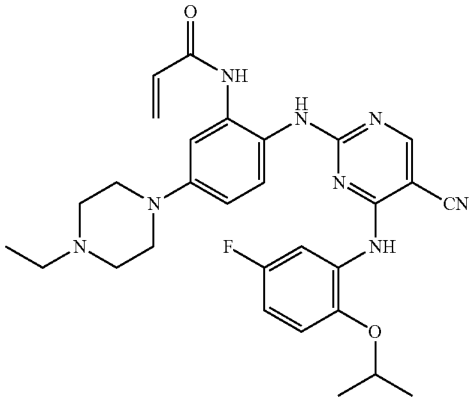 [SMILES: C=CC(=O)Nc1cc(N2CCN(CC)CC2)ccc1Nc1ncc(C#N)c(Nc2cc(F)ccc2OC(C)C)n1] | N-(2-((5-cyano-4-((5-fluoro-2-isopropoxyphenyl)amino)pyrimidin-2-yl)amino)-5-(4-ethylpiperazin-1-yl)phenyl)acrylamide | $^1$H NMR (400 MHz, DMSO-$d_6$) δ 9.69 (s, 1H), 8.54 (s, 1H), 8.18 (s, 1H), 7.36 (d, J = 28.3 Hz, 2H), 7.16 (d, J = 38.0 Hz, 2H), 6.83 (s, 2H), 6.51 (dd, J = 17.0, 10.1 Hz, 1H), 6.25 (dd, J = 17.0, 2.1 Hz, 1H), 5.75 (d, J = 10.4 Hz, 1H), 5.33 (t, J = 4.9 Hz, 1H), 4.61 (s, 1H), 3.13 (br, 4H), 2.00 (q, J = 7.0, 6.5 Hz, 4H), 1.47 (d, J = 8.3 Hz, 2H), 1.28 (d, J = 6.0 Hz, 6H), 0.90-0.81 (m, 3H). MS: 545 $[M + H]^+$ |
| Example 24. | 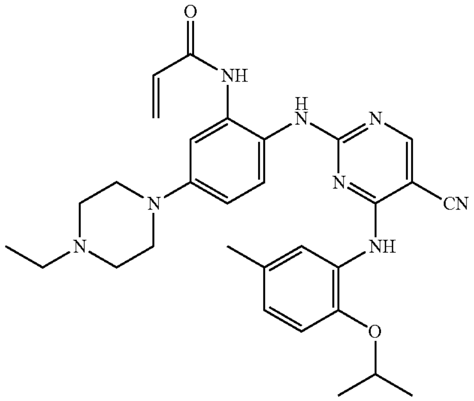 [SMILES: C=CC(=O)Nc1cc(N2CCN(CC)CC2)ccc1Nc1ncc(C#N)c(Nc2cc(C)ccc2OC(C)C)n1] | N-(2-((5-cyano-4-((2-isopropoxy-5-methylphenyl)amino)pyrimidin-2-yl)amino)-5-(4-ethylpiperazin-1-yl)phenyl)acrylamide | $^1$H NMR (400 MHz, DMSO-$d_6$) δ 9.64 (s, 1H), 8.99 (s, 1H), 8.52-8.47 (m, 1H), 8.13 (s, 1H), 7.83 (s, 1H), 7.36 (d, J = 8.7 Hz, 2H), 6.96 (d, J = 8.2 Hz, 1H), 6.87-6.76 (m, 2H), 6.51 (dd, J = 17.0, 10.1 Hz, 1H), 6.24 (dd, J = 16.9, 2.1 Hz, 1H), 5.74 (dd, J = 10.1, 2.0 Hz, 1H), 4.58 (p, J = 6.0 Hz, 1H), 3.18-3.10 (m, 4H), 2.52 (br, 4H), 2.38 (q, J = 7.2 Hz, 2H), 2.05-2.00 (m, 3H), 1.26 (d, J = 6.0 Hz, 6H), 1.05 (t, J = 7.1 Hz, 3H). MS: 541 $[M + H]^+$ |

TABLE 3-continued

| Structures, names and hydrogen NMR and mass spectrometry characterization data of the compounds prepared in Examples 2-81. | | | |
|---|---|---|---|
| No. | Structure | Name | Characterization |
| Example 25. | 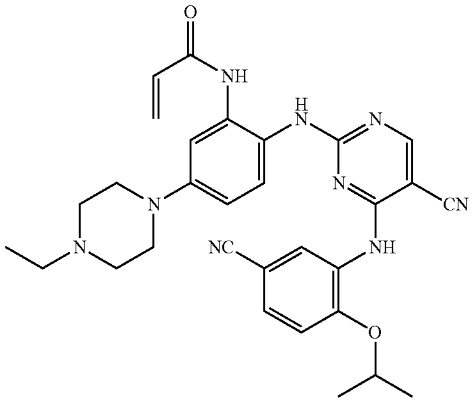 [SMILES: C=CC(=O)Nc1cc(N2CCN(CC)CC2)ccc1Nc1ncc(C#N)c(Nc2cc(C#N)ccc2OC(C)C)n1] | N-(2-((5-cyano-4-((5-cyano-2-isopropoxyphenyl)amino)pyrimidin-2-yl)amino)-5-(4-ethylpiperazin-1-yl)phenyl)acrylamide | $^1H$ NMR (400 MHz, DMSO-$d_6$) δ 9.73 (s, 1H), 9.08 (s, 1H), 8.51 (s, 1H), 8.36 (s, 1H), 8.26 (s, 1H), 7.55 (s, 1H), 7.44 (s, 1H), 7.27 (d, J = 8.7 Hz, 2H), 6.83 (s, 1H), 6.49 (dd, J = 16.9, 10.4 Hz, 1H), 6.25 (dd, J = 17.0, 2.0 Hz, 1H), 5.79-5.71 (m, 1H), 4.81 (s, 1H), 3.17 (s, 4H), 2.56 (s, 4H), 2.43 (s, 2H), 1.30 (d, J = 6.0 Hz, 6H), 1.06 (t, J = 7.2 Hz, 3H). MS: 552 $[M + H]^+$ |
| Example 26. | 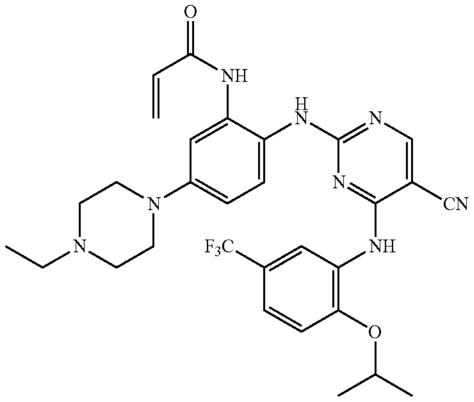 [SMILES: C=CC(=O)Nc1cc(N2CCN(CC)CC2)ccc1Nc1ncc(C#N)c(Nc2cc(C(F)(F)F)ccc2OC(C)C)n1] | N-(2-((5-cyano-4-((2-isopropoxy-5-(trifluoromethyl)phenyl)amino)pyrimidin-2-yl)amino)-5-(4-ethylpiperazin-1-yl)phenyl)acrylamide | $^1H$ NMR (400 MHz, DMSO-$d_6$) δ 9.72 (s, 1H), 8.98 (s, 1H), 8.49 (d, J = 9.4 Hz, 2H), 8.14 (s, 1H), 7.41 (s, 1H), 7.30 (dd, J = 20.6, 8.8 Hz, 2H), 7.17 (d, J = 2.7 Hz, 1H), 6.68 (s, 1H), 6.48 (dd, J = 17.0, 10.1 Hz, 1H), 6.25 (dd, J = 17.0, 2.0 Hz, 1H), 5.75 (dd, J = 10.0, 2.1 Hz, 1H), 4.83-4.73 (m, 1H), 3.11 (t, J = 4.9 Hz, 4H), 2.55-2.45 (m, 4H), 2.39 (t, J = 7.2 Hz, 2H), 1.30 (d, J = 6.0 Hz, 6H), 1.04 (t, J = 7.2 Hz, 3H). MS: 595 $[M + H]^+$ |
| Example 27. | 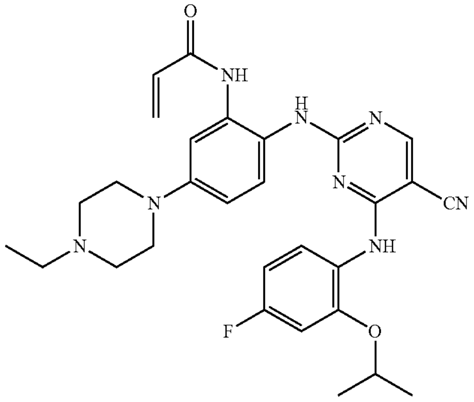 [SMILES: C=CC(=O)Nc1cc(N2CCN(CC)CC2)ccc1Nc1ncc(C#N)c(Nc2ccc(F)cc2OC(C)C)n1] | N-(2-((5-cyano-4-((4-fluoro-2-isopropoxyphenyl)amino)pyrimidin-2-yl)amino)-5-(4-ethylpiperazin-1-yl)phenyl)acrylamide | $^1H$ NMR (400 MHz, DMSO-$d_6$) δ 9.64 (s, 1H), 8.87 (s, 1H), 8.42 (s, 1H), 8.37 (s, 1H), 7.73 (s, 1H), 7.31 (d, J = 8.7 Hz, 1H), 7.22 (s, 1H), 7.07-7.00 (m, 1H), 6.77 (dd, J = 9.0, 2.8 Hz, 1H), 6.62 (s, 1H), 6.48 (dd, J = 17.0, 10.1 Hz, 1H), 6.23 (dd, J = 17.0, 2.0 Hz, 1H), 5.74 (dd, J = 10.4, 2.2 Hz, 1H), 4.69-4.61 (m, 1H), 3.13 (t, J = 5.0 Hz, 4H), 2.53 (s, 4H), 2.38 (q, J = 7.1 Hz, 2H), 1.23 (d, J = 5.9 Hz, 6H), 1.05 (t, J = 7.2 Hz, 3H). MS: 545 $[M + H]^+$ |

TABLE 3-continued

Structures, names and hydrogen NMR and mass spectrometry characterization data of the compounds prepared in Examples 2-81.

| No. | Structure | Name | Characterization |
|---|---|---|---|
| Example 28. | 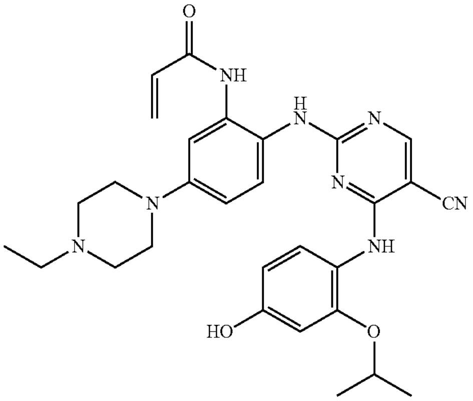 | N-(2-((5-cyano-4-((4-hydroxy-2-isopropoxyphenyl)amino)pyrimidin-2-yl)amino)-5-(4-ethylpiperazin-1-yl)phenyl)acrylamide | $^1$H NMR (400 MHz, DMSO-$d_6$) δ 9.67 (s, 1H), 9.36 (s, 1H), 8.78 (s, 1H), 8.37 (s, 1H), 8.23 (s, 1H), 7.54 (s, 1H), 7.35 (s, 1H), 7.21 (s, 1H), 6.76 (d, J = 8.9 Hz, 1H), 6.54-6.42 (m, 2H), 6.28-6.20 (m, 2H), 5.79-5.71 (m, 1H), 4.60-4.38 (m, 1H), 3.13 (s, 4H), 2.50 (br, 4H), 2.40 (s, 2H), 1.22 (d, J = 6.0 Hz, 6H), 1.05 (t, J = 7.1 Hz, 3H). MS: 543 [M + H]$^+$ |
| Example 29. | 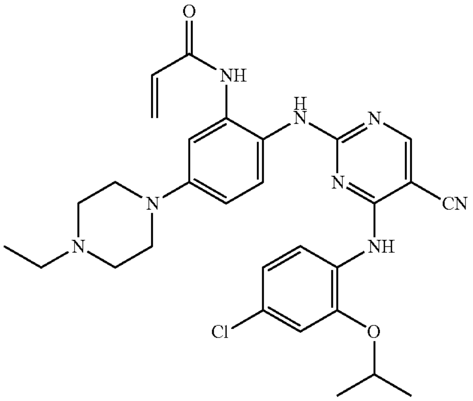 [SMILES: C=CC(=O)Nc1cc(N2CCN(CC)CC2)ccc1Nc1ncc(C#N)c(Nc2ccc(Cl)cc2OC(C)C)n1] | N-(2-((4-((4-chloro-2-isopropoxyphenyl)amino)-5-cyanopyrimidin-2-yl)amino)-5-(4-ethylpiperazin-1-yl)phenyl)acrylamide | $^1$H NMR (400 MHz, DMSO-$d_6$) δ 9.67 (s, 1H), 8.96 (s, 1H), 8.46 (s, 1H), 8.32 (s, 1H), 7.78 (s, 1H), 7.34-7.24 (m, 2H), 7.18 (s, 1H), 6.79 (dd, J = 8.9, 2.8 Hz, 1H), 6.73 (s, 1H), 6.49 (dd, J = 17.0, 10.1 Hz, 1H), 6.24 (dd, J = 17.0, 2.1 Hz, 1H), 5.74 (dd, J = 10.0, 2.1 Hz, 1H), 4.69 (d, J = 8.3 Hz, 1H), 3.15 (t, J = 4.8 Hz, 4H), 2.58-2.51 (m, 4H), 2.40 (d, J = 7.2 Hz, 2H), 1.25 (d, J = 6.2 Hz, 6H), 1.05 (t, J = 7.2 Hz, 3H). MS: 561 [M + H]$^+$ |
| Example 30. | 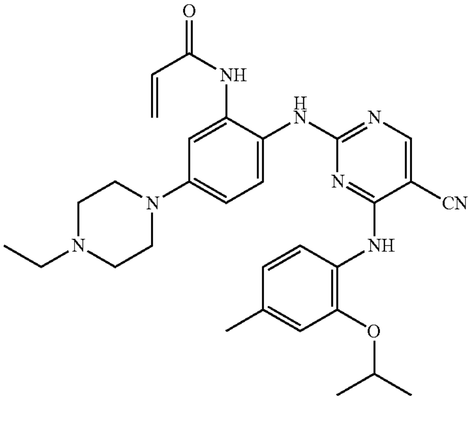 [SMILES: C=CC(=O)Nc1cc(N2CCN(CC)CC2)ccc1Nc1ncc(C#N)c(Nc2ccc(C)cc2OC(C)C)n1] | N-(2-((5-cyano-4-((2-isopropoxy-4-methylphenyl)amino)pyrimidin-2-yl)amino)-5-(4-ethylpiperazin-1-yl)phenyl)acrylamide | $^1$H NMR (400 MHz, DMSO-$d_6$) δ 9.67 (s, 1H), 8.90 (s, 1H), 8.43 (s, 1H), 8.22 (s, 1H), 7.74 (s, 1H), 7.35 (s, 1H), 7.27 (s, 1H), 6.92 (s, 1H), 6.79 (dd, J = 8.9, 2.8 Hz, 1H), 6.64-6.40 (m, 2H), 6.24 (dd, J = 17.0, 2.1 Hz, 1H), 5.74 (dd, J = 10.1, 2.1 Hz, 1H), 4.65-4.57 (m, 1H), 3.15 (s, 4H), 2.54 (s, 4H), 2.41 (s, 2H), 2.27 (s, 3H), 1.26 (d, J = 6.0 Hz, 6H), 1.06 (t, J = 7.1 Hz, 3H). MS: 541 [M + H]$^+$ |

TABLE 3-continued

| Structures, names and hydrogen NMR and mass spectrometry characterization data of the compounds prepared in Examples 2-81. | | | |
|---|---|---|---|
| No. | Structure | Name | Characterization |
| Example 31. | 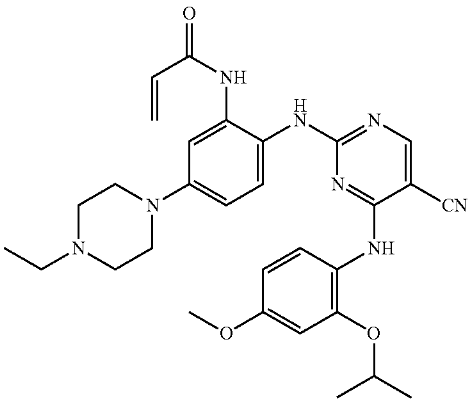 [SMILES: C=CC(=O)Nc1cc(N2CCN(CC)CC2)ccc1Nc1ncc(C#N)c(Nc2ccc(OC)cc2OC(C)C)n1] | N-(2-((5-cyano-4-((2-isopropoxy-4-methoxyphenyl)amino)pyrimidin-2-yl)amino)-5-(4-ethylpiperazin-1-yl)phenyl)acrylamide | $^{1}$H NMR (400 MHz, DMSO-$d_6$) δ 9.67 (s, 1H), 8.79 (s, 1H), 8.39 (s, 1H), 8.28 (s, 1H), 7.64 (s, 1H), 7.34 (s, 1H), 7.20 (s, 1H), 6.77 (dd, J = 9.0, 2.8 Hz, 1H), 6.65 (d, J = 2.7 Hz, 1H), 6.48 (dd, J = 17.0, 10.2 Hz, 1H), 6.34 (s, 1H), 6.24 (dd, J = 17.0, 2.0 Hz, 1H), 5.79-5.71 (m, 1H), 4.61 (p, J = 6.0 Hz, 1H), 3.74 (s, 3H), 3.13 (t, J = 5.0 Hz, 4H), 2.53 (s, 4H), 2.43-2.35 (m, 2H), 1.23 (d, J = 6.0 Hz, 6H), 1.05 (t, J = 7.2 Hz, 3H). MS: 557 [M + H]$^+$ |
| Example 32. | 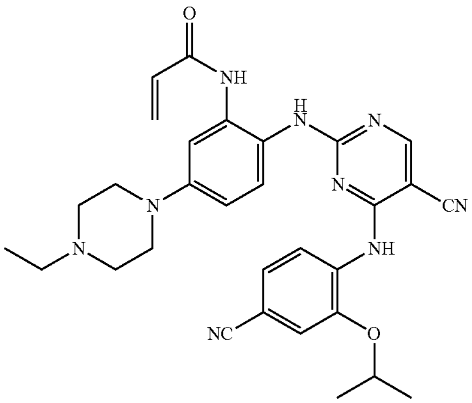 [SMILES: C=CC(=O)Nc1cc(N2CCN(CC)CC2)ccc1Nc1ncc(C#N)c(Nc2ccc(C#N)cc2OC(C)C)n1] | N-(2-((5-cyano-4-((4-cyano-2-isopropoxyphenyl)amino)pyrimidin-2-yl)amino)-5-(4-ethylpiperazin-1-yl)phenyl)acrylamide | $^{1}$H NMR (400 MHz, DMSO-$d_6$) δ 9.68 (s, 1H), 9.15 (s, 1H), 8.56 (s, 1H), 8.36 (s, 1H), 8.09 (s, 1H), 7.60 (s, 1H), 7.34 (s, 2H), 7.10 (s, 1H), 6.87 (s, 1H), 6.50 (dd, J = 16.9, 10.1 Hz, 1H), 6.23 (dd, J = 16.9, 2.0 Hz, 1H), 5.74 (dd, J = 10.1, 2.0 Hz, 1H), 4.80 (s, 1H), 3.19 (s, 4H), 2.67 (t, J = 1.8 Hz, 4H), 2.45-2.35 (m, 2H), 1.30 (d, J = 6.0 Hz, 6H), 1.07 (s, 3H). MS: 552 [M + H]$^+$ |
| Example 33. | 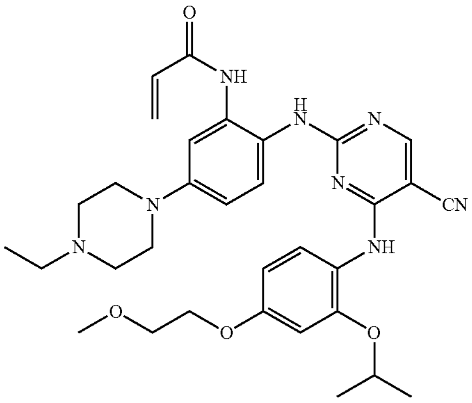 [SMILES: C=CC(=O)Nc1cc(N2CCN(CC)CC2)ccc1Nc1ncc(C#N)c(Nc2ccc(OCCOC)cc2OC(C)C)n1] | N-(2-((5-cyano-4-((2-isopropoxy-4-(2-methoxyethoxy)phenyl)amino)pyrimidin-2-yl)amino)-5-(4-ethylpiperazin-1-yl)phenyl)acrylamide | $^{1}$H NMR (400 MHz, DMSO-$d_6$) δ 9.67 (s, 1H), 8.79 (s, 1H), 8.39 (s, 1H), 8.31 (s, 1H), 7.59 (s, 1H), 7.34 (s, 1H), 7.19 (s, 1H), 6.76 (dd, J = 9.0, 2.8 Hz, 1H), 6.67 (d, J = 2.6 Hz, 1H), 6.48 (dd, J = 16.9, 10.1 Hz, 1H), 6.35 (s, 1H), 6.24 (dd, J = 17.0, 2.0 Hz, 1H), 5.79-5.71 (m, 1H), 4.65-4.57 (m, 1H), 4.07 (t, J = 4.5 Hz, 2H), 3.69-3.62 (m, 2H), 3.32 (s, 3H), 3.12 (t, J = 5.1 Hz, 4H), 2.53 (s, 4H), 2.38 (q, J = 7.1 Hz, 2H), 1.22 (d, J = 6.0 Hz, 6H), 1.05 (t, J = 7.1 Hz, 3H). MS: 601 [M + H]$^+$ |

TABLE 3-continued

Structures, names and hydrogen NMR and mass spectrometry characterization data of the compounds prepared in Examples 2-81.

| No. | Structure | Name | Characterization |
|---|---|---|---|
| Example 34. | 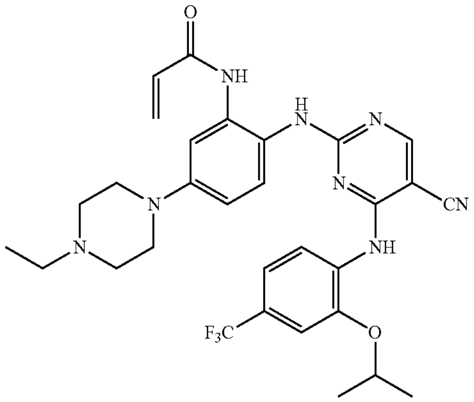 [SMILES: C=CC(=O)Nc1cc(N2CCN(CC)CC2)ccc1Nc1ncc(C#N)c(Nc2ccc(C(F)(F)F)cc2OC(C)C)n1] | N-(2-((5-cyano-4-((2-isopropoxy-4-(trifluoromethyl)phenyl)amino)pyrimidin-2-yl)amino)-5-(4-ethylpiperazin-1-yl)phenyl)acrylamide | $^1$H NMR (400 MHz, DMSO-$d_6$) δ 9.66 (s, 1H), 9.07 (s, 1H), 8.53 (s, 1H), 8.36 (s, 1H), 8.02 (s, 1H), 7.49-7.22 (m, 3H), 6.98 (s, 1H), 6.82 (d, J = 9.0 Hz, 1H), 6.50 (dd, J = 17.1, 10.3 Hz, 1H), 6.23 (dd, J = 17.0, 2.0 Hz, 1H), 5.73 (dd, J = 10.1, 2.0 Hz, 1H), 4.81 (s, 1H), 3.15 (s, 4H), 2.51 (t, J = 1.8 Hz, 4H), 2.38 (q, J = 7.1 Hz, 2H), 1.28 (d, J = 6.0 Hz, 6H), 1.05 (t, J = 7.1 Hz, 3H). MS: 595 $[M + H]^+$ |
| Example 35. | 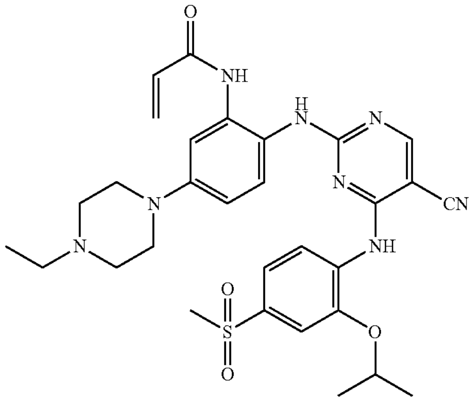 [SMILES: C=CC(=O)Nc1cc(N2CCN(CC)CC2)ccc1Nc1ncc(C#N)c(Nc2ccc(S(C)(=O)=O)cc2OC(C)C)n1] | N-(2-((5-cyano-4-((2-isopropoxy-4-(methylsulfonyl)phenyl)amino)pyrimidin-2-yl)amino)-5-(4-ethylpiperazin-1-yl)phenyl)acrylamide | $^1$H NMR (400 MHz, DMSO-$d_6$) δ 9.68 (s, 1H), 9.12 (s, 1H), 8.56 (s, 1H), 8.38 (s, 1H), 8.10 (s, 1H), 7.54 (s, 1H), 7.33 (s, 2H), 7.20 (s, 1H), 6.85 (s, 1H), 6.50 (dd, J = 17.0, 10.2 Hz, 1H), 6.23 (dd, J = 17.0, 2.0 Hz, 1H), 5.79-5.70 (m, 1H), 4.82 (s, 1H), 3.21-3.16 (m, 7H), 2.58 (br, 4H), 2.40 (s, 2H), 1.32 (d, J = 6.0 Hz, 6H), 1.05 (t, J = 7.1 Hz, 3H). MS: 605 $[M + H]^+$ |
| Example 36. | 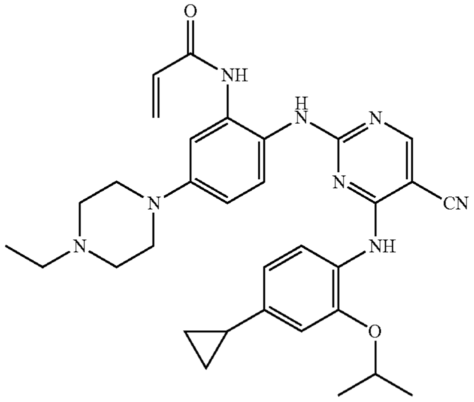 [SMILES: C=CC(=O)Nc1cc(N2CCN(CC)CC2)ccc1Nc1ncc(C#N)c(Nc2ccc(C3CC3)cc2OC(C)C)n1] | N-(2-((5-cyano-4-((4-cyclopropyl-2-isopropoxyphenyl)amino)pyrimidin-2-yl)amino)-5-(4-ethylpiperazin-1-yl)phenyl)acrylamide | $^1$H NMR (400 MHz, DMSO-$d_6$) δ 9.67 (s, 1H), 8.87 (s, 1H), 8.43 (s, 1H), 8.22 (s, 1H), 7.67 (s, 1H), 7.33 (s, 1H), 7.24 (s, 1H), 6.78 (dt, J = 6.1, 3.1 Hz, 2H), 6.49 (dd, J = 16.9, 10.1 Hz, 1H), 6.41 (s, 1H), 6.24 (dd, J = 17.0, 2.0 Hz, 1H), 5.74 (dd, J = 10.1, 2.1 Hz, 1H), 4.67-4.59 (m, 1H), 3.15 (t, J = 5.0 Hz, 4H), 2.54 (d, J = 5.3 Hz, 4H), 2.39 (q, J = 7.2 Hz, 2H), 1.92-1.84 (m, 1H), 1.24 (d, J = 5.9 Hz, 6H), 1.05 (t, J = 7.2 Hz, 3H), 0.98-0.88 (m, 2H), 0.64 (d, J = 5.2 Hz, 2H). MS: 567 $[M + H]^+$ |

TABLE 3-continued

Structures, names and hydrogen NMR and mass spectrometry characterization data of the compounds prepared in Examples 2-81.

| No. | Structure | Name | Characterization |
|---|---|---|---|
| Example 37. | 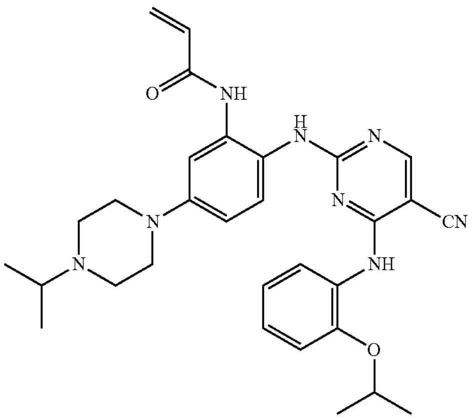 [SMILES: C=CC(=O)Nc1cc(N2CCN(C(C)C)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-isopropylpiperazin-1-yl)phenyl) acrylamide | $^1$H NMR (400 MHz, DMSO-$d_6$) δ 9.69 (s, 1H), 8.96 (s, 1H), 8.47 (s, 1H), 8.24 (s, 1H), 7.95 (s, 1H), 7.37 (s, 1H), 7.28 (s, 1H), 7.06 (d, J = 14.2 Hz, 2H), 6.81 (dd, J = 8.9, 2.8 Hz, 1H), 6.71 (s, 1H), 6.50 (dd, J = 17.0, 10.2 Hz, 1H), 6.24 (dd, J = 17.0, 2.0 Hz, 1H), 5.74 (dd, J = 10.1, 2.0 Hz, 1H), 4.64 (p, J = 6.2 Hz, 1H), 3.13 (d, J = 6.0 Hz, 4H), 2.72 (s, 1H), 2.63 (s, 4H), 1.28 (d, J = 6.0 Hz, 6H), 1.03 (d, J = 6.5 Hz, 6H). MS: 541 $[M + H]^+$ |
| Example 38. | 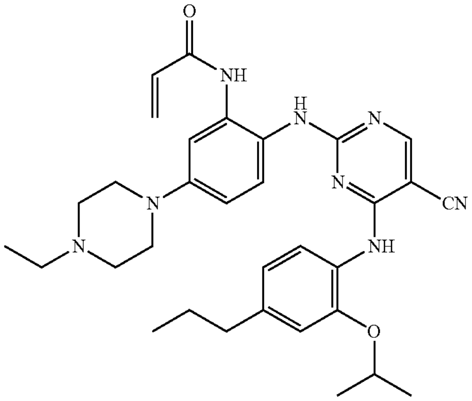 [SMILES: C=CC(=O)Nc1cc(N2CCN(CC)CC2)ccc1Nc1ncc(C#N)c(Nc2ccc(CCC)cc2OC(C)C)n1] | N-(2-((5-cyano-4-((2-isopropoxy-4-propylphenyl)amino)pyrimidin-2-yl)amino)-5-(4-ethylpiperazin-1-yl)phenyl) acrylamide | 1$^1$H NMR (400 MHz, DMSO-$d_6$) δ 9.66 (s, 1H), 8.89 (s, 1H), 8.44 (s, 1H), 8.22 (s, 1H), 7.71 (s, 1H), 7.35 (s, 1H), 7.25 (s, 1H), 6.91 (s, 1H), 6.79 (dd, J = 9.0, 2.8 Hz, 1H), 6.62-6.54 (m, 1H), 6.49 (dd, J = 17.0, 10.1 Hz, 1H), 6.24 (dd, J = 17.0, 2.0 Hz, 1H), 5.74 (dd, J = 10.1, 2.0 Hz, 1H), 4.63 (d, J = 7.4 Hz, 1H), 3.15 (s, 4H), 2.53 (s, 6H), 2.40 (d, J = 7.5 Hz, 2H), 1.58 (q, J = 7.4 Hz, 2H), 1.25 (d, J = 6.1 Hz, 6H), 1.05 (t, J = 7.1 Hz, 3H), 0.90 (t, J = 7.3 Hz, 3H). MS: 569 $[M + H]^+$ |
| Example 39. | 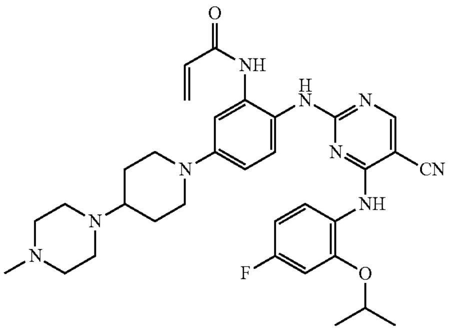 [SMILES: C=CC(=O)Nc1cc(N2CCC(N3CCN(C)CC3)CC2)ccc1Nc1ncc(C#N)c(Nc2ccc(F)cc2OC(C)C)n1] | N-(2-((5-cyano-4-((4-fluoro-2-isopropoxyphenyl)amino)pyrimidin-2-yl)amino)-5-(4-(4-methylpiperazin-1-yl)piperidin-1-yl)phenyl) acrylamide | $^1$H NMR (400 MHz, DMSO-$d_6$) δ 9.64 (s, 1H), 8.86 (s, 1H), 8.40 (d, J = 18.5 Hz, 2H), 7.73 (s, 1H), 7.29 (d, J = 8.7 Hz, 1H), 7.21 (s, 1H), 7.03 (d, J = 10.6 Hz, 1H), 6.76 (dd, J = 9.0, 2.8 Hz, 1H), 6.54-6.47 (m, 2H), 6.23 (dd, J = 16.9, 2.0 Hz, 1H), 5.74 (dd, J = 10.1, 2.0 Hz, 1H), 4.64 (s, 1H), 3.69 (d, J = 12.3 Hz, 2H), 3.31 (s, 4H), 2.70 (t, J = 11.7 Hz, 2H), 2.32 (br, 5H), 2.14 (s, 3H), 1.84 (d, J = 12.0 Hz, 2H), 1.56-1.43 (m, 2H), 1.23 (d, J = 6.0 Hz, 6H). MS: 614 $[M + H]^+$; |
| Example 40. | 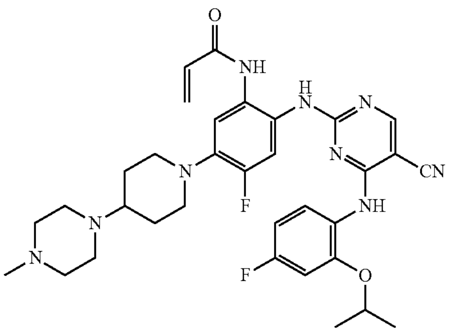 [SMILES: C=CC(=O)Nc1cc(N2CCC(N3CCN(C)CC3)CC2)c(F)cc1Nc1ncc(C#N)c(Nc2ccc(F)cc2OC(C)C)n1] | N-(2-((5-cyano-4-((4-fluoro-2-isopropoxyphenyl)amino)pyrimidin-2-yl)amino)-4-fluoro-5-(4-(4-methylpiperazin-1-yl)piperidin-1-yl)phenyl) acrylamide | $^1$H NMR (400 MHz, DMSO-$d_6$) δ 9.75 (s, 1H), 8.92 (s, 1H), 8.69 (s, 1H), 8.45 (s, 1H), 7.61 (s, 1H), 7.34 (d, J = 14.3 Hz, 1H), 7.19 (d, J = 8.9 Hz, 1H), 7.01 (dd, J = 11.0, 2.7 Hz, 1H), 6.64 (s, 1H), 6.46 (dd, J = 16.9, 10.1 Hz, 1H), 6.25 (dd, J = 17.0, 2.0 Hz, 1H), 5.76 (dd, J = 10.0, 2.0 Hz, 1H), 4.60 (p, J = 6.0 Hz, 1H), 3.36 (s, 6H), 2.62 (t, J = 11.5 Hz, 2H), 2.33 (s, 4H), 2.29 (dt, J = 11.5, 3.8 Hz, 1H), 2.15 (s, 3H), 1.85 (d, J = 12.1 Hz, 2H), 1.58 (td, J = 11.8, 3.7 Hz, 2H), 1.20 (d, J = 6.0 Hz, 6H). MS: 632 $[M + H]^+$; |

TABLE 3-continued

Structures, names and hydrogen NMR and mass spectrometry characterization data of the compounds prepared in Examples 2-81.

| No. | Structure | Name | Characterization |
|---|---|---|---|
| Example 41. | 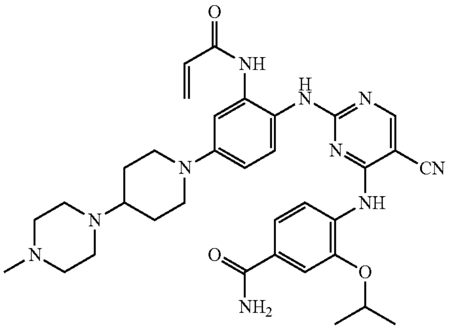 | 4-((2-((2-acrylamido-4-(4-(4-methylpiperazin-1-yl)piperidin-1-yl)phenyl)amino)-5-cyanopyrimidin-4-yl)amino)-3-isopropoxybenzamide | $^1$H NMR (400 MHz, DMSO-$d_6$) δ 9.72 (s, 1H), 9.05 (s, 1H), 8.49 (d, J = 16.4 Hz, 1H), 8.33 (s, 1H), 8.18 (d, J = 6.6 Hz, 1H), 7.95 (d, J = 17.4 Hz, 1H), 7.57 (s, 1H), 7.33 (s, 3H), 7.26 (d, J = 8.9 Hz, 1H), 6.83 (s, 1H), 6.56-6.45 (m, 1H), 6.25 (ddd, J = 17.0, 7.6, 2.0 Hz, 1H), 5.75 (d, J = 10.5 Hz, 1H), 4.72 (d, J = 8.3 Hz, 1H), 3.73 (s, 2H), 3.41 (s, 4H), 2.72 (d, J = 12.8 Hz, 2H), 2.34 (s, 5H), 2.16 (s, 3H), 1.86 (d, J = 12.4 Hz, 2H), 1.55-1.44 (m, 2H), 1.30 (dd, J = 6.3, 3.3 Hz, 6H). MS: 639 [M + H]$^+$; |
| Example 42. | 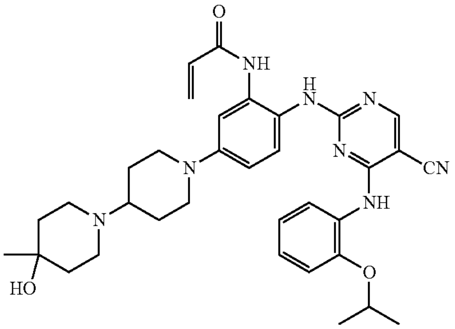 [SMILES: C=CC(=O)Nc1cc(N2CCC(N3CCC(C)(O)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-hydroxy-4-methyl-[1,4'-bipiperidin]-1'-yl)phenyl)acrylamide | $^1$H NMR (400 MHz, DMSO-$d_6$) δ 9.69 (s, 1H), 8.98 (s, 1H), 8.48 (s, 1H), 8.32 (s, 2H), 7.95 (s, 1H), 7.32 (d, J = 17.4 Hz, 1H), 7.09 (s, 2H), 6.80 (d, J = 8.4 Hz, 1H), 6.70 (s, 1H), 6.50 (dd, J = 17.0, 10.2 Hz, 1H), 6.23 (dd, J = 17.0, 2.1 Hz, 1H), 5.78-5.70 (m, 1H), 4.64 (s, 1H), 4.10 (s, 1H), 3.72 (d, J = 12.1 Hz, 2H), 3.34 (br, 4H), 2.71 (d, J = 12.9 Hz, 2H), 2.45 (s, 2H), 1.99 (dt, J = 12.6, 7.0 Hz, 1H), 1.83 (d, J = 12.0 Hz, 2H), 1.63-1.47 (m, 2H), 1.44 (d, J = 8.1 Hz, 2H), 1.27 (d, J = 6.0 Hz, 6H), 1.09 (s, 3H). MS: 611 [M + H]$^+$; |
| Example 43. | 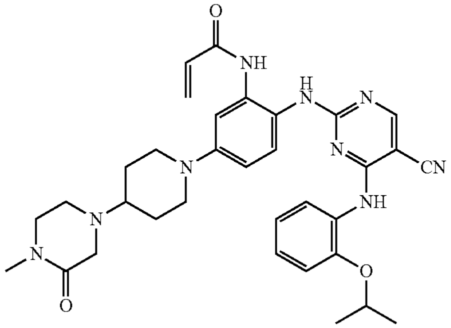 [SMILES: C=CC(=O)Nc1cc(N2CCC(N3CCN(C)C(=O)C3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(4-methyl-3-oxopiperazin-1-yl)piperidin-1-yl)phenyl)acrylamide | $^1$H NMR (400 MHz, DMSO-$d_6$) δ 9.67 (s, 1H), 8.97 (s, 1H), 8.48 (s, 1H), 8.25 (s, 2H), 7.95 (s, 1H), 7.42-7.00 (m, 4H), 6.82 (d, J = 9.1 Hz, 1H), 6.50 (dd, J = 16.9, 10.2 Hz, 1H), 6.24 (dd, J = 17.0, 2.0 Hz, 1H), 5.74 (d, J = 10.4 Hz, 1H), 4.65 (s, 1H), 3.71 (d, J = 12.4 Hz, 2H), 3.25 (t, J = 5.4 Hz, 2H), 3.12 (s, 2H), 2.82 (s, 4H), 2.75 (s, 3H), 2.44-2.40 (m, 1H), 1.89 (d, J = 12.3 Hz, 2H), 1.52 (d, J = 12.0 Hz, 2H), 1.27 (d, J = 6.0 Hz, 6H). MS: 610 [M + H]$^+$; |
| Example 44. | 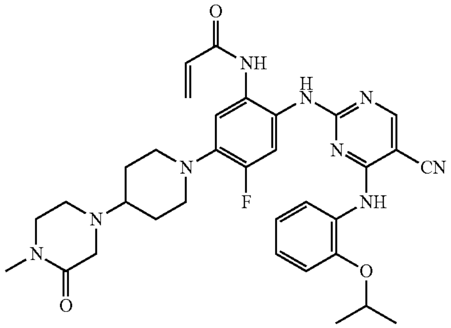 [SMILES: C=CC(=O)Nc1cc(N2CCC(N3CCN(C)C(=O)C3)CC2)c(F)cc1Nc1ncc(C#N)c(Nc2ccccc2OC(C)C)n1] | N-(2-((5-cyano-4-((2-isopropoxyphenyl)amino)pyrimidin-2-yl)amino)-4-fluoro-5-(4-(4-methyl-3-oxopiperazin-1-yl)piperidin-1-yl)phenyl)acrylamide | $^1$H NMR (400 MHz, DMSO-$d_6$) δ 9.79 (s, 1H), 9.07 (s, 1H), 8.49 (d, J = 11.3 Hz, 2H), 7.89 (s, 1H), 7.43 (d, J = 13.9 Hz, 1H), 7.29 (d, J = 9.1 Hz, 1H), 7.10 (d, J = 4.2 Hz, 2H), 6.81 (s, 1H), 6.48 (dd, J = 17.0, 10.1 Hz, 1H), 6.25 (dd, J = 17.0, 2.0 Hz, 1H), 5.77 (dd, J = 10.1, 2.0 Hz, 1H), 4.63 (p, J = 6.0 Hz, 1H), 4.38 (t, J = 12.3 Hz, 1H), 3.42 (d, J = 11.5 Hz, 2H), 3.27 (s, 2H), 2.95 (s, 2H), 2.74 (t, J = 11.6 Hz, 2H), 2.57 (t, J = 5.4 Hz, 2H), 2.21 (s, 3H), 2.05-1.83 (m, 2H), 1.62 (d, J = 11.9 Hz, 2H), 1.26 (d, J = 6.0 Hz, 6H). MS: 628 [M + H]$^+$; |

TABLE 3-continued

Structures, names and hydrogen NMR and mass spectrometry characterization data of the compounds prepared in Examples 2-81.

| No. | Structure | Name | Characterization |
|---|---|---|---|
| Example 45. | 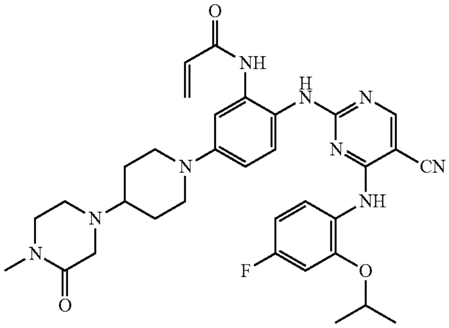 [SMILES: C=CC(=O)Nc1cc(N2CCC(N3CCN(C)C(=O)C3)CC2)ccc1Nc1ncc(C#N)c(Nc2ccc(F)cc2OC(C)C)n1] | N-(2-((5-cyano-4-((4-fluoro-2-isopropoxyphenyl)amino)pyrimidin-2-yl)amino)-5-(4-(4-methyl-3-oxopiperazin-1-yl)piperidin-1-yl)phenyl)acrylamide | $^1$H NMR (400 MHz, DMSO-$d_6$) δ 9.66 (s, 1H), 8.87 (s, 1H), 8.42 (s, 2H), 7.71 (s, 1H), 7.30 (d, J = 8.6 Hz, 2H), 7.22 (s, 1H), 7.04 (d, J = 10.8 Hz, 1H), 6.77 (dd, J = 9.0, 2.8 Hz, 1H), 6.64-6.41 (m, 1H), 6.23 (dd, J = 17.0, 2.0 Hz, 1H), 5.74 (dd, J = 10.2, 2.0 Hz, 1H), 4.64 (s, 2H), 3.68 (d, J = 12.5 Hz, 2H), 3.24 (t, J = 5.4 Hz, 2H), 3.11 (s, 2H), 2.82 (s, 3H), 2.78-2.68 (m, 4H), 1.87 (d, J = 12.3 Hz, 2H), 1.54-1.43 (m, 2H), 1.23 (d, J = 6.0 Hz, 6H). MS: 628 [M + H]$^+$; |
| Example 46. | 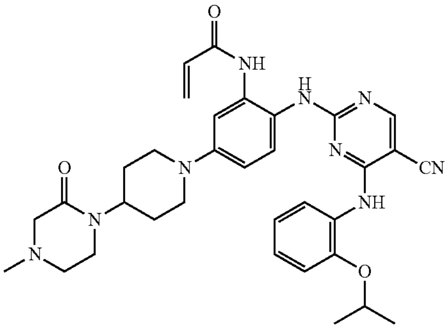 [SMILES: C=CC(=O)Nc1cc(N2CCC(N3CCN(C)CC3=O)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(4-methyl-2-oxopiperazin-1-yl)piperidin-1-yl)phenyl)acrylamide | $^1$H NMR (400 MHz, DMSO-$d_6$) δ 9.68 (s, 1H), 8.98 (s, 1H), 8.47 (s, 1H), 8.25 (s, 1H), 7.95 (s, 1H), 7.35 (d, J = 22.9 Hz, 2H), 7.06 (d, J = 18.2 Hz, 2H), 6.87-6.78 (m, 1H), 6.72 (s, 1H), 6.50 (dd, J = 16.9, 10.1 Hz, 1H), 6.24 (dd, J = 17.0, 2.0 Hz, 1H), 5.74 (dd, J = 10.1, 2.0 Hz, 1H), 4.71-4.60 (m, 1H), 4.44 (d, J = 11.7 Hz, 1H), 3.77 (d, J = 12.4 Hz, 2H), 3.23 (d, J = 5.5 Hz, 2H), 2.98 (s, 2H), 2.79 (t, J = 12.2 Hz, 2H), 2.59 (br, 2H), 2.23 (s, 3H), 1.82 (dt, J = 12.9, 6.5 Hz, 2H), 1.64-1.52 (m, 2H), 1.27 (d, J = 6.0 Hz, 6H). MS: 610 [M + H]$^+$; |
| Example 47. | 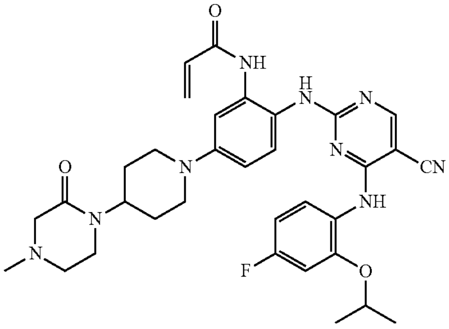 [SMILES: C=CC(=O)Nc1cc(N2CCC(N3CCN(C)CC3=O)CC2)ccc1Nc1ncc(C#N)c(Nc2ccc(F)cc2OC(C)C)n1] | N-(2-((5-cyano-4-((4-fluoro-2-isopropoxyphenyl)amino)pyrimidin-2-yl)amino)-5-(4-(4-methyl-2-oxopiperazin-1-yl)piperidin-1-yl)phenyl)acrylamide | $^1$H NMR (400 MHz, DMSO-$d_6$) δ 9.68 (s, 1H), 8.88 (s, 1H), 8.42 (s, 2H), 7.73 (s, 1H), 7.27 (d, J = 28.4 Hz, 2H), 7.04 (d, J = 11.1 Hz, 1H), 6.78 (dt, J = 6.3, 3.9 Hz, 1H), 6.56 (d, J = 11.6 Hz, 1H), 6.48 (dd, J = 17.0, 10.2 Hz, 1H), 6.24 (dd, J = 17.0, 2.0 Hz, 1H), 5.75 (d, J = 10.5 Hz, 1H), 4.66 (d, J = 6.4 Hz, 1H), 4.42 (t, J = 12.4 Hz, 1H), 3.76 (d, J = 12.4 Hz, 2H), 3.22 (s, 2H), 2.98 (s, 2H), 2.77 (t, J = 12.1 Hz, 2H), 2.58 (s, 2H), 2.23 (s, 3H), 1.81 (td, J = 13.9, 10.0 Hz, 2H), 1.59 (d, J = 13.3 Hz, 2H), 1.23 (d, J = 5.9 Hz, 6H). MS: 628 [M + H]$^+$; |
| Example 48. | 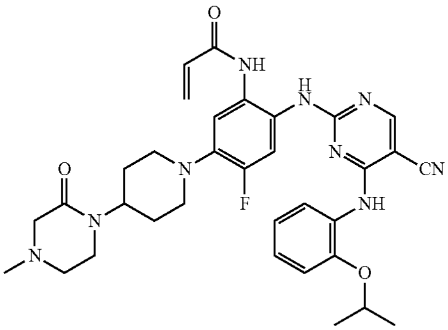 [SMILES: C=CC(=O)Nc1cc(N2CCC(N3CCN(C)CC3=O)CC2)c(F)cc1Nc1ncc(C#N)c(Nc2ccccc2OC(C)C)n1] | N-(2-((5-cyano-4-((2-isopropoxyphenyl)amino)pyrimidin-2-yl)amino)-4-fluoro-5-(4-(4-methyl-2-oxopiperazin-1-yl)piperidin-1-yl)phenyl)acrylamide | $^1$H NMR (400 MHz, DMSO-$d_6$) δ 9.79 (s, 1H), 9.07 (s, 1H), 8.48 (d, J = 13.1 Hz, 2H), 7.90 (s, 1H), 7.43 (d, J = 14.0 Hz, 1H), 7.29 (d, J = 9.2 Hz, 1H), 7.10 (d, J = 4.2 Hz, 2H), 6.81 (s, 1H), 6.48 (dd, J = 17.0, 10.2 Hz, 1H), 6.25 (dd, J = 16.9, 2.0 Hz, 1H), 5.77 (dd, J = 10.1, 2.0 Hz, 1H), 4.63 (p, J = 6.1 Hz, 1H), 4.45-4.29 (m, 1H), 3.42 (d, J = 11.6 Hz, 2H), 3.27 (s, 2H), 2.97 (s, 2H), 2.75 (t, J = 11.7 Hz, 2H), 2.59 (s, 2H), 2.22 (s, 3H), 1.90 (td, J = 13.1, 9.2 Hz, 2H), 1.62 (d, J = 11.8 Hz, 2H), 1.26 (d, J = 6.0 Hz, 6H). MS: 628 [M + H]$^+$; |

TABLE 3-continued

Structures, names and hydrogen NMR and mass spectrometry characterization data of the compounds prepared in Examples 2-81.

| No. | Structure | Name | Characterization |
|---|---|---|---|
| Example 49. | 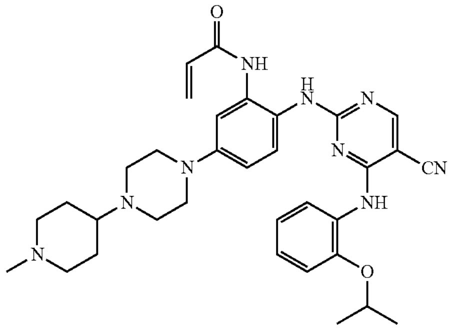 [SMILES: C=CC(=O)Nc1cc(N2CCN(C3CCN(C)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(1-methylpiperidin-4-yl)piperazin-1-yl)phenyl)acrylamide | $^1$H NMR (400 MHz, DMSO-$d_6$) δ 9.68 (s, 1H), 8.97 (s, 1H), 8.47 (s, 1H), 8.24 (s, 1H), 7.94 (s, 1H), 7.36 (s, 1H), 7.29 (s, 1H), 7.08 (s, 2H), 6.80 (d, J = 8.9 Hz, 1H), 6.70 (s, 1H), 6.50 (dd, J = 17.0, 10.2 Hz, 1H), 6.24 (dd, J = 17.0, 2.0 Hz, 1H), 5.74 (dd, J = 10.0, 2.0 Hz, 1H), 4.68-4.60 (m, 1H), 3.12 (s, 4H), 2.83 (d, J = 10.9 Hz, 2H), 2.63 (d, J = 5.6 Hz, 4H), 2.17 (br, 4H), 1.90 (s, 2H), 1.77 (d, J = 12.2 Hz, 2H), 1.51-1.41 (m, 2H), 1.27 (d, J = 6.0 Hz, 6H). MS: 596 $[M + H]^+$; |
| Example 50. | 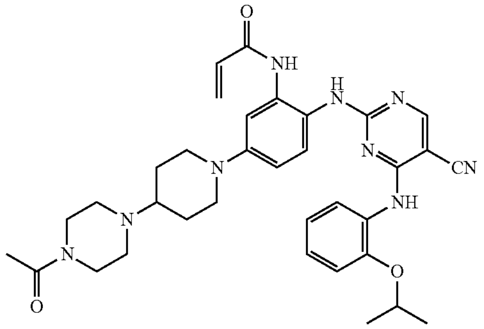 [SMILES: C=CC(=O)Nc1cc(N2CCC(N3CCN(C(C)=O)CC3)CC2)ccc1Nc1ncc(C#N)c(Nc2ccccc2OC(C)C)n1] | N-(5-(4-(4-acetylpiperazin-1-yl)piperidin-1-yl)-2-((5-cyano-4-((2-isopropoxyphenyl)amino)pyrimidin-2-yl)amino)phenyl)acrylamide | 1H NMR (400 MHz, DMSO-$d_6$) δ 9.65 (s, 1H), 8.97 (s, 1H), 8.47 (s, 1H), 8.24 (s, 1H), 7.95 (s, 1H), 7.34-7.28 (m, 2H), 7.07 (t, J = 12.7 Hz, 2H), 6.84-6.76 (m, 1H), 6.71 (s, 1H), 6.50 (dd, J = 16.9, 10.2 Hz, 1H), 6.24 (dd, J = 16.9, 2.0 Hz, 1H), 5.79-5.70 (m, 1H), 4.68-4.60 (m, 1H), 3.72 (d, J = 12.1 Hz, 2H), 3.41 (dt, J = 9.3, 4.8 Hz, 4H), 2.71 (t, J = 12.1 Hz, 2H), 2.51-2.36 (m, 5H), 1.98 (s, 3H), 1.88-1.79 (m, 2H), 1.60-1.46 (m, 2H), 1.27 (d, J = 6.0 Hz, 6H). MS: 624 $[M + H]^+$; |
| Example 51. | 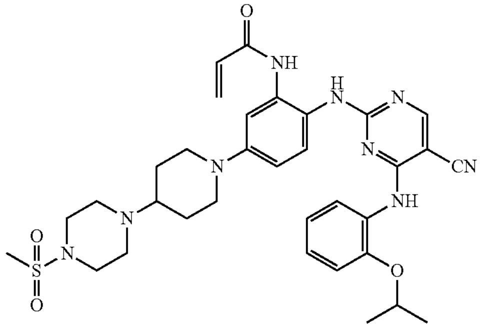 [SMILES: C=CC(=O)Nc1cc(N2CCC(N3CCN(S(C)(=O)=O)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(4-(methylsulfonyl)piperazin-1-yl)piperidin-1-yl)phenyl)acrylamide | $^1$H NMR (400 MHz, DMSO-$d_6$) δ 9.65 (s, 1H), 8.96 (s, 1H), 8.47 (s, 1H), 8.25 (s, 1H), 7.95 (s, 1H), 7.30 (s, 2H), 7.08 (s, 2H), 6.81 (d, J = 9.0 Hz, 1H), 6.71 (s, 1H), 6.50 (dd, J = 16.9, 10.1 Hz, 1H), 6.24 (dd, J = 17.0, 2.0 Hz, 1H), 5.74 (dd, J = 10.0, 2.0 Hz, 1H), 4.68-4.60 (m, 1H), 3.72 (d, J = 12.1 Hz, 2H), 3.10 (t, J = 4.7 Hz, 4H), 2.87 (s, 3H), 2.72 (t, J = 12.0 Hz, 2H), 2.61 (t, J = 4.7 Hz, 4H), 2.46 (br, 1H), 1.86 (d, J = 12.0 Hz, 2H), 1.61-1.50 (m, 2H), 1.28 (d, J = 6.0 Hz, 6H). MS: 660 $[M + H]^+$; |
| Example 52. | 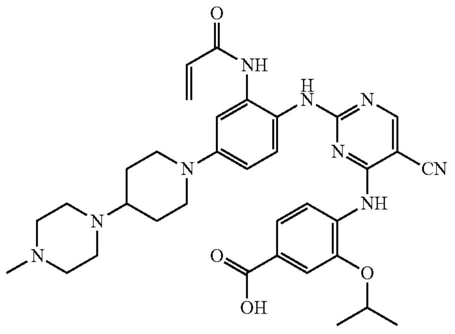 [SMILES: C=CC(=O)Nc1cc(N2CCC(N3CCN(C)CC3)CC2)ccc1Nc1ncc(C#N)c(Nc2ccc(C(=O)O)cc2OC(C)C)n1] | 4-((2-((2-acrylamido-4-(4-(4-methylpiperazin-1-yl)piperidin-1-yl)phenyl)amino)-5-cyanopyrimidin-4-yl)amino)-3-isopropoxybenzoic acid | $^1$H NMR (400 MHz, DMSO-$d_6$) δ 9.67 (s, 1H), 9.07 (s, 1H), 8.54 (s, 1H), 8.26 (d, J = 11.6 Hz, 1H), 8.00 (s, 1H), 7.59 (d, J = 14.3 Hz, 1H), 7.51 (s, 1H), 7.36 (s, 1H), 7.30 (s, 1H), 6.83 (s, 1H), 6.51 (dd, J = 16.9, 10.2 Hz, 1H), 6.23 (dd, J = 16.9, 2.0 Hz, 1H), 5.79-5.69 (m, 1H), 4.70 (s, 1H), 3.74 (s, 2H), 3.34 (br, 4H), 2.74 (s, 2H), 2.36 (br, 5H), 2.17 (s, 3H), 1.85 (d, J = 11.8 Hz, 2H), 1.53 (d, J = 12.7 Hz, 2H), 1.30 (d, J = 6.0 Hz, 6H). MS: 640 $[M + H]^+$; |

TABLE 3-continued

| Structures, names and hydrogen NMR and mass spectrometry characterization data of the compounds prepared in Examples 2-81. | | | |
|---|---|---|---|
| No. | Structure | Name | Characterization |
| Example 53. | 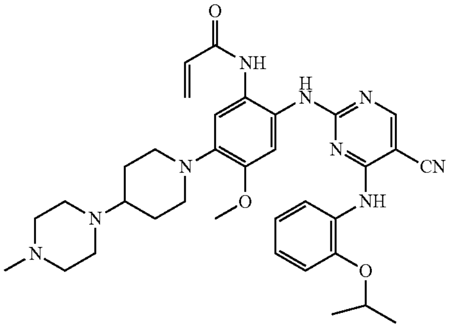 [SMILES: C=CC(=O)Nc1cc(N2CCC(N3CCN(C)CC3)CC2)c(OC)cc1Nc1ncc(C#N)c(Nc2ccccc2OC(C)C)n1] | N-(2-((5-cyano-4-((2-isopropoxyphenyl)amino)pyrimidin-2-yl)amino)-4-methoxy-5-(4-(4-methylpiperazin-1-yl)piperidin-1-yl)phenyl)acrylamide | $^1$H NMR (400 MHz, DMSO-$d_6$) δ 9.73 (s, 1H), 9.07 (s, 1H), 8.49 (s, 1H), 8.28 (s, 1H), 8.02 (s, 1H), 7.14 (d, J = 15.5 Hz, 2H), 7.07 (s, 2H), 6.66 (s, 1H), 6.47 (dd, J = 16.9, 10.2 Hz, 1H), 6.23 (dd, J = 17.0, 2.1 Hz, 1H), 5.73 (dd, J = 10.0, 2.1 Hz, 1H), 4.62 (s, 1H), 3.62 (br, 4H), 3.49-3.35 (m, 5H), 2.65 (s, 4H), 2.55 (d, J = 11.7 Hz, 2H), 2.37 (br, 4H), 1.87 (s, 2H), 1.61 (s, 2H), 1.26 (d, J = 6.0 Hz, 6H). MS: 626 [M + H]$^+$ |
| Example 54. | 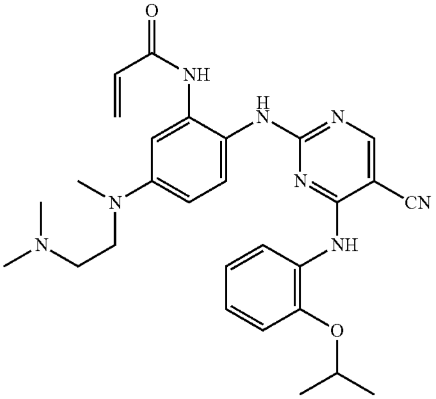 [SMILES: C=CC(=O)Nc1cc(N(C)CCN(C)C)ccc1Nc1ncc(C#N)c(Nc2ccccc2OC(C)C)n1] | N-(2-((5-cyano-4-((2-isopropoxyphenyl)amino)pyrimidin-2-yl)amino)-5-((2-(dimethylamino)ethyl)(methyl)amino)phenylacrylamide | $^1$H NMR (400 MHz, DMSO-$d_6$) δ 9.70 (s, 1H), 8.91 (s, 1H), 8.47 (s, 1H), 8.18 (s, 1H), 7.98 (s, 1H), 7.34 (s, 1H), 7.09 (s, 3H), 7.01 (s, 1H), 6.61 (d, J = 8.9 Hz, 1H), 6.51 (dd, J = 17.0, 10.2 Hz, 1H), 6.24 (dd, J = 17.0, 2.0 Hz, 1H), 5.77-5.70 (m, 1H), 4.65 (s, 1H), 3.50 (t, J = 6.9 Hz, 2H), 2.93 (s, 3H), 2.64 (s, 2H), 2.38 (s, 6H), 1.28 (d, J = 6.0 Hz, 6H). MS: 515 [M + H]$^+$; |
| Example 55. | 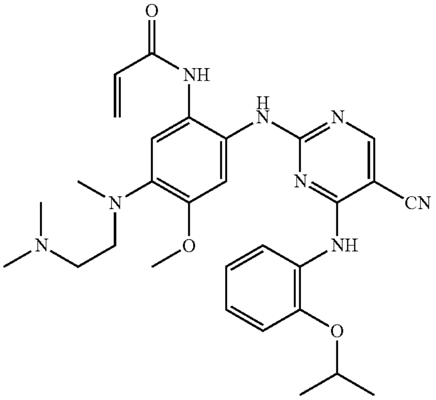 [SMILES: C=CC(=O)Nc1cc(N(C)CCN(C)C)c(OC)cc1Nc1ncc(C#N)c(Nc2ccccc2OC(C)C)n1] | N-(2-((5-cyano-4-((2-isopropoxyphenyl)amino)pyrimidin-2-yl)amino)-5-((2-(dimethylamino)ethyl)(methyl)amino)-4-methoxyphenyl)acrylamide | $^1$H NMR (400 MHz, DMSO-$d_6$) δ 9.77 (s, 1H), 9.02 (s, 1H), 8.49 (s, 1H), 8.27 (s, 1H), 8.05 (s, 1H), 7.23-6.94 (m, 4H), 6.67 (s, 1H), 6.47 (dd, J = 17.0, 10.1 Hz, 1H), 6.24 (dd, J = 16.9, 2.1 Hz, 1H), 5.74 (dd, J = 10.1, 2.1 Hz, 1H), 4.66-4.58 (m, 1H), 3.61 (s, 3H), 3.16 (d, J = 7.8 Hz, 2H), 2.74 (s, 3H), 2.51 (br, 2H), 2.22 (s, 6H), 1.26 (d, J = 6.0 Hz, 6H). MS: 545 [M + H]$^+$; |
| Example 56. | 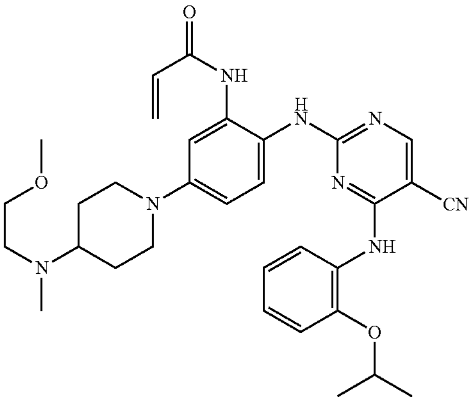 [SMILES: C=CC(=O)Nc1cc(N2CCC(N(C)CCOC)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-((2-methoxyethyl)(methyl)amino)piperidin-1-yl)phenyl)acrylamide | $^1$H NMR (400 MHz, DMSO-$d_6$) δ 9.65 (s, 1H), 8.95 (s, 1H), 8.47 (s, 1H), 8.25 (s, 1H), 7.95 (s, 1H), 7.35 (s, 1H), 7.29 (s, 1H), 7.08 (s, 2H), 6.81 (d, J = 9.0 Hz, 1H), 6.69 (s, 1H), 6.50 (dd, J = 17.0, 10.3 Hz, 1H), 6.29-6.19 (m, 1H), 5.74 (d, J = 10.2 Hz, 1H), 4.74-4.54 (m, 1H), 3.73 (d, J = 12.1 Hz, 2H), 3.40 (d, J = 4.8 Hz, 2H), 3.25 (s, 3H), 2.72 (d, J = 12.2 Hz, 2H), 2.59 (s, 3H), 2.23 (s, 3H), 1.78 (s, 2H), 1.56-1.49 (m, 2H), 1.27 (d, J = 6.0 Hz, 6H). MS: 585 [M + H]$^+$; |

TABLE 3-continued

Structures, names and hydrogen NMR and mass spectrometry characterization data of the compounds prepared in Examples 2-81.

| No. | Structure | Name | Characterization |
|---|---|---|---|
| Example 57. | 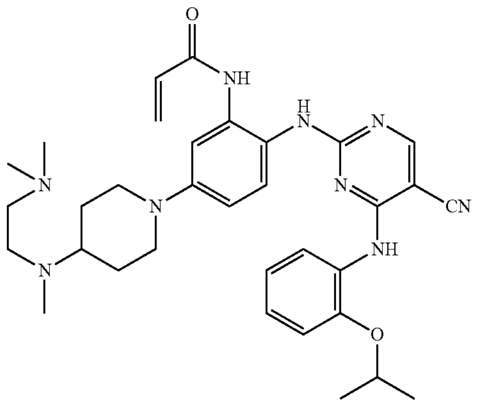 [SMILES: C=CC(=O)Nc1cc(N2CCC(N(C)CCN(C)C)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-((2-(dimethylamino)ethyl)(methyl)amino)piperidin-1-yl)phenyl)acrylamide | $^1$H NMR (400 MHz, DMSO-$d_6$) δ 9.66 (s, 1H), 8.96 (s, 1H), 8.48 (s, 1H), 8.25 (s, 1H), 7.96 (s, 1H), 7.35 (s, 1H), 7.29 (s, 1H), 7.08 (s, 2H), 6.81 (d, J = 8.5 Hz, 1H), 6.67 (d, J = 15.2 Hz, 1H), 6.50 (dd, J = 17.1, 10.1 Hz, 1H), 6.29-6.19 (m, 1H), 5.74 (d, J = 10.6 Hz, 1H), 4.62 (s, 1H), 3.73 (d, J = 11.7 Hz, 2H), 2.73-2.67 (m, 2H), 2.36-2.27 (m, 3H), 2.21 (s, 6H), 2.16 (s, 5H), 1.78 (d, J = 12.2 Hz, 2H), 1.54 (s, 2H), 1.27 (d, J = 6.0 Hz, 6H). MS: 598 $[M + H]^+$ |
| Example 58. | 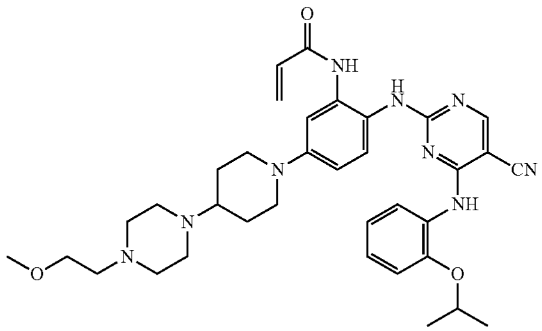 [SMILES: C=CC(=O)Nc1cc(N2CCC(N3CCN(CCOC)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(4-(2-methoxyethyl)piperazin-1-yl)piperidin-1-yl)phenyl)acrylamide | $^1$H NMR (400 MHz, DMSO-$d_6$) δ 9.65 (s, 1H), 8.96 (s, 1H), 8.47 (s, 1H), 8.24 (s, 1H), 7.95 (s, 1H), 7.32 (d, J = 18.8 Hz, 2H), 7.06 (d, J = 19.9 Hz, 2H), 6.80 (d, J = 8.9 Hz, 1H), 6.71 (s, 1H), 6.50 (dd, J = 16.9, 10.1 Hz, 1H), 6.24 (dd, J = 17.0, 2.0 Hz, 1H), 5.74 (dd, J = 10.2, 2.0 Hz, 1H), 4.68-4.60 (m, 1H), 3.70 (d, J = 12.0 Hz, 2H), 3.41 (t, J = 5.9 Hz, 2H), 3.33 (s, 6H), 3.23 (s, 3H), 2.71 (t, J = 12.1 Hz, 2H), 2.51-2.40 (m, 4H), 2.32 (s, 1H), 1.85 (d, J = 12.0 Hz, 2H), 1.57-1.44 (m, 2H), 1.27 (d, J = 6.0 Hz, 6H). MS: 640 $[M + H]^+$; |
| Example 59. | 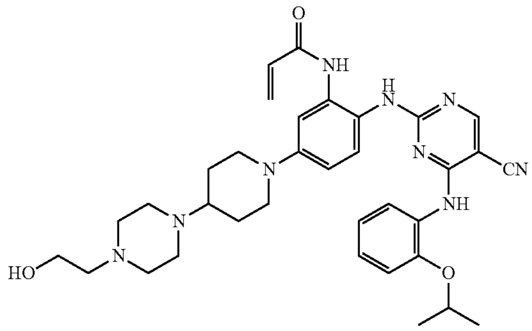 [SMILES: C=CC(=O)Nc1cc(N2CCC(N3CCN(CCO)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(4-(2-hydroxyethyl)piperazin-1-yl)piperidin-1-yl)phenyl)acrylamide | $^1$H NMR (400 MHz, DMSO-$d_6$) δ 9.65 (s, 1H), 8.96 (s, 1H), 8.47 (s, 1H), 8.24 (s, 1H), 7.95 (s, 1H), 7.32 (d, J = 18.3 Hz, 2H), 7.06 (d, J = 18.1 Hz, 2H), 6.80 (d, J = 9.0 Hz, 1H), 6.71 (s, 1H), 6.50 (dd, J = 16.9, 10.1 Hz, 1H), 6.24 (dd, J = 17.0, 2.0 Hz, 1H), 5.78-5.70 (m, 1H), 4.64 (s, 1H), 4.36 (t, J = 5.4 Hz, 1H), 3.70 (d, J = 12.0 Hz, 2H), 3.48 (q, J = 6.1 Hz, 2H), 3.33 (s, 4H), 2.71 (t, J = 12.3 Hz, 2H), 2.45-2.26 (m, 7H), 1.85 (d, J = 11.9 Hz, 2H), 1.51 (q, J = 11.7 Hz, 2H), 1.27 (d, J = 6.0 Hz, 6H). MS: 626 $[M + H]^+$; |
| Example 60. | 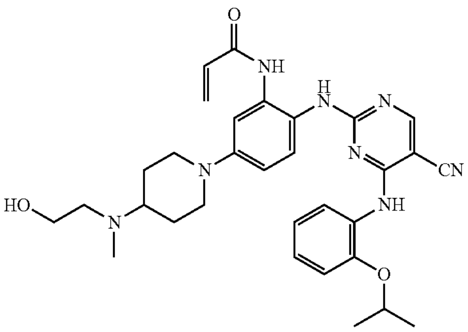 [SMILES: C=CC(=O)Nc1cc(N2CCC(N(C)CCO)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-((2-hydroxyethyl)(methyl)amino)piperidin-1-yl)phenyl)acrylamide | $^1$H NMR (400 MHz, DMSO-$d_6$) δ 9.66 (s, 1H), 8.96 (s, 1H), 8.47 (s, 1H), 8.25 (s, 1H), 7.96 (s, 1H), 7.35 (s, 1H), 7.30 (s, 1H), 7.08 (s, 2H), 6.81 (d, J = 8.9 Hz, 1H), 6.72 (s, 1H), 6.50 (dd, J = 16.9, 10.1 Hz, 1H), 6.24 (dd, J = 17.0, 2.0 Hz, 1H), 5.74 (dd, J = 10.2, 2.0 Hz, 1H), 4.68-4.60 (m, 1H), 4.39 (t, J = 5.7 Hz, 1H), 3.74 (d, J = 12.1 Hz, 2H), 3.48 (s, 2H), 2.72 (d, J = 12.0 Hz, 2H), 2.53-2.50 (m, 3H), 2.28 (s, 3H), 1.81 (s, 2H), 1.55 (d, J = 12.6 Hz, 2H), 1.28 (d, J = 6.0 Hz, 6H). MS: 571 $[M + H]^+$; |

TABLE 3-continued

Structures, names and hydrogen NMR and mass spectrometry characterization data of the compounds prepared in Examples 2-81.

| No. | Structure | Name | Characterization |
|---|---|---|---|
| Example 61. | 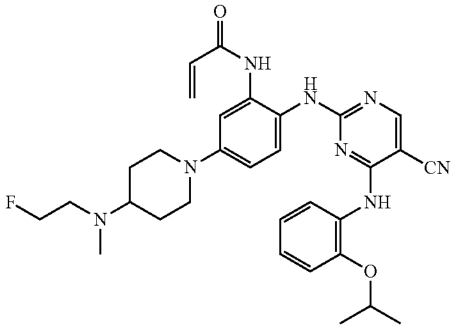 [SMILES: C=CC(=O)Nc1cc(N2CCC(N(C)CCF)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-((2-fluoroethyl)(methyl)amino)piperidin-1-yl)phenyl)acrylamide | $^1$H NMR (400 MHz, DMSO-$d_6$) δ 9.66 (s, 1H), 8.95 (s, 1H), 8.47 (s, 1H), 8.24 (s, 1H), 7.96 (s, 1H), 7.35 (s, 1H), 7.29 (s, 1H), 7.08 (t, J = 11.1 Hz, 2H), 6.81 (dd, J = 9.2, 2.8 Hz, 1H), 6.72 (s, 1H), 6.50 (dd, J = 17.0, 10.2 Hz, 1H), 6.24 (dd, J = 17.0, 2.0 Hz, 1H), 5.74 (dd, J = 10.1, 2.0 Hz, 1H), 4.68-4.60 (m, 1H), 4.54 (t, J = 5.1 Hz, 1H), 4.42 (t, J = 5.2 Hz, 1H), 3.73 (d, J = 12.2 Hz, 2H), 2.73 (td, J = 16.5, 12.5, 6.6 Hz, 4H), 2.56 (d, J = 11.2 Hz, 1H), 2.26 (s, 3H), 1.79 (d, J = 12.1 Hz, 2H), 1.54 (tt, J = 13.5, 6.8 Hz, 2H), 1.28 (d, J = 6.0 Hz, 6H). MS: 573 $[M + H]^+$ |
| Example 62. | 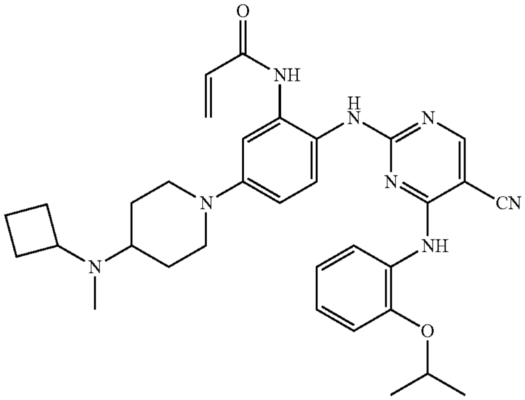 [SMILES: C=CC(=O)Nc1cc(N2CCC(N(C)C3CCC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(cyclobutyl(methyl)amino)piperidin-1-yl)phenyl)acrylamide | $^1$H NMR (400 MHz, DMSO-$d_6$) δ 9.66 (s, 1H), 8.96 (s, 1H), 8.47 (s, 1H), 8.24 (s, 1H), 7.96 (s, 1H), 7.34 (s, 1H), 7.28 (s, 1H), 7.07 (t, J = 12.6 Hz, 2H), 6.83-6.76 (m, 1H), 6.71 (s, 1H), 6.50 (dd, J = 16.9, 10.1 Hz, 1H), 6.24 (dd, J = 17.0, 2.0 Hz, 1H), 5.74 (dd, J = 10.1, 2.1 Hz, 1H), 4.68-4.60 (m, 1H), 3.74 (d, J = 12.0 Hz, 2H), 3.24-3.11 (m, 1H), 2.68 (t, J = 11.7 Hz, 2H), 2.56 (d, J = 17.8 Hz, 1H), 2.05 (s, 3H), 2.02-1.93 (m, 2H), 1.87-1.74 (m, 2H), 1.70-1.51 (m, 6H), 1.27 (d, J = 6.0 Hz, 6H). MS: 581 $[M + H]^+$; |
| Example 63. | 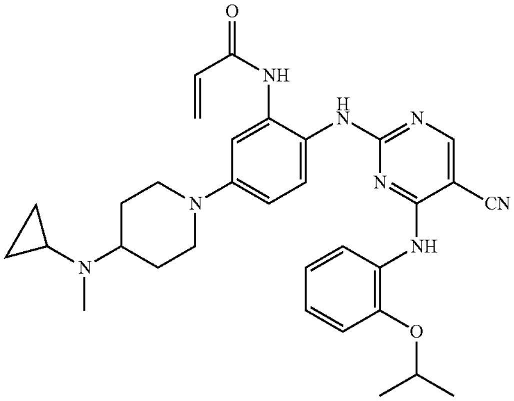 [SMILES: C=CC(=O)Nc1cc(N2CCC(N(C)C3CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(cyclopropyl(methyl)amino)piperidin-1-yl)phenyl)acrylamide | $^1$H NMR (400 MHz, DMSO-$d_6$) δ 9.66 (s, 1H), 8.95 (s, 1H), 8.47 (s, 1H), 8.24 (s, 1H), 7.96 (s, 1H), 7.35 (s, 1H), 7.31-7.26 (m, 1H), 7.06 (d, J = 19.3 Hz, 2H), 6.81 (d, J = 8.8 Hz, 1H), 6.72 (s, 1H), 6.50 (dd, J = 16.9, 10.1 Hz, 1H), 6.24 (dd, J = 17.0, 2.0 Hz, 1H), 5.74 (dd, J = 10.1, 2.0 Hz, 1H), 4.68-4.60 (m, 1H), 3.74 (d, J = 12.0 Hz, 2H), 2.70 (t, J = 12.1 Hz, 2H), 2.58 (d, J = 12.0 Hz, 1H), 2.28 (s, 3H), 1.89 (d, J = 12.1 Hz, 2H), 1.81 (tt, J = 6.7, 3.6 Hz, 1H), 1.66-1.53 (m, 2H), 1.28 (d, J = 6.0 Hz, 6H), 0.46 (dt, J = 6.3, 3.0 Hz, 2H), 0.31 (q, J = 3.4, 2.9 Hz, 2H). MS: 567 $[M + H]^+$ |
| Example 64. | 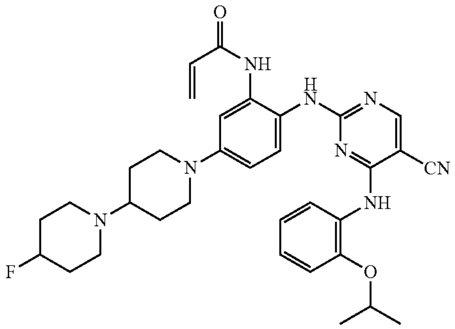 [SMILES: C=CC(=O)Nc1cc(N2CCC(N3CCC(F)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-fluoro-[1,4-bipiperidin]-1'-yl)phenyl)acrylamide | $^1$H NMR (400 MHz, DMSO-$d_6$) δ 9.65 (s, 1H), 8.97 (s, 1H), 8.47 (s, 1H), 8.24 (s, 1H), 7.94 (s, 1H), 7.45-7.25 (m, 2H), 7.08 (s, 1H), 7.03 (s, 1H), 6.80 (d, J = 8.9 Hz, 1H), 6.70 (s, 1H), 6.50 (dd, J = 16.9, 10.2 Hz, 1H), 6.23 (dd, J = 17.0, 2.0 Hz, 1H), 5.74 (dd, J = 10.1, 2.0 Hz, 1H), 4.80-4.55 (m, 1H), 3.72 (d, J = 12.2 Hz, 2H), 3.3 (br, 1H), 2.68 (d, J = 9.4 Hz, 4H), 2.43 (d, J = 10.1 Hz, 3H), 1.90-1.78 (m, 4H), 1.69 (s, 2H), 1.56 (t, J = 11.7 Hz, 2H), 1.27 (d, J = 6.0 Hz, 6H). MS: 599 $[M + H]^+$; |

TABLE 3-continued

Structures, names and hydrogen NMR and mass spectrometry characterization data of the compounds prepared in Examples 2-81.

| No. | Structure | Name | Characterization |
|---|---|---|---|
| Example 65. | 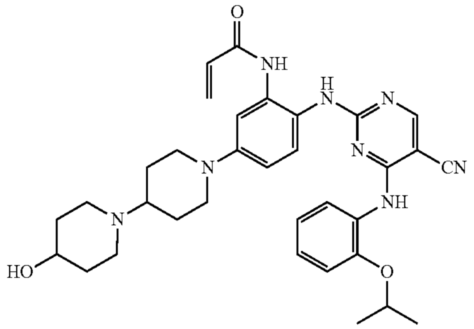 [SMILES: C=CC(=O)Nc1cc(N2CCC(N3CCC(O)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-hydroxy-[1,4-bipiperidin]-1'-yl)phenyl)acrylamide | $^1$H NMR (400 MHz, DMSO-$d_6$) δ 9.65 (s, 1H), 8.96 (s, 1H), 8.47 (s, 1H), 8.24 (s, 1H), 7.94 (s, 1H), 7.32 (d, J = 17.7 Hz, 2H), 7.08 (s, 1H), 7.03 (s, 1H), 6.80 (dd, J = 9.1, 2.7 Hz, 1H), 6.70 (s, 1H), 6.50 (dd, J = 17.0, 10.2 Hz, 1H), 6.24 (dd, J = 16.9, 2.1 Hz, 1H), 5.74 (dd, J = 10.0, 2.0 Hz, 1H), 4.64 (t, J = 6.4 Hz, 1H), 4.53 (d, J = 4.1 Hz, 1H), 3.71 (d, J = 12.0 Hz, 2H), 3.46-3.35 (m, 1H), 2.82-2.64 (m, 4H), 2.46-2.35 (m, 1H), 2.19 (t, J = 10.3 Hz, 2H), 1.84-1.67 (m, 4H), 1.60-1.46 (m, 2H), 1.36 (dd, J = 12.9, 9.7 Hz, 2H), 1.27 (d, J = 6.0 Hz, 6H). MS: 597 [M + H]$^+$; |
| Example 66. | 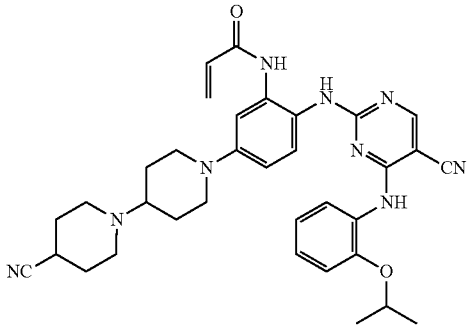 [SMILES: C=CC(=O)Nc1cc(N2CCC(N3CCC(C#N)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-cyano-[1,4-bipiperidin]-1'-yl)phenyl)acrylamide | $^1$H NMR (400 MHz, DMSO-$d_6$) δ 9.65 (s, 1H), 8.97 (s, 1H), 8.47 (s, 1H), 8.24 (s, 1H), 7.95 (s, 1H), 7.31 (br, 2H), 7.06 (d, J = 18.9 Hz, 2H), 6.81 (d, J = 9.0 Hz, 1H), 6.71 (s, 1H), 6.50 (dd, J = 17.0, 10.2 Hz, 1H), 6.24 (dd, J = 17.0, 2.0 Hz, 1H), 5.74 (dd, J = 10.1, 1.9 Hz, 1H), 4.68-4.60 (m, 1H), 3.74 (s, 2H), 3.34 (br, 4H), 2.87 (s, 1H), 2.69 (d, J = 12.5 Hz, 2H), 2.43 (s, 1H), 1.84 (s, 4H), 1.69 (s, 2H), 1.56 (s, 2H), 1.28 (d, J = 6.0 Hz, 6H). MS: 606 [M + H]$^+$; |
| Example 67. | 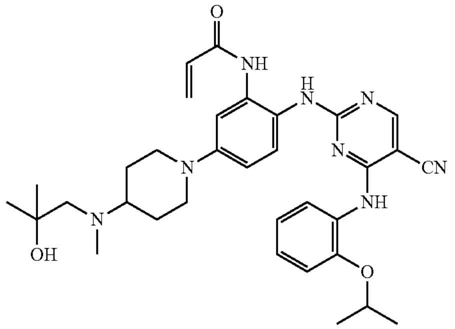 [SMILES: C=CC(=O)Nc1cc(N2CCC(N(C)CC(C)(C)O)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-((2-hydroxy-2-methylpropyl)(methyl)amino)piperidin-1-yl)phenyl)acrylamide | $^1$H NMR (400 MHz, DMSO-$d_6$) δ 9.68 (s, 1H), 8.96 (s, 1H), 8.47 (s, 1H), 8.25 (s, 1H), 7.96 (s, 1H), 7.35 (s, 1H), 7.28 (s, 1H), 7.09 (s, 2H), 6.81 (d, J = 9.0 Hz, 1H), 6.71 (s, 1H), 6.50 (dd, J = 17.0, 10.1 Hz, 1H), 6.24 (dd, J = 16.9, 2.0 Hz, 1H), 5.78-5.70 (m, 1H), 4.68-4.60 (m, 1H), 4.00 (s, 1H), 3.75 (d, J = 11.9 Hz, 2H), 2.67 (t, J = 12.1 Hz, 2H), 2.45-2.31 (m, 6H), 1.76 (s, 2H), 1.54 (s, 2H), 1.27 (d, J = 6.0 Hz, 6H), 1.08 (s, 6H). MS: 599 [M + H]$^+$; |
| Example 68. | 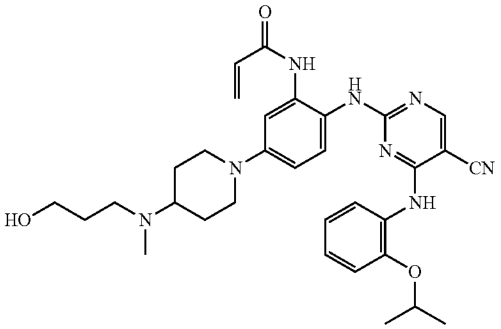 [SMILES: C=CC(=O)Nc1cc(N2CCC(N(C)CCCO)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-((3-hydroxypropyl)(methyl)amino)piperidin-1-yl)phenyl)acrylamide | $^1$H NMR (400 MHz, DMSO-$d_6$) δ 9.68 (s, 1H), 8.97 (s, 1H), 8.49-8.44 (m, 1H), 8.22 (s, 1H), 7.95 (s, 1H), 7.35 (s, 1H), 7.29 (s, 1H), 7.12-7.05 (m, 2H), 6.81 (d, J = 8.9 Hz, 1H), 6.78-6.67 (m, 1H), 6.50 (dd, J = 17.0, 10.2 Hz, 1H), 6.24 (dd, J = 17.0, 2.0 Hz, 1H), 5.78-5.70 (m, 1H), 4.73-4.47 (m, 1H), 3.74 (d, J = 12.1 Hz, 2H), 3.45 (t, J = 6.1 Hz, 2H), 2.71 (t, J = 12.2 Hz, 2H), 2.57-2.50 (m, 3H), 2.25 (s, 3H), 1.81 (d, J = 12.2 Hz, 2H), 1.59 (p, J = 7.6, 6.8 Hz, 4H), 1.27 (d, J = 5.9 Hz, 6H). MS: 585 [M + H]$^+$; |

TABLE 3-continued

| Structures, names and hydrogen NMR and mass spectrometry characterization data of the compounds prepared in Examples 2-81. | | | |
|---|---|---|---|
| No. | Structure | Name | Characterization |
| Example 69. | 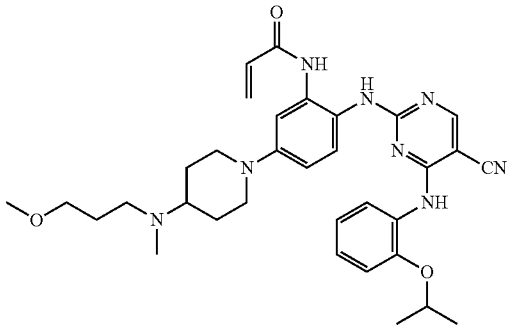 [SMILES: C=CC(=O)Nc1cc(N2CCC(N(C)CCCOC)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-((3-methoxypropyl)(methyl)amino)piperidin-1-yl)phenyl)acrylamide | $^1$H NMR (400 MHz, DMSO-$d_6$) δ 9.67 (s, 1H), 8.96 (s, 1H), 8.47 (s, 1H), 8.23 (d, J = 11.2 Hz, 1H), 7.95 (s, 1H), 7.35 (s, 1H), 7.31-7.26 (m, 1H), 7.06 (d, J = 18.7 Hz, 2H), 6.84-6.77 (m, 1H), 6.71 (s, 1H), 6.50 (dd, J = 17.0, 10.1 Hz, 1H), 6.24 (dd, J = 17.0, 2.0 Hz, 1H), 5.74 (dd, J = 10.0, 2.0 Hz, 1H), 4.68-4.60 (m, 1H), 3.72 (d, J = 12.1 Hz, 2H), 3.34 (t, J = 6.3 Hz, 2H), 3.22 (s, 3H), 2.71 (t, J = 12.3 Hz, 2H), 2.50-2.45 (m, 3H), 2.20 (s, 3H), 1.78 (d, J = 11.3 Hz, 2H), 1.69-1.46 (m, 4H), 1.28 (d, J = 6.0 Hz, 6H). MS: 599 $[M + H]^+$ |
| Example 70. | 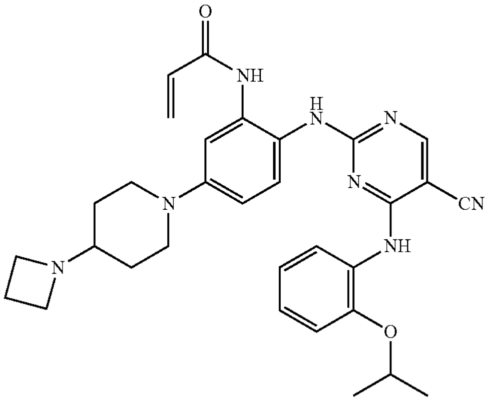 [SMILES: C=CC(=O)Nc1cc(N2CCC(N3CCC3)CC2)ccc1Nc1ncc(C#N)c(Nc2ccccc2OC(C)C)n1] | N-(5-(4-(azetidin-1-yl)piperidin-1-yl)-2-((5-cyano-4-((2-isopropoxyphenyl)amino)pyrimidin-2-yl)amino)phenyl)acrylamide | $^1$H NMR (400 MHz, DMSO-$d_6$) δ 9.66 (s, 1H), 8.95 (s, 1H), 8.47 (s, 1H), 8.24 (s, 1H), 7.95 (s, 1H), 7.34 (s, 1H), 7.30-7.24 (m, 1H), 7.07 (t, J = 12.2 Hz, 2H), 6.83-6.75 (m, 1H), 6.72 (s, 1H), 6.49 (dd, J = 17.0, 10.2 Hz, 1H), 6.23 (dd, J = 16.9, 2.0 Hz, 1H), 5.74 (dd, J = 10.1, 2.0 Hz, 1H), 4.64 (s, 1H), 3.53 (d, J = 12.2 Hz, 2H), 3.10 (t, J = 6.8 Hz, 4H), 2.79 (t, J = 11.0 Hz, 2H), 2.14 (d, J = 10.5 Hz, 1H), 1.94 (q, J = 6.9 Hz, 2H), 1.75-1.66 (m, 2H), 1.33-1.19 (m, 8H). MS: 553 $[M + H]^+$ |
| Example 71. | 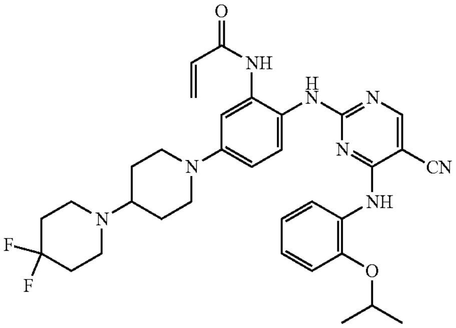 [SMILES: C=CC(=O)Nc1cc(N2CCC(N3CCC(F)(F)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4,4-difluoro-[1,4-bipiperidin]-1'-yl)phenyl)acrylamide | $^1$H NMR (400 MHz, DMSO-$d_6$) δ 9.66 (s, 1H), 8.97 (s, 1H), 8.47 (s, 1H), 8.24 (s, 1H), 7.95 (s, 1H), 7.41-7.22 (m, 2H), 7.07 (t, J = 13.3 Hz, 2H), 6.81 (d, J = 8.7 Hz, 1H), 6.71 (s, 1H), 6.50 (dd, J = 17.0, 10.2 Hz, 1H), 6.24 (dd, J = 17.0, 2.0 Hz, 1H), 5.74 (dd, J = 10.0, 2.0 Hz, 1H), 4.68-4.60 (m, 1H), 3.73 (d, J = 12.0 Hz, 2H), 2.76-2.58 (m, 6H), 2.55-2.50 (m, 1H), 1.98-1.90 (m, 4H), 1.82 (d, J = 12.2 Hz, 2H), 1.57 (q, J = 10.9 Hz, 2H), 1.28 (d, J = 6.0 Hz, 6H). MS: 617 $[M + H]^+$ |
| Example 72. | 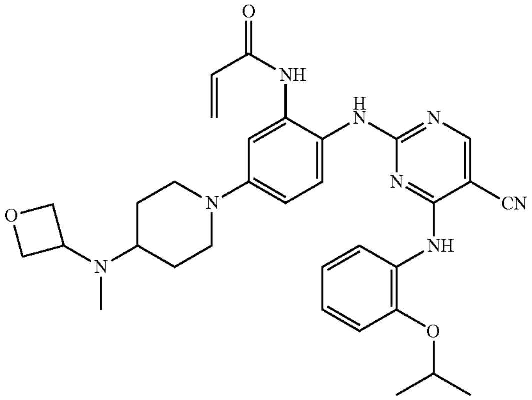 [SMILES: C=CC(=O)Nc1cc(N2CCC(N(C)C3COC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(methyl(oxetan-3-yl)amino)piperidin-1-yl)phenyl)acrylamide | 1H NMR (400 MHz, DMSO-$d_6$) δ 9.65 (s, 1H), 8.96 (s, 1H), 8.47 (s, 1H), 8.24 (s, 1H), 7.96 (s, 1H), 7.35 (s, 1H), 7.31-7.26 (m, 1H), 7.06 (d, J = 19.3 Hz, 2H), 6.80 (d, J = 9.1 Hz, 1H), 6.71 (s, 1H), 6.50 (dd, J = 17.0, 10.1 Hz, 1H), 6.24 (dd, J = 17.0, 2.0 Hz, 1H), 5.74 (dd, J = 10.2, 2.0 Hz, 1H), 4.75-4.60 (m, 1H), 4.51 (d, J = 6.8 Hz, 4H), 3.91 (p, J = 6.9 Hz, 1H), 3.72 (d, J = 12.1 Hz, 2H), 2.66 (t, J = 12.1 Hz, 2H), 2.41 (d, J = 11.8 Hz, 1H), 2.12 (s, 3H), 1.65 (d, J = 12.0 Hz, 2H), 1.51 (tt, J = 13.5, 6.8 Hz, 2H), 1.27 (d, J = 6.0 Hz, 6H). MS: 583 $[M + H]^+$ |

TABLE 3-continued

| Structures, names and hydrogen NMR and mass spectrometry characterization data of the compounds prepared in Examples 2-81. | | | |
|---|---|---|---|
| No. | Structure | Name | Characterization |
| Example 73. | 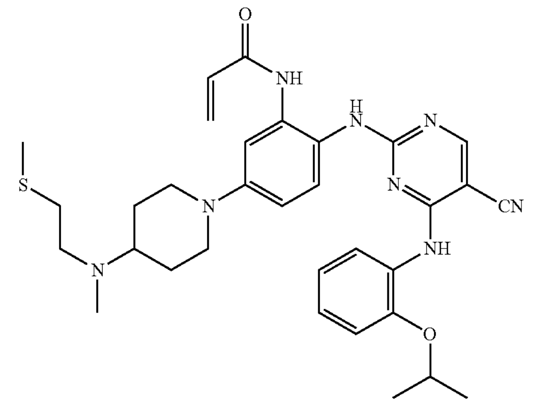 [SMILES: C=CC(=O)Nc1cc(N2CCC(N(C)CCSC)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(methyl(2-(methylthioethyl)amino)piperidin-1-yl)phenyl)acrylamide | $^1$H NMR (400 MHz, DMSO-$d_6$) δ 9.65 (s, 1H), 8.95 (s, 1H), 8.47 (s, 1H), 8.24 (s, 1H), 7.96 (s, 1H), 7.35 (s, 1H), 7.29 (s, 1H), 7.06 (d, J = 17.2 Hz, 2H), 6.81 (dd, J = 8.7, 2.7 Hz, 1H), 6.72 (s, 1H), 6.50 (dd, J = 16.9, 10.2 Hz, 1H), 6.24 (dd, J = 16.9, 2.0 Hz, 1H), 5.74 (dd, J = 10.2, 2.0 Hz, 1H), 4.68-4.60 (m, 1H), 3.72 (d, J = 12.0 Hz, 2H), 2.71 (t, J = 12.5 Hz, 2H), 2.64 (d, J = 7.2 Hz, 2H), 2.56 (dd, J = 8.8, 5.5 Hz, 3H), 2.23 (s, 3H), 2.08 (s, 3H), 1.79 (d, J = 11.8 Hz, 2H), 1.61-1.47 (m, 2H), 1.28 (d, J = 6.0 Hz, 6H). MS: 601 $[M + H]^+$ |
| Example 74. | 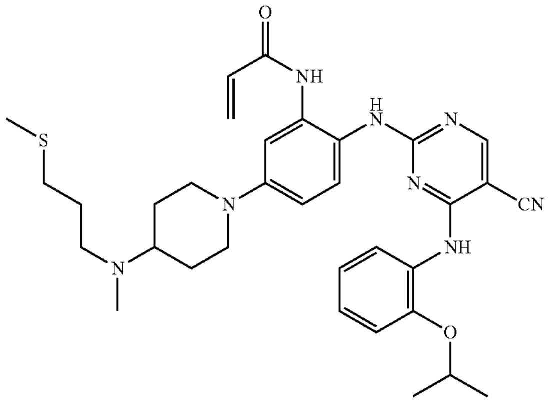 [SMILES: C=CC(=O)Nc1cc(N2CCC(N(C)CCCSC)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(methyl(3-(methylthiopropyl)amino)piperidin-1-yl)phenyl)acrylamide | $^1$H NMR (400 MHz, DMSO-$d_6$) δ 9.66 (s, 1H), 8.95 (s, 1H), 8.47 (s, 1H), 8.24 (s, 1H), 7.96 (s, 1H), 7.35 (s, 1H), 7.31-7.26 (m, 1H), 7.06 (d, J = 16.5 Hz, 2H), 6.81 (dd, J = 9.1, 2.8 Hz, 1H), 6.72 (s, 1H), 6.50 (dd, J = 17.0, 10.2 Hz, 1H), 6.24 (dd, J = 17.0, 2.0 Hz, 1H), 5.74 (dd, J = 10.1, 2.0 Hz, 1H), 4.68-4.60 (m, 1H), 3.72 (d, J = 12.1 Hz, 2H), 2.71 (t, J = 12.0 Hz, 2H), 2.50-2.47 (m, 5H), 2.20 (s, 3H), 2.04 (s, 3H), 1.78 (d, J = 12.1 Hz, 2H), 1.67 (q, J = 7.0 Hz, 2H), 1.61-1.47 (m, 2H), 1.28 (d, J = 6.0 Hz, 6H). MS: 615 $[M + H]^+$ |
| Example 75. | 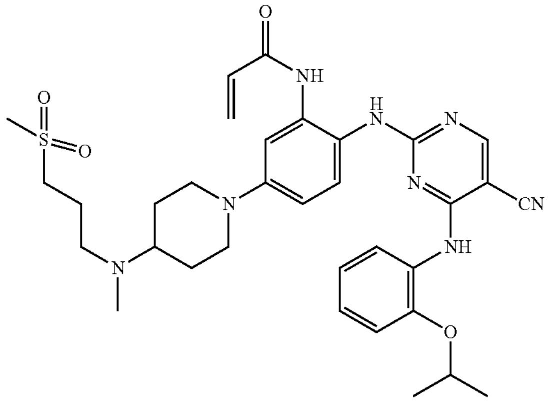 [SMILES: C=CC(=O)Nc1cc(N2CCC(N(C)CCCS(C)(=O)=O)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(methyl(3-(methylsulfonyl)propyl)amino)piperidin-1-yl)phenyl)acrylamide | $^1$H NMR (400 MHz, DMSO-$d_6$) δ 9.65 (s, 1H), 8.95 (s, 1H), 8.47 (s, 1H), 8.24 (s, 1H), 7.96 (s, 1H), 7.35 (s, 1H), 7.29 (s, 1H), 7.08 (s, 2H), 6.85-6.77 (m, 1H), 6.72 (s, 1H), 6.50 (dd, J = 16.9, 10.2 Hz, 1H), 6.24 (dd, J = 17.0, 2.0 Hz, 1H), 5.74 (dd, J = 10.0, 2.0 Hz, 1H), 4.81-4.56 (m, 1H), 3.73 (d, J = 12.1 Hz, 2H), 3.15-3.07 (m, 2H), 2.98 (s, 3H), 2.71 (t, J = 12.1 Hz, 2H), 2.53 (br, 3H), 2.21 (s, 3H), 1.80 (dd, J = 17.6, 9.8 Hz, 4H), 1.56 (t, J = 11.6 Hz, 2H), 1.28 (d, J = 6.0 Hz, 6H). MS: 647 $[M + H]^+$ |

TABLE 3-continued

Structures, names and hydrogen NMR and mass spectrometry characterization data of the compounds prepared in Examples 2-81.

| No. | Structure | Name | Characterization |
|---|---|---|---|
| Example 76. | 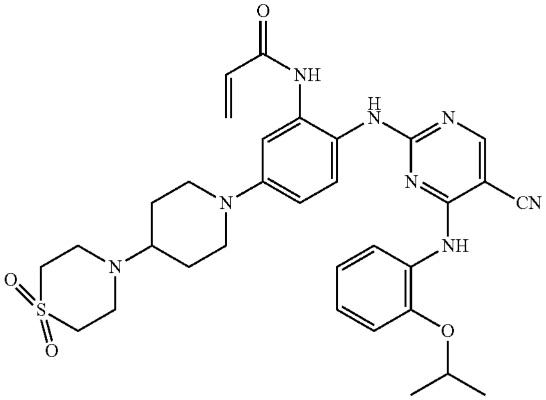 [SMILES: C=CC(=O)Nc1cc(N2CCC(N3CCS(=O)(=O)CC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(1,1-dioxidothiomorpholino)piperidin-1-yl)phenyl)acrylamide | $^1$H NMR (400 MHz, DMSO-$d_6$) δ 9.64 (s, 1H), 8.97 (s, 1H), 8.47 (s, 1H), 8.24 (s, 1H), 7.95 (s, 1H), 7.34-7.25(m, 2H), 7.08 (t, J = 12.4 Hz, 2H), 6.81 (dd, J = 9.2, 2.6 Hz, 1H), 6.71 (s, 1H), 6.50 (dd, J = 16.9, 10.2 Hz, 1H), 6.24 (dd, J = 17.0, 2.0 Hz, 1H), 5.74 (dd, J = 10.0, 2.0 Hz, 1H), 4.70-4.60 (m, 1H), 3.74 (d, J = 12.0 Hz, 2H), 3.11-3.03 (m, 4H), 3.00 (br, 4H), 2.75-2.65 (m, 3H), 1.81 (d, J = 11.7 Hz, 2H), 1.64-1.53 (m, 2H), 1.28 (d, J = 6.0 Hz, 6H), MS: 631 [M + H]$^+$ |
| Example 77. | 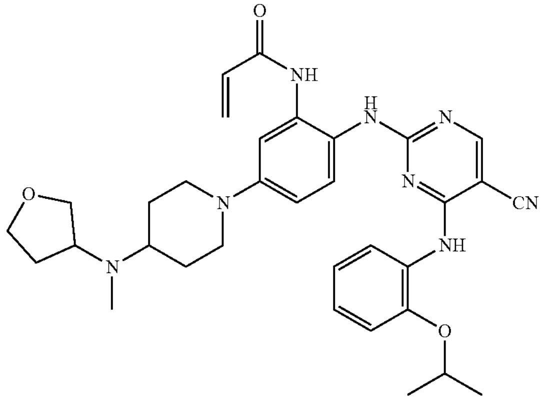 [SMILES: C=CC(=O)Nc1cc(N2CCC(N(C)C3CCOC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(methyl(tetrahydrofuran-3-yl)amino)piperidin-1-yl)phenyl)acrylamide | $^1$H NMR (400 MHz, DMSO-$d_6$) δ 9.65 (s, 1H), 8.96 (s, 1H), 8.47 (s, 1H), 8.24 (s, 1H), 7.96 (s, 1H), 7.35 (s, 1H), 7.32-7.27 (m, 1H), 7.07 (t, J = 11.5 Hz, 2H), 6.84-6.69 (m, 2H), 6.50 (dd, J = 17.0, 10.2 Hz, 1H), 6.24 (dd, J = 17.0, 2.1 Hz, 1H), 5.74 (dd, J = 10.1, 2.0 Hz, 1H), 4.64 (p, J = 6.1 Hz, 1H), 3.88-3.70 (m, 4H), 3.64 (td, J = 8.4, 7.1 Hz, 1H), 3.41 (dt, J = 27.2, 7.3 Hz, 2H), 2.65 (dt, J = 41.3, 12.1 Hz, 3H), 2.13 (s, 3H), 1.97 (dtd, J = 11.6, 7.3, 4.0 Hz, 1H), 1.74 (dq, J = 11.9, 3.9 Hz, 3H), 1.61 (t, J = 12.0 Hz, 2H), 1.28 (d, J = 6.0 Hz, 6H). MS: 597 [M + H]$^+$ |
| Example 78. | 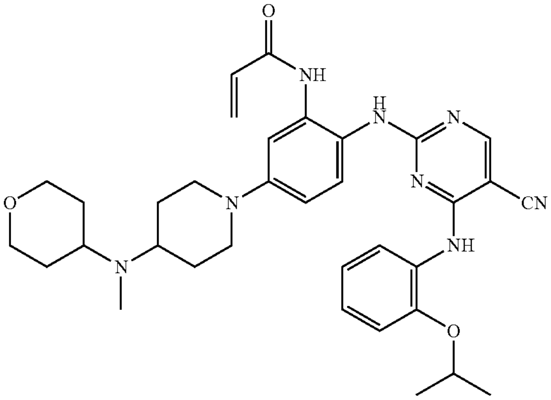 [SMILES: C=CC(=O)Nc1cc(N2CCC(N(C)C3CCOCC3)CC2)ccc1Nc1ncc(C#N)c(Nc2ccccc2OC(C)C)n1] | N-(2-((5-cyano-4-((2-isopropoxyphenyl)amino)pyrimidin-2-yl)amino)-5-(4-(methyl(tetrahydro-2H-pyran-4-yl)amino)piperidin-1-yl)phenyl)acrylamide | $^1$H NMR (400 MHz, DMSO-$d_6$) δ 9.66 (s, 1H), 8.96 (s, 1H), 8.47 (s, 1H), 8.24 (s, 1H), 7.96 (s, 1H), 7.35 (s, 1H), 7.29 (s, 1H), 7.06 (d, J = 19.7 Hz, 2H), 6.84-6.76 (m, 1H), 6.72 (s, 1H), 6.50 (dd, J = 17.0, 10.1 Hz, 1H), 6.24 (dd, J = 17.0, 2.0 Hz, 1H), 5.74 (dd, J = 10.1, 2.0 Hz, 1H), 4.74-4.45 (m, 1H), 3.88 (dd, J = 11.0, 4.2 Hz, 2H), 3.71 (d, J = 12.1 Hz, 2H), 3.29 (dd, J = 11.7, 2.0 Hz, 2H), 2.78-2.67 (m, 4H), 2.19 (s, 3H), 1.76 (d, J = 12.2 Hz, 2H), 1.68-1.42 (m, 6H), 1.28 (d, J = 6.0 Hz, 6H) MS: 611 [M + H]$^+$ |

TABLE 3-continued

Structures, names and hydrogen NMR and mass spectrometry characterization data of the compounds prepared in Examples 2-81.

| No. | Structure | Name | Characterization |
|---|---|---|---|
| Example 79. | 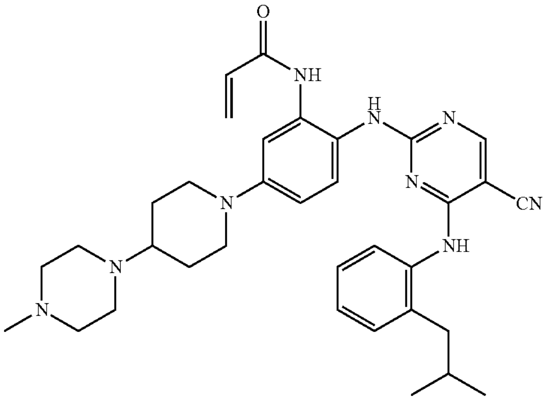 [SMILES: C=CC(=O)Nc1cc(N2CCC(N3CCN(C)CC3)CC2)ccc1Nc1ncc(C#N)c(Nc2ccccc2CC(C)C)n1] | N-(2-((5-cyano-4-((2-isobutylphenyl)amino)pyrimidin-2-yl)amino)-5-(4-(4-methylpiperazin-1-yl)piperidin-1-yl)phenyl)acrylamide | $^1$H NMR (400 MHz, DMSO-$d_6$) δ 9.64 (s, 1H), 9.04 (s, 1H), 8.64 (s, 1H), 8.35 (s, 1H), 7.34-7.11 (m, 5H), 7.04 (s, 1H), 6.71-6.37 (m, 2H), 6.22 (d, J = 17.0 Hz, 1H), 5.79-5.71 (m, 1H), 3.62 (d, J = 12.2 Hz, 2H), 2.64 (t, J = 11.9 Hz, 2H), 2.57 (br, 3H), 2.47-2.37 (m, 8H), 2.22 (s, 3H), 1.84-1.77 (m, 3H), 1.48 (qd, J = 11.9, 3.9 Hz, 2H), 0.80 (d, J = 6.6 Hz, 6H). MS: 594 $[M + H]^+$ |
| Example 80. | 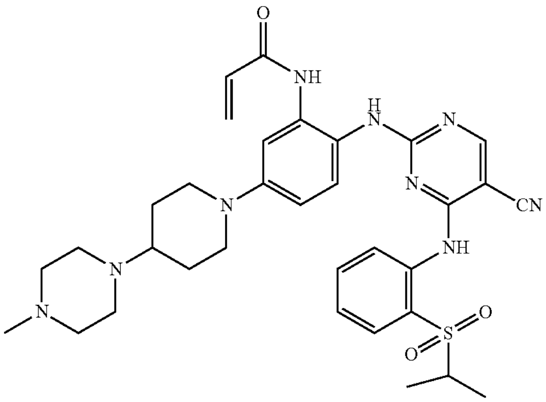 [SMILES: C=CC(=O)Nc1cc(N2CCC(N3CCN(C)CC3)CC2)ccc1Nc1ncc(C#N)c(Nc2ccccc2S(=O)(=O)C(C)C)n1] | N-(2-((5-cyano-4-((2-(isopropylsulfonyl)phenyl)amino)pyrimidin-2-yl)amino)-5-(4-(4-methylpiperazin-1-yl)piperidin-1-yl)phenyl)acrylamide | $^1$H NMR (400 MHz, DMSO-$d_6$) δ 9.63 (br, 2H), 9.09 (s, 1H), 8.54 (s, 1H), 8.26 (s, 1H), 7.82-7.75 (m, 1H), 7.50 (s, 1H), 7.33 (br, 3H), 6.80 (dd, J = 8.9, 2.8 Hz, 1H), 6.50 (dd, J = 16.9, 10.1 Hz, 1H), 6.23 (dd, J = 17.0, 2.0 Hz, 1H), 5.73 (dd, J = 10.0, 2.1 Hz, 1H), 3.70 (d, J = 12.2 Hz, 2H), 3.50-3.30 (m, 5H), 2.70 (t, J = 12.0 Hz, 2H), 2.49 (br, 1H), 2.40-2.26 (m, 4H), 2.15 (s, 3H), 1.89-1.80 (m, 2H), 1.49 (qd, J = 12.1, 3.8 Hz, 2H), 1.14 (d, J = 6.7 Hz, 6H). MS: 644 $[M + H]^+$ |
| Example 81. | 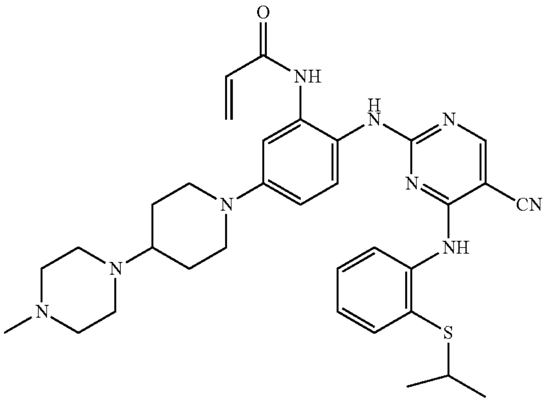 [SMILES: C=CC(=O)Nc1cc(N2CCC(N3CCN(C)CC3)CC2)ccc1Nc1ncc(C#N)c(Nc2ccccc2SC(C)C)n1] | N-(2-((5-cyano-4-((2-(isopropylthiophenyl)amino)pyrimidin-2-yl)amino)-5-(4-(4-methylpiperazin-1-yl)piperidin-1-yl)phenyl)acrylamide | $^1$H NMR (400 MHz, DMSO-$d_6$) δ 9.68 (s, 1H), 9.01 (d, J = 4.0 Hz, 2H), 8.49 (s, 1H), 7.99 (s, 1H), 7.54 (d, J = 7.4 Hz, 1H), 7.33 (s, 2H), 7.13 (s, 2H), 6.77 (dd, J = 8.9, 2.8 Hz, 1H), 6.50 (dd, J = 16.9, 10.2 Hz, 1H), 6.23 (dd, J = 17.0, 2.1 Hz, 1H), 5.74 (dd, J = 10.1, 2.1 Hz, 1H), 3.70 (d, J = 12.1 Hz, 2H), 3.24 (br, 5H), 2.70 (t, J = 11.5 Hz, 2H), 2.61 (br, 5H), 2.29 (s, 3H), 1.86 (d, J = 11.9 Hz, 2H), 1.51 (d, J = 11.2 Hz, 2H), 1.19 (d, J = 6.6 Hz, 6H). MS: 612 $[M + H]^+$ |

Example 82: N-(2-((5-cyano-4-((2-isopropoxyphenyl)amino)pyridin-2-yl)amino)-5-(4-(dimethylamino)piperidin-1-yl)phenyl)acrylamide

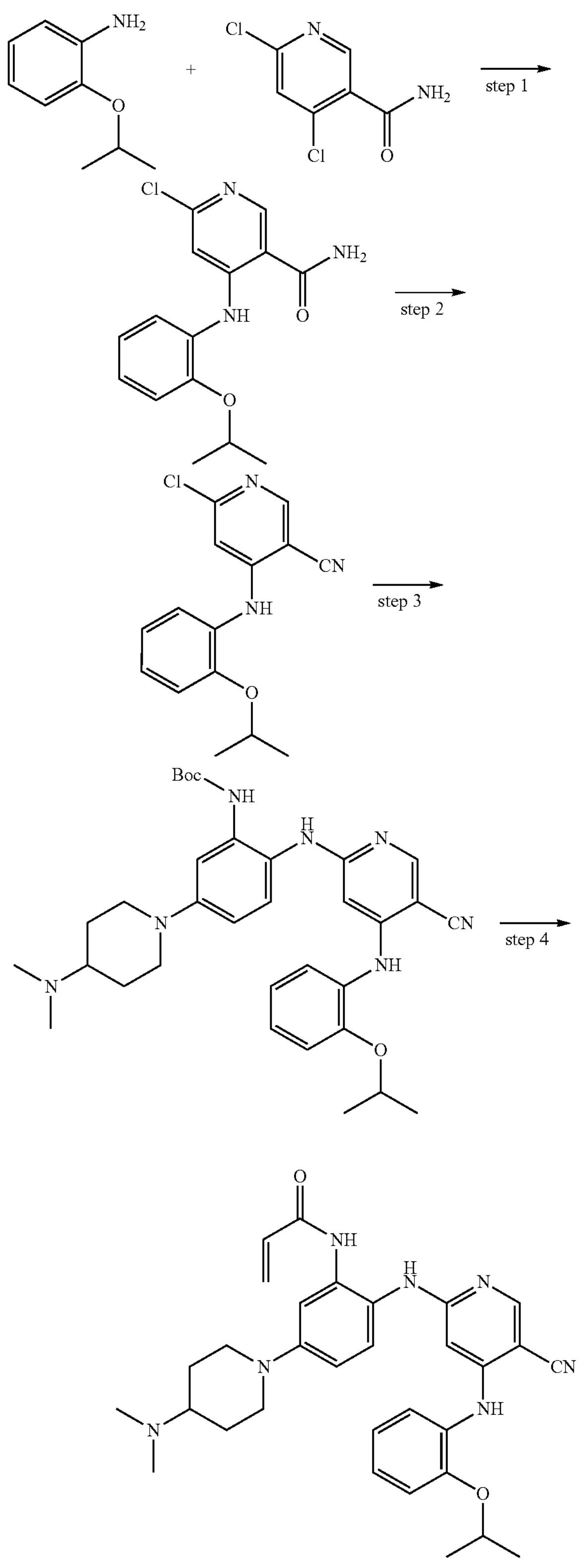

Step 1) Preparation of 6-chloro-4-((2-isopropoxyphenyl)amino)nicotinamide

HMDSNa (2N, 1 mL) was slowly added dropwise to a solution of 2-isopropoxyaniline (300 mg, 2 mmol) in tetrahydrofuran (5 mL) under ice-salt bath, and the mixture was reacted with stirring for another half an hour. A solution of 2,4-dichloro-5-nicotinamide (190 mg, 1 mmol) in tetrahydrofuran (1 mL) was then added dropwise, and the mixture was reacted with stirring overnight in an ice-water bath. The reaction solution was quenched by adding water, and slurried. The slurry was filtered to give 230 mg of a pale yellow solid with a yield of 75%, MS: 306 $[M+H]^+$.

Step 2) Preparation of 6-chloro-4-((2-isopropoxyphenyl)amino)nicotinonitrile

A solution of 6-chloro-4-((2-isopropoxyphenyl)amino) nicotinamide (220 mg, 0.8 mmol) in phosphorus oxychloride (2 mL) was heated to reflux and reacted for 3 hours. The reaction solution was cooled, concentrated, washed with saturated sodium bicarbonate, and extracted with dichloromethane. The organic phase was dried, and concentrated to give 160 mg of a yellow solid, MS: 288 $[M+H]^+$.

Step 3) Preparation of tert-butyl (2-((5-cyano-4-((2-isopropoxyphenyl)amino)pyridin-2-yl)amino)-5-(4-(dimethylamino)piperidin-1-yl)phenyl)carbamate 6-Chloro-4-((2-isopropoxyphenyl)amino)nicotinonitrile (120 mg, 0.4 mmol), tert-butyl (2-amino-5-(4-(dimethylamino)piperidin-1-yl)phenyl)carbamate (135 mg, 0.4 mmol), $Pd_2(dba)_3$ (10 mg), Xantphos (10 mg) and sodium carbonate (110 mg, 1 mmol) were dissolved in dioxane (5 mL) and water (0.5 mL) in a sealed tube, respectively, and the atmosphere of the reaction system was replaced with argon gas. The mixture was then reacted with heating at 120° C. for 10 hours. The reaction solution was cooled, and filtered. The filtrate was concentrated and then directly purified by a preparative thin-layer plate (1 mm, silica gel) to give 104 mg of product as a pale yellow solid, MS: 586 $[M+H]^+$.

Step 4): Tert-butyl (2-((5-cyano-4-((2-isopropoxyphenyl) amino)pyridin-2-yl)amino)-5-(4-(dimethylamino)piperidin-1-yl)phenyl)carbamate (88 mg, 0.15 mmol) was added to a solution of trifluoroacetic acid (1 mL) in dichloromethane (3 mL), and the mixture was stirred at room temperature for 1 hour. The reaction solution was concentrated, and anhydrous tetrahydrofuran (2 mL) was added. Acryloyl chloride (40 μL) was then added dropwise under an ice-water bath. The reaction solution was stirred for another half an hour, then quenched by adding water, extracted with dichloromethane, and washed with saturated sodium bicarbonate. The organic phase was dried, concentrated and purified by a preparative thin-layer plate (0.5 mm, loaded with silica gel) with eluting system of $V_{dichloromethane/methanol}$=11/1 to give 33 mg of product as a white solid. $^1H$ NMR (400 MHz, DMSO-$d_6$) δ 9.53 (s, 1H), 8.23 (s, 1H), 8.18 (s, 1H), 7.80 (s, 1H), 7.30 (d, J=2.7 Hz, 1H), 7.26-7.05 (m, 4H), 6.93 (td, J=7.5, 1.5 Hz, 1H), 6.74 (dd, J=8.9, 2.8 Hz, 1H), 6.45 (dd, J=17.0, 10.1 Hz, 1H), 6.20 (dd, J=17.0, 2.0 Hz, 1H), 5.85 (s, 1H), 5.72 (dd, J=10.1, 2.0 Hz, 1H), 4.56 (p, J=6.1 Hz, 1H), 3.66 (d, J=12.4 Hz, 2H), 2.71-2.60 (m, 2H), 2.53 (s, 1H), 2.37 (s, 6H), 1.89 (d, J=11.1 Hz, 2H), 1.54 (dd, J=13.8, 10.0 Hz, 2H), 1.20 (d, J=6.0 Hz, 6H). MS:540 $[M+H]^+$.

Example 83: N-(2-((5-cyano-4-((2-isopropoxyphenyl)amino)pyridin-2-yl)amino)-5-(4-(4-methylpiperazin-1-yl)piperidin-1-yl)phenyl)acrylamide

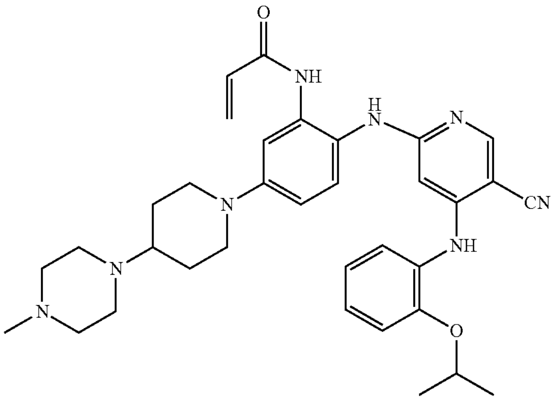 [SMILES: C=CC(=O)Nc1cc(N2CCC(N3CCN(C)CC3)CC2)ccc1Nc1cc(Nc2ccccc2OC(C)C)c(C#N)cn1]

The title product was obtained through the same procedures as those in Example 82 by replacing tert-butyl (2-amino-5-(4-(dimethylamino)piperidin-1-yl)phenyl)carbamate in Step 3) in Example 82 with tert-butyl (2-amino-5-(4-(4-methylpiperazin-1-yl)piperidin-1-yl)phenyl)carbamate; $^1H$ NMR (400 MHz, DMSO-$d_6$) δ 9.53 (s, 1H), 8.21 (s, 1H), 8.16 (s, 1H), 7.80 (s, 1H), 7.29 (d, J=2.8 Hz, 1H), 7.25-7.05 (m, 4H), 6.93 (td, J=7.5, 1.5 Hz, 1H), 6.72 (dd, J=8.9, 2.8 Hz, 1H), 6.45 (dd, J=16.9, 10.2 Hz, 1H), 6.20 (dd, J=17.0, 2.1 Hz, 1H), 5.83 (s, 1H), 5.72 (dd, J=10.1, 2.0 Hz, 1H), 4.61-4.50 (m, 1H), 3.63 (d, J=12.3 Hz, 2H), 3.35 (br, 4H), 2.65 (td, J=12.2, 2.2 Hz, 2H), 2.55-2.50 (m, 1H), 2.41-2.21 (m, 4H), 2.16 (s, 3H), 1.83 (d, J=12.3 Hz, 2H), 1.47 (dd, J=11.7, 3.6 Hz, 2H), 1.20 (d, J=6.1 Hz, 6H). MS:595$[M+H]^+$.

Example 84: N-(2-((5-cyano-4-((2-isopropoxyphenyl)amino)pyridin-2-yl)amino)-5-(4-ethylpiperazin-1-yl)phenyl)acrylamide

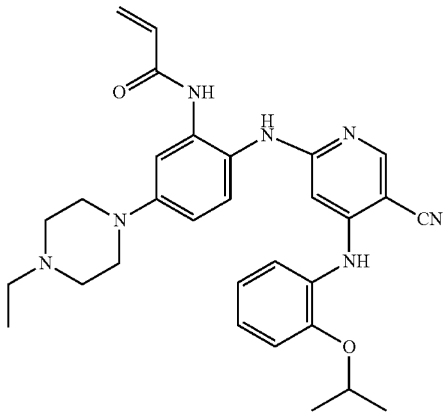 [SMILES: C=CC(=O)Nc1cc(N2CCN(CC)CC2)ccc1Nc1cc(Nc2ccccc2OC(C)C)c(C#N)cn1]

The title product was obtained through the same procedures as those in Example 82 by replacing tert-butyl (2-amino-5-(4-(dimethylamino)piperidin-1-yl)phenyl)carbamate in Step 3) in Example 82 with tert-butyl (2-amino-5-(4-ethylpiperazin-1-yl)phenyl)carbamate; $^1H$ NMR (400

MHz, DMSO-$d_6$) δ 9.55 (s, 1H), 8.22-8.14 (m, 2H), 7.80 (s, 1H), 7.31-7.05 (m, 5H), 6.93 (td, J=7.5, 1.5 Hz, 1H), 6.74 (dd, J=8.9, 2.8 Hz, 1H), 6.45 (dd, J=17.0, 10.1 Hz, 1H), 6.20 (dd, J=17.0, 2.0 Hz, 1H), 5.85 (s, 1H), 5.72 (dd, J=10.1, 2.0 Hz, 1H), 4.56 (p, J=6.0 Hz, 1H), 3.08 (t, J=5.0 Hz, 4H), 2.50 (br, 4H), 2.38 (q, J=7.2 Hz, 2H), 1.20 (d, J=6.0 Hz, 6H), 1.04 (t, J=7.2 Hz, 3H). MS:526$[M+H]^+$.

Assay Example 1

Assay of activity of small molecule compounds on inhibiting FGFR4 kinase and FGFR4 V550L mutant kinase. The assay method was as follows:

1) Dilution of Compounds:

In a 96-well plate a, the compounds were serially diluted 3-fold with DMSO to form 11 concentrations, and the 12th concentration was pure DMSO (as a positive control); In a new 96-well plate b, the above solutions were diluted 25-fold with ultrapure water (DMSO concentration was 4%).

2) Transferring Compounds to a 384-Well Plate:

The above solutions of compounds diluted with ultrapure water in the 96-well plate b were pipetted into corresponding wells of a 384-well plate.

3) Adding 4× kinase solution: 2.5 μl of the above 4× kinase solutions were pipetted with a multi-channel pipette into corresponding reaction wells of the 384-well plate, and the mixture was mixed well and pre-reacted at room temperature for 5 minutes.

4) Adding 2× substrate/ATP mixture: 5 μl of the above 2× substrate/ATP mixtures were pipetted with a multi-channel pipette into corresponding reaction wells of the 384-well plate.

5) Negative control: negative control wells were set up in the 384-well plate by adding 2.5 μl of 4× substrate, 2.5 μl of 4× enzyme solution, 2.5 μl of 1× kinase Assay Buffer and 2.5 μl of ultrapure water containing 4% DMSO to each well.

6) Centrifuging, mixing well, and reacting at room temperature in the dark for 2 hours.

7) Terminating the Enzymatic Reaction:

5 μl of the above 4× stop solutions were pipetted into corresponding wells of the 384-well plate, and the mixture was centrifuged, mixed well, and then reacted at room temperature for 5 minutes.

8) Development of the Reaction:

5 μl of the above 4× detection solutions were pipetted into corresponding wells of the 384-well plate, and the mixture was centrifuged, mixed well, and then reacted at room temperature for 1 hour.

9) The 384-well plate was placed into a plate reader, and the signal was detected using the appropriate program.

10) Analysis of $IC_{50}$:

Reading of well=10000*EU665 value/EU615 value

Inhibition rate=(reading of positive control well−reading of assay well)/(reading of positive control well−reading of negative control well)*100%

The corresponding $IC_{50}$ can be calculated by inputting the drug concentrations and corresponding inhibition rates into GraphPad Prism 5 and processing.

Assay Conditions for Screening FGFR4 Kinase Activity Inhibitory Molecule:

The final concentration of FGFR4 kinase in the reaction system was 3.85 nM, the final concentration of ATP was 100 μM, the final concentration of substrate ULight™-labeled JAK-1 (Tyr1023) Peptide was 100 nM, and the time for enzymatic reaction was 2 hours.

The highest final concentration of the compound in the reaction system was 2.5 μM. After serial 3-fold dilution, there were 11 concentrations in total, and the lowest final concentration was 0.042 nM. The final concentration of DMSO was 1%.

Assay Conditions for Screening FGFR4 V550L Kinase Activity Inhibitory Molecule:

The final concentration of FGFR4 V550L kinase in the reaction system was 1 nM, the final concentration of ATP was 10 μM, the final concentration of substrate ULight™-labeled PolyGT was 100 nM, and the time for enzymatic reaction was 2 hours.

The highest final concentration of the compound in the reaction system was 2.5 μM. After seral 3-fold dilution, there were 11 concentrations in total, and the lowest final concentration was 0.042 nM. The final concentration of DMSO was 1%.

Assay results of inhibitory activity of some compounds disclosed herein on tyrosine kinase FGFR4 and tyrosine kinase FGFR4 with V550L mutant are listed in Table 4, wherein A indicates that $IC_{50}$ is less than or equal to 10 nM, B indicates that $IC_{50}$ is greater than 10 nM but less than or equal to 50 nM, C indicates that $IC_{50}$ is greater than 50 nM but less than or equal to 100 nM, and D indicates that $IC_{50}$ is greater than 100 nM but less than or equal to 1000 nM. NT means no relevant value.

TABLE 4

Assay results of inhibitory activity of compounds of the present disclosure on FGFR4 kinase and tyrosine kinase FGFR4 with V550L mutant

| Example No. | FGFR4 $IC_{50}$ nM | FGFR4 V550L $IC_{50}$ nM |
|---|---|---|
| 1 | B | A |
| 2 | B | A |
| 3 | B | A |
| 4 | B | A |
| 5 | C | B |
| 6 | A | A |
| 7 | C | B |
| 8 | B | A |
| 9 | B | B |
| 10 | B | B |
| 11 | B | NT |
| 12 | B | B |
| 13 | B | B |
| 14 | C | B |
| 15 | C | B |
| 16 | B | A |
| 17 | B | B |
| 18 | B | B |
| 19 | D | B |
| 20 | B | B |
| 21 | B | B |
| 22 | D | D |
| 23 | C | A |
| 24 | B | B |
| 25 | C | B |
| 26 | D | D |
| 27 | A | A |
| 28 | A | A |
| 29 | B | B |
| 30 | B | A |
| 31 | A | B |
| 32 | NT | B |
| 33 | A | B |
| 34 | C | B |
| 35 | B | B |
| 36 | B | B |
| 37 | A | A |

TABLE 4-continued

Assay results of inhibitory activity of compounds of the present disclosure on FGFR4 kinase and tyrosine kinase FGFR4 with V550L mutant

| Example No. | FGFR4 $IC_{50}$ nM | FGFR4 V550L $IC_{50}$ nM |
|---|---|---|
| 38 | C | C |
| 39 | A | A |
| 40 | B | B |
| 41 | B | A |
| 42 | A | A |
| 43 | B | B |
| 44 | B | B |
| 45 | B | B |
| 46 | B | B |
| 47 | B | B |
| 48 | B | B |
| 49 | A | A |
| 50 | B | A |
| 51 | D | B |
| 52 | A | A |
| 53 | C | A |
| 54 | B | A |
| 55 | B | A |
| 56 | B | A |
| 57 | B | A |
| 58 | B | A |
| 59 | B | A |
| 60 | B | A |
| 61 | B | A |
| 62 | B | B |
| 63 | A | B |
| 64 | B | B |
| 65 | B | A |
| 66 | A | B |
| 67 | B | A |
| 68 | A | A |
| 69 | A | A |
| 70 | C | A |
| 71 | A | C |
| 72 | A | B |
| 73 | A | A |
| 74 | A | A |
| 75 | A | A |
| 76 | B | B |
| 77 | A | A |
| 78 | A | A |
| 79 | B | C |
| 80 | A | A |
| 81 | A | A |
| 82 | B | NT |
| 83 | B | NT |
| 84 | B | NT |

Assay Example 2

Compounds were assayed for inhibiting cell proliferation, and the specific method was as follows:

1. Cells were cultured to a logarithmic growth phase, pipetted evenly, transferred to a 15 mL centrifuge tube, and centrifuged at 1000 rpm at room temperature for 4 minutes;
2. The supernatant was discarded; 5 mL of complete medium was added and pipetted evenly; 10 μL of cell suspension was weighed, mixed well with 10 μL of 0.4% trypan blue, and counted under a cell counter; the proportion of living cells was ensured to be above 90%;
3. The cell suspension was seeded into a 96-well plate (80 μL of cell suspension per well) according to the conditions shown in Table 5; in the outer 36 wells of the 96-well plate, no cells were added but only sterile water was added; only the inner 60 wells were used for cell assay and control;

4. 5× compound dilution: the compounds were serially diluted 4-fold to give a total of 9 concentrations; 80-fold overall dilution was completed with complete medium, the resulting concentration was 5 times the final drug concentration, and DMSO concentration was 1.25%;
5. 20 μL of the corresponding compounds with different concentrations were added to each well of assay wells of the 96-well plate; 20 μL of complete medium was added to positive and negative control wells and shaken well; and the final concentration of DMSO in each well was 0.25%;
6. After 72 hours of incubation, 10 μL of CCK-8 reagent was added to each well and further incubated at 37° C. for 1-2 hours; and the OD value was read at 450 nm;

7. Cell survival rate (%)=[(As−Ab)/(Ac−Ab)]*100%

As: Assay well (medium containing cells, CCK-8, compound)
Ac: Control well (medium containing cells, CCK-8)
Ab: Blank well (medium without cell and compound, CCK-8)
8. The values were imported into Graphpad Prism 5 software for $IC_{50}$ calculation.

TABLE 5

Basic information and seeding conditions of cells

| Cell name | Source | Medium | Seeding density |
|---|---|---|---|
| Ba/F3 ETV6-FGFR4 | KYinno Biotechnology (Beijing) Co., Ltd. | RPMI 1640 + 10% FBS | 10000/well |
| Ba/F3 ETV6-FGFR4-V550L | KYinno Biotechnology (Beijing) Co., Ltd. | RPMI 1640 + 10% FBS | 10000/well |

Assay results of inhibitory activity of some compounds disclosed herein on the proliferation of Ba/F3 ETV6-FGFR4 cells and Ba/F3 ETV6-FGFR4-V550L cells are listed in Table 6, wherein A indicates that $IC_{50}$ is less than or equal to 10 nM, B indicates that $IC_{50}$ is greater than 10 nM but less than or equal to 50 nM, C indicates that $IC_{50}$ is greater than 50 nM but less than or equal to 100 nM, and D indicates that $IC_{50}$ is greater than 100 nM but less than or equal to 1000 nM. NT means no relevant value.

TABLE 6

Assay results of inhibitory activity of the compounds of the present disclosure on the proliferation of Ba/F3 ETV6-FGFR4 cells and Ba/F3 ETV6-FGFR4-V550L cells

| Example No. | Ba/F3 ETV6-FGFR4 $IC_{50}$ nM | Ba/F3 ETV6-FGFR4-V550L $IC_{50}$ nM |
|---|---|---|
| 1 | A | A |
| 2 | A | A |
| 3 | A | A |
| 4 | A | A |
| 5 | A | A |
| 6 | A | A |
| 7 | A | B |
| 8 | A | A |
| 9 | NT | NT |
| 10 | A | B |
| 11 | B | B |
| 12 | NT | NT |
| 13 | A | B |
| 14 | A | A |
| 15 | A | A |
| 16 | A | A |
| 17 | A | A |
| 18 | A | A |
| 19 | A | A |
| 20 | A | A |
| 21 | A | B |
| 22 | D | D |
| 23 | A | A |
| 24 | B | A |
| 25 | B | B |
| 26 | D | D |
| 27 | A | A |
| 28 | D | C |
| 29 | A | A |
| 30 | A | A |
| 31 | A | A |
| 32 | A | B |
| 33 | A | A |
| 34 | B | B |
| 35 | B | B |
| 36 | B | B |
| 37 | A | A |
| 38 | B | B |
| 39 | A | A |
| 40 | A | A |
| 41 | D | D |
| 42 | A | A |
| 43 | A | A |
| 44 | A | A |
| 45 | A | A |
| 46 | A | A |
| 47 | A | A |
| 48 | A | A |
| 49 | A | A |
| 50 | A | A |
| 51 | A | A |
| 52 | D | D |
| 53 | A | A |
| 54 | A | A |
| 55 | A | A |
| 56 | A | A |
| 57 | A | A |
| 58 | A | A |
| 59 | A | A |
| 60 | A | A |
| 61 | A | A |
| 62 | A | A |
| 63 | A | A |
| 64 | A | A |
| 65 | A | A |
| 66 | A | A |
| 67 | A | A |
| 68 | A | A |
| 69 | A | A |
| 70 | A | A |
| 71 | A | B |
| 72 | A | A |
| 73 | A | A |
| 74 | A | B |
| 75 | A | A |
| 76 | A | A |
| 77 | A | A |
| 78 | A | A |
| 79 | B | B |
| 80 | A | A |
| 81 | A | A |
| 82 | NT | NT |
| 83 | NT | NT |
| 84 | NT | NT |

The biological data provided by the present disclosure indicate that the compounds disclosed herein are useful for treating or preventing diseases caused by abnormalities of FGFR4 kinase, including diseases caused by FGFR4 gene mutations (V550L, V550M, etc.), including primary and metastatic cancers, including solid tumors. Such cancers include, but are not limited to, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myelocytic leukemia, non-Hodgkin's lymphoma, nasopharyngeal cancer, esophageal cancer, brain tumor, B-cell and T-cell lymphoma, lymphoma, multiple myeloma, biliary tract cancerous sarcoma, and cholangiocarcinoma. The compounds disclosed herein can also treat cancers that are resistant to one or more other therapeutic methods. The compounds disclosed herein can also be useful in the treatment of FGFR4 kinase-related diseases other than cancer, including but not limited to ocular fundus diseases, psoriasis, rheumatic arthritis, atherosclerosis, pulmonary fibrosis, and liver fibrosis. The compounds disclosed herein can be used as monotherapy or combination therapy, and can be used in combination with multiple compounds disclosed herein or in combination with drugs other than compounds disclosed herein.

The above-mentioned embodiments are alternative embodiments of the present disclosure. It should be pointed out that for those skilled in the art, without departing from the principles of the present disclosure, several improvements and modifications can also be made to the embodiments of the present disclosure, and these improvements and modifications should also be regarded as within the protection scope of the present disclosure.

What is claimed is:

1. A compound represented by formula (I), or a stereoisomer, a tautomer, a hydrate, a solvate, or a pharmaceutically acceptable salt thereof, Formula (I)

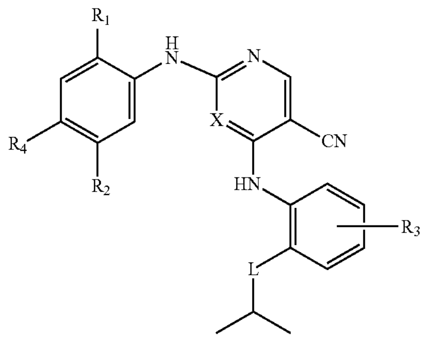

in formula (I),

X is N or CH;

L is —O—, —S—,

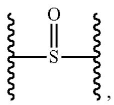,

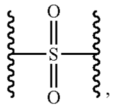,

-continued

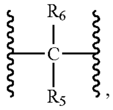,

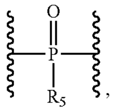, or $—NR_5—$, wherein $R_5$ and $R_6$ are each independently hydrogen, methyl, ethyl, propyl or isopropyl;

$R_1$ is

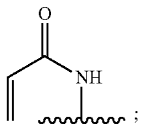 [SMILES: *NC(=O)C=C];

$R_2$ is hydrogen, halogen, $C_1$-$C_3$ alkoxy, or $C_1$-$C_3$ alkyl;

$R_3$ is selected from hydrogen, halogen, hydroxyl, amino, cyano, carboxyl, $C_1$-$C_6$ alkyl, $C_1$-$C_6$ haloalkyl, $C_1$-$C_3$ haloalkoxy, $C_3$-$C_6$ cycloalkyl, $C_2$-$C_3$ alkynyl, $C_2$-$C_3$ alkenyl, $C_1$-$C_3$ alkoxy, $C_1$-$C_3$ alkylthio, mono- or di-$C_1$-$C_3$ alkylamino, $C_3$-$C_4$ cycloalkyloxy, $C_3$-$C_4$ cycloalkyl-substituted $C_1$-$C_3$ alkyl, cyano-substituted $C_1$-$C_3$ alkyl, carbamoyl-substituted $C_1$-$C_3$ alkyl, or the following groups:

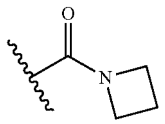,

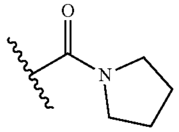,

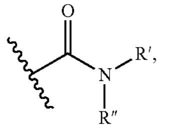

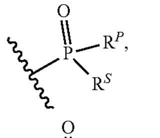

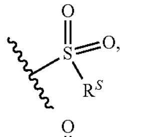

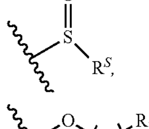

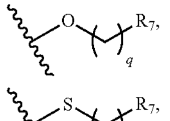

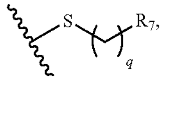

-continued

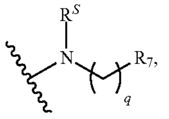

q is an integer of 1-3, $R^s$ is selected from —H, or $C_1$-$C_3$ alkyl, and $R^p$ is selected from —H, or $C_1$-$C_3$ alkyl, R' and R'' are each independently —H, $C_1$-$C_3$ alkyl, or $C_3$-$C_4$ cycloalkyl, $R_7$ is selected from —H, halogen, hydroxyl, cyano, amino, carboxyl, $C_1$-$C_3$ alkyl, $C_3$-$C_4$ cycloalkyl, $C_1$-$C_3$alkoxy, or mono- or di-$C_1$-$C_3$ alkyl-substituted amino;

$R_4$ is -$T_1$-$R_8$ or -$T_2$-$R_9$, $T_1$ is:

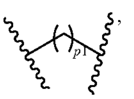
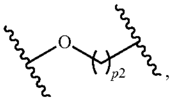
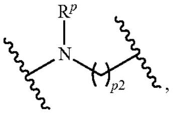

$T_2$ is:

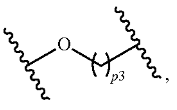
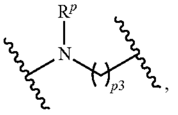

p1 is an integer of 0-4, p2 is an integer of 2-4, and p3 is an integer of 0-1, $R^p$ is —H or $C_1$-$C_3$ alkyl, $R_8$ is selected from —H, halogen, hydroxyl, amino, cyano, $C_1$-$C_6$ alkyl, $C_1$-$C_6$ haloalkyl, $C_1$-$C_3$ haloalkoxy, $C_3$-$C_6$ cycloalkyl, $C_1$-$C_3$ alkoxy, $C_1$-$C_3$ alkylthio, mono- or di-$C_1$-$C_3$ alkylamino, or a 4- to 6-membered heteroalicyclic group, wherein the 4- to 6-membered heteroalicyclic group is unsubstituted or substituted with 1-2 identical or different substituents selected from hydroxyl, $C_1$-$C_6$ alkyl, $C_1$-$C_3$ alkoxy, formyl, acetyl, propionyl, isopropionyl, hydroxyl-substituted $C_1$-$C_3$ alkyl, carboxy-substituted $C_1$-$C_3$ alkyl, oxo, $C_1$-$C_3$ alkyl-substituted or unsubstituted 4- to 6-membered heteroalicyclic group, or —$NR^{10}R^{11}$, $R^{10}$ and $R^{11}$ are each independently selected from —H, $C_1$-$C_6$ alkyl, $C_3$-$C_4$ cycloalkyl, hydroxyl-substituted $C_2$-$C_6$ alkyl, cyano-substituted $C_1$-$C_2$ alkyl, $C_1$-$C_3$ alkoxy-substituted $C_1$-$C_3$ alkyl, $C_1$-$C_3$ alkylthio-substituted $C_1$-$C_3$ alkyl, $C_1$-$C_3$ haloalkyl, methylsulfonyl-substituted $C_1$-$C_3$ alkyl, mono- or di-$C_1$-$C_3$ alkylamino-substituted $C_1$-$C_3$ alkyl, or $C_1$-$C_3$ alkyl-substituted or unsubstituted 4- to 6-membered heteroalicyclic group, or $R^{10}$ and $R^{11}$ together with the nitrogen atom to which they are attached form a 4- to 6-membered heteroalicyclic group, wherein the 4- to 6-membered heteroalicyclic group is unsubstituted or substituted with 1-2 identical or different substituents selected from —H, hydroxyl, oxo, halogen, $C_1$-$C_3$ alkoxy-substituted $C_1$-$C_3$ alkyl, $C_1$-$C_3$ alkylsulfonyl, cyano, amino, $C_1$-$C_3$ acyl, $C_1$-$C_3$ alkyl, mono- or di-$C_1$-$C_3$ alkylamino, hydroxyl-substituted $C_2$-$C_3$ alkyl, or $C_1$-$C_3$ alkoxy, the 4- to 6-membered heteroalicyclic group contains 1-2 heteroatoms selected from N, O or S;

$R^9$ is selected from —H, $C_1$-$C_6$ alkyl, $C_3$-$C_6$ cycloalkyl, or a 4- to 6-membered heteroalicyclic group, wherein the 4- to 6-membered heteroalicyclic group is unsubstituted or substituted with 1-2 identical or different substituents selected from hydroxyl, $C_1$-$C_3$ alkyl, $C_1$-$C_3$ alkoxy, formyl, acetyl, propionyl, or isopropionyl, the 4- to 6-membered heteroalicyclic group in $R^9$ contains 1-2 heteroatoms selected from N, O or S; and, when $R^1$ is

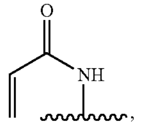 [SMILES: *NC(=O)C=C]

$R_4$ is 4-ethyl-piperazin-1-yl, and L is —O— or

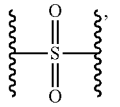 [SMILES: *S(*)(=O)=O]

$R_2$ and $R_3$ are not both hydrogen.

2. The compound of formula (I) according to claim 1, or a stereoisomer, a tautomer, a hydrate, a solvate, or a pharmaceutically acceptable salt thereof, wherein $R_2$ is —H, —F, —Cl, methyl or methoxy.

3. The compound of formula (I) according to claim 1, or a stereoisomer, a tautomer, a hydrate, a solvate, or a pharmaceutically acceptable salt thereof, wherein $R_3$ is selected from —H, —F, —Cl, —Br, hydroxyl, carboxyl, cyano, methyl, ethyl, propyl, isopropyl, tert-butyl, methoxy, ethoxy, propoxy, isopropoxy, cyclopropyloxy, cyclobutyloxy, methylthio, ethylthio, propylthio, isopropylthio, fluoromethyl, difluoromethyl, trifluoromethyl, fluoromethoxy, difluoromethoxy, trifluoromethoxy, ethynyl, ethenyl, cyclopropyl, cyclobutyl, cyclopropylmethyl, cyclobutylmethyl, amino, methylamino, ethylamino, dimethylamino, diethylamino, N-methyl-N-ethylamino, or the following groups:

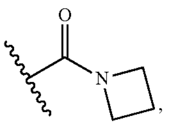
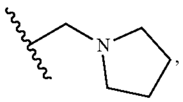
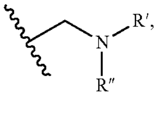
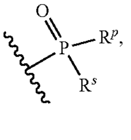

-continued

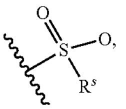

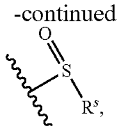

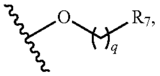

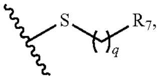

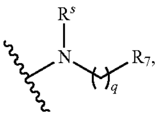

q is an integer of 2-3, $R^s$ is selected from —H, methyl, or ethyl, and $R^p$ is selected from —H, methyl, or ethyl, R' and R" are each independently selected from —H, methyl, ethyl, propyl, isopropyl, cyclopropyl, or cyclobutyl, $R_7$ is selected from —H, —F, hydroxyl, cyano, carboxyl, amino, methyl, ethyl, propyl, isopropyl, methoxy, ethoxy, propoxy, isopropoxy, methylamino, ethylamino, or dimethylamino.

4. The compound of formula (I) according to claim 1, or a stereoisomer, a tautomer, a hydrate, a solvate, or a pharmaceutically acceptable salt thereof, wherein $R^4$ is $-T_1-R_8$, $T_1$ is selected from:

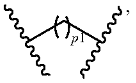

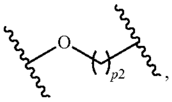

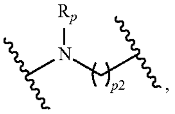

p1 is an integer of 0-3, and p2 is an integer of 2-3;

$R^p$ is selected from —H, methyl, or ethyl;

$R^8$ is selected from —H, —F, —Cl, hydroxyl, amino, cyano, fluoromethoxy, difluoromethoxy, trifluoromethoxy, methyl, ethyl, propyl, butyl, hexyl, isopropyl, fluoromethyl, difluoromethyl, trifluoromethyl, cyclopropyl, cyclobutyl, cyclopentyl, cyclohexyl, methoxy, ethoxy, propoxy, butoxy, isopropoxy, methylthio, ethylthio, propylthio, isopropylthio, methylamino, ethylamino, propylamino, dimethylamino, diethylamino, N-methyl-N-ethylamino or the following groups:

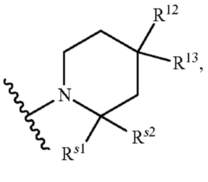

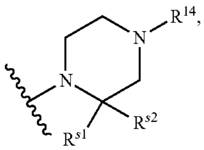

-continued

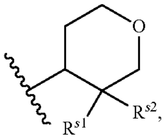

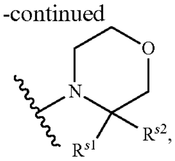

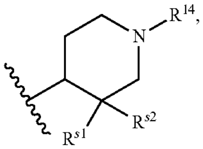

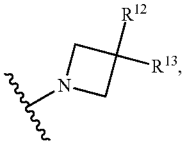

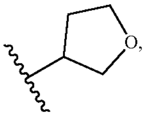

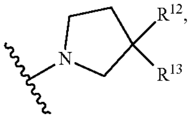

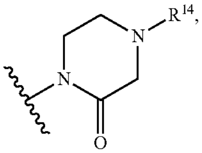

$R^{12}$ is —H, —F, methyl, or ethyl, $R^{13}$ is —H, —F, hydroxyl, hydroxymethyl, cyano, methyl, ethyl, methoxy, or $—NR^5R^{16}$, $R^{14}$ is —H, —F, methyl, ethyl, propyl, isopropyl, or

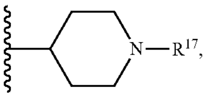

wherein $R^{17}$ is —H, —F, methyl, ethyl, propyl, or isopropyl, $R^{s1}$ and $R^{s2}$ are each independently selected from H or methyl;

$R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetanyl, tetrahydrofuranyl, or tetrahydropyranyl, or $R^{15}$ and $R^{16}$ together with the nitrogen atom to which they are attached form a substituted or unsubstituted 4- to 6-membered heteroalicyclic group selected from the following groups:

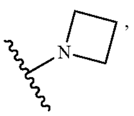

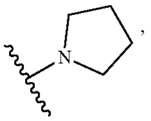

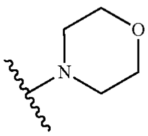

-continued

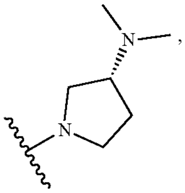
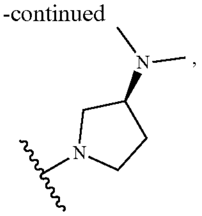
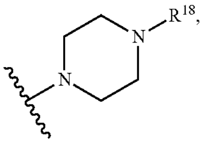
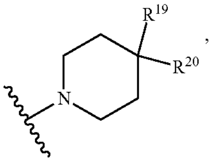
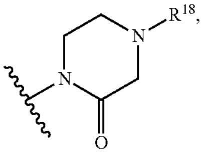
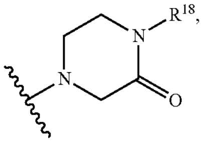
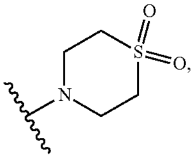

$R^{18}$ is selected from —H, methyl, ethyl, formyl, acetyl, hydroxyethyl, hydroxypropyl, fluoroethyl, fluoropropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, fluoro, formyl, acetyl, hydroxyethyl, hydroxypropyl, fluoroethyl, fluoropropyl, methoxyethyl, methoxypropyl, ethoxyethyl, ethoxypropyl, methylsulfonyl, ethylsulfonyl, amino, methylamino, dimethylamino, methoxy, or ethoxy.

5. The compound of formula (I) according to claim 4, or a stereoisomer, a tautomer, a hydrate, a solvate, or a pharmaceutically acceptable salt thereof, wherein $R^4$ is $-T_1-R_8$, $T_1$ is selected from:

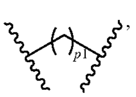
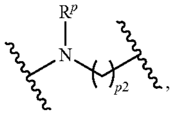

p1 is 0, and p2 is an integer of 2-3;

$R^p$ is selected from —H, methyl, or ethyl;

$R^8$ is selected from methylamino, ethylamino, propylamino, dimethylamino, diethylamino, N-methyl-N-ethylamino or the following groups:

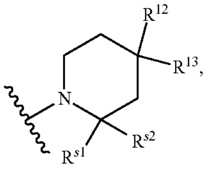
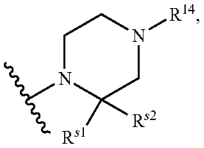

$R^{12}$ is —H, —F, methyl, or ethyl, $R^{13}$ is —H, or $—NR^{15}R^{16}$, $R^{14}$ is —H, methyl, ethyl, propyl, isopropyl, or

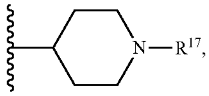

wherein $R^{17}$ is methyl, ethyl, propyl, or isopropyl, $R^{s1}$ and $R^{s2}$ are each independently selected from H or methyl;

$R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetan-3-yl, tetrahydrofuran-3-yl, or tetrahydro-2H-pyran-4-yl, or $R^{15}$ and $R^{16}$ together with the nitrogen atom to which they are attached form a substituted or unsubstituted 4- to 6-membered heteroalicyclic group selected from the following groups:

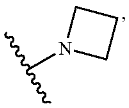
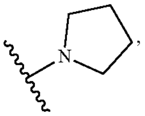
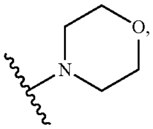
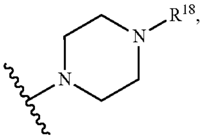
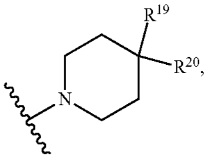
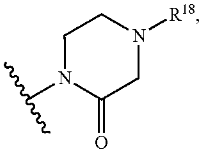
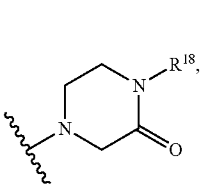
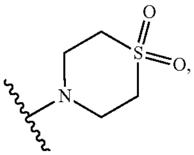

$R^{18}$ is selected from —H, methyl, ethyl, formyl, acetyl, hydroxyethyl, hydroxypropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, fluoro, hydroxyethyl, hydroxypropyl, fluoroethyl, fluoropropyl, methoxyethyl, methoxypropyl, ethoxyethyl, ethoxypropyl, methylsulfonyl, ethylsulfonyl, amino, methylamino, dimethylamino, methoxy, or ethoxy.

6. The compound of formula (I) according to claim 4, or a stereoisomer, a tautomer, a hydrate, a solvate, or a pharmaceutically acceptable salt thereof, wherein $R^4$ is

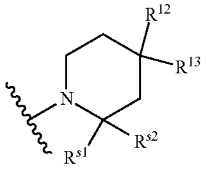

$R^{12}$ is —H, —F, methyl, or ethyl, $R^{13}$ is —H or —$NR^{15}R^{16}$, $R^{s1}$ and $R^{s2}$ are H, $R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetan-3-yl, tetrahydrofuran-3-yl, or tetrahydro-2H-pyran-4-yl, or $R^{15}$ and $R^{16}$ together with the nitrogen atom to which they are attached form a substituted or unsubstituted 4- to 6-membered heteroalicyclic group selected from the following groups:

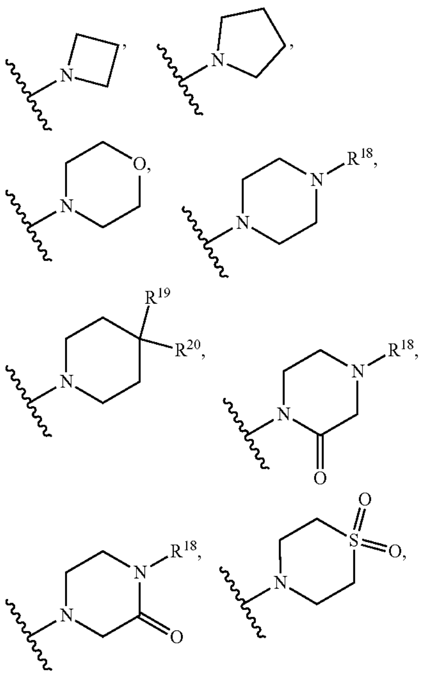

$R^{18}$ is selected from —H, methyl, ethyl, formyl, acetyl, hydroxyethyl, hydroxypropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, or fluoro.

7. The compound of formula (I) according to claim 1, or a stereoisomer, a tautomer, a hydrate, a solvate, or a pharmaceutically acceptable salt thereof, wherein X is N or CH;

L is —O—, —S—,

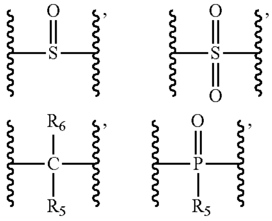

or —$NR_5$—, wherein $R_5$ and $R_6$ are each independently hydrogen, methyl, ethyl, propyl or isopropyl;

$R^1$ is

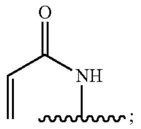

$R_2$ is —H, —F, —Cl, methyl, or methoxy;

$R_3$ is selected from —H, —F, —Cl, —Br, hydroxyl, carboxyl, cyano, methyl, ethyl, propyl, isopropyl, tert-butyl, methoxy, ethoxy, propoxy, isopropoxy, cyclopropyloxy, cyclobutyloxy, methylthio, ethylthio, propylthio, isopropylthio, fluoromethyl, difluoromethyl, trifluoromethyl, fluoromethoxy, difluoromethoxy, trifluoromethoxy, ethynyl, ethenyl, cyclopropyl, cyclobutyl, cyclopropylmethyl, cyclobutylmethyl, amino, methylamino, ethylamino, dimethylamino, diethylamino, N-methyl-N-ethylamino, or the following groups:

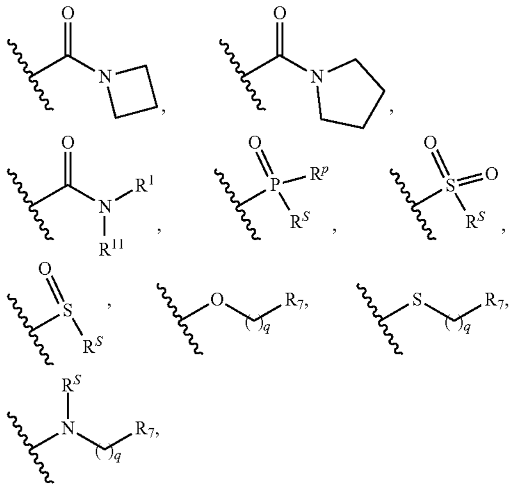

q is an integer of 2-3, $R^s$ is selected from —H, methyl, or ethyl, and $R^p$ is selected from —H, methyl, or ethyl, R' and R" are each independently selected from —H, methyl, ethyl, propyl, isopropyl, cyclopropyl, or cyclobutyl, $R_7$ is selected from —H, —F, hydroxyl, cyano, carboxyl, amino, methyl, ethyl, propyl, isopropyl, methoxy, ethoxy, propoxy, isopropoxy, methylamino, ethylamino, or dimethylamino;

$R^4$ is $-T_1-R_8$, $T_1$ is selected from:

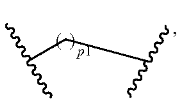,
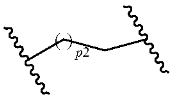,
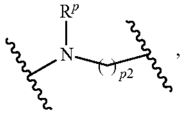, p1 is an integer of 0-3, and p2 is an integer of 2-3;

$R^p$ is selected from —H, methyl, or ethyl;

$R^8$ is selected from —H, —F, —Cl, hydroxyl, amino, cyano, fluoromethoxy, difluoromethoxy, trifluoromethoxy, methyl, ethyl, propyl, butyl, hexyl, isopropyl, fluoromethyl, difluoromethyl, trifluoromethyl, cyclopropyl, cyclobutyl, cyclopentyl, cyclohexyl, methoxy, ethoxy, propoxy, butoxy, isopropoxy, methylthio, ethylthio, propylthio, isopropylthio, methylamino, ethylamino, propylamino, dimethylamino, diethylamino, N-methyl-N-ethylamino or the following groups:

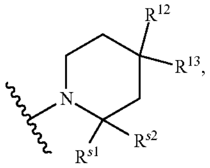
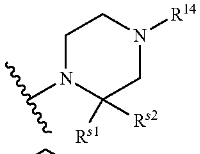,
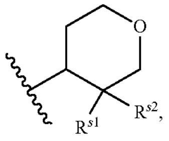
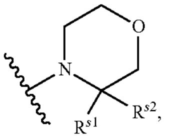
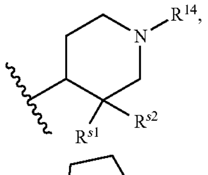
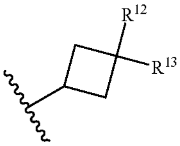,
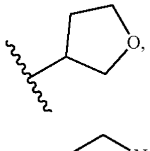
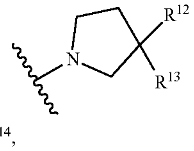,
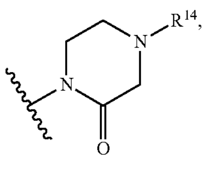

$R^{12}$ is —H, —F, methyl, or ethyl, $R^{13}$ is —H, —F, hydroxyl, hydroxymethyl, cyano, methyl, ethyl, methoxy, or $—NR^5R^{16}$, $R^{14}$ is —H, —F, methyl, ethyl, propyl, isopropyl, or

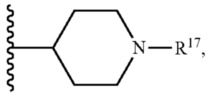

wherein $R^{17}$ is —H, —F, methyl, ethyl, propyl, or isopropyl, $R^{s1}$ and $R^{s2}$ are each independently selected from —H or methyl;

$R^{15}$ and $R^{16}$ are each independently —H, methyl, ethyl, propyl, isopropyl, hydroxyethyl, hydroxypropyl, cyanomethyl, cyanoethyl, methoxyethyl, methoxypropyl, ethoxyethyl, ethoxypropyl, isopropoxyethyl, isopropoxypropyl, cyclopropyl, cyclobutyl, dimethylaminoethyl, dimethylaminopropyl, diethylaminoethyl, diethylaminopropyl, methylethylaminoethyl, methylethylaminopropyl, fluoroethyl, fluoropropyl, methylthioethyl, methylthiopropyl, ethylthioethyl, ethylthiopropyl, isopropylthioethyl, isopropylthiopropyl, methylsulfonylethyl, methylsulfonylpropyl, ethylsulfonylethyl, ethylsulfonylpropyl, 2-hydroxy-2-methylpropyl, 3-hydroxy-3-methylbutyl, oxetanyl, tetrahydrofuranyl, or tetrahydropyranyl, or $R^{15}$ and $R^{16}$ together with the nitrogen atom to which they are attached form a substituted or unsubstituted 4- to 6-membered heteroalicyclic group selected from the following groups:

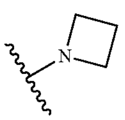,
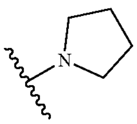,
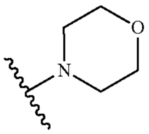,
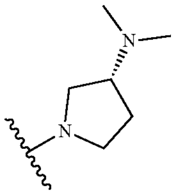,
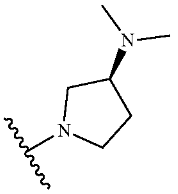,
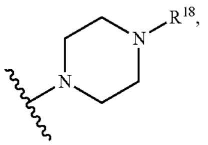
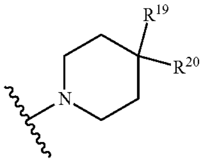,
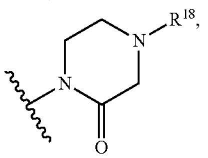
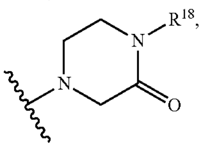
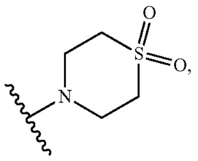

$R^{18}$ is selected from —H, methyl, ethyl, formyl, acetyl, hydroxyethyl, hydroxypropyl, fluoroethyl, fluoropropyl, methoxyethyl, methoxypropyl, ethoxyethyl, ethoxypropyl, methylsulfonyl, or ethylsulfonyl, $R^{19}$ and $R^{20}$ are each independently selected from —H, methyl, ethyl, hydroxyl, cyano, fluoro, formyl, acetyl, hydroxyethyl, hydroxypropyl, fluoroethyl, fluoropropyl, methoxyethyl, methoxypropyl, ethoxyethyl, ethoxypropyl, methylsulfonyl, ethylsulfonyl, amino, methylamino, dimethylamino, methoxy, or ethoxy, and, when $R_4$ is 4-ethyl-piperazin-1-yl, and L is —O— or

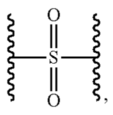

$R_2$ and $R_3$ are not both hydrogen.

8. The compound of formula (I) according to claim 7, or a stereoisomer, a tautomer, a hydrate, a solvate, or a pharmaceutically acceptable salt thereof, wherein L is —O—, and, when $R_4$ is 4-ethyl-piperazin-1-yl, $R_2$ and $R_3$ are not both hydrogen.

9. The compound of formula (I) according to claim 1, or a stereoisomer, a tautomer, a hydrate, a solvate, or a pharmaceutically acceptable salt thereof, wherein X is N;

L is —O—;

$R_1$ is

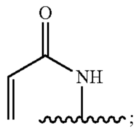 [SMILES: *NC(=O)C=C]

$R_2$ is hydrogen, or $C_1$-$C_3$ alkoxy;

$R_3$ is selected from hydrogen, or halogen;

$R_4$ is -$T_1$-$R_8$;

$T_1$ is:

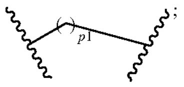

p1 is 0;

$R_8$ is a 4- to 6-membered heteroalicyclic group, wherein the 4- to 6-membered heteroalicyclic group is unsubstituted or substituted with —$NR^{10}$ $R^{11}$;

$R^{10}$ and $R^{11}$ are each independently selected from —H, $C_1$-$C_6$ alkyl, or hydroxyl-substituted $C_2$-$C_6$ alkyl, or $R^{10}$ and $R^{11}$ together with the nitrogen atom to which they are attached form a 4- to 6-membered heteroalicyclic group, wherein the 4- to 6-membered heteroalicyclic group is unsubstituted or substituted with $C_1$-$C_3$ alkyl.

10. The compound of formula (I) according to claim 9, or a stereoisomer, a tautomer, a hydrate, a solvate, or a pharmaceutically acceptable salt thereof, wherein $R^4$ is

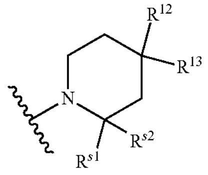

$R^{12}$ is —H, $R^{13}$ is —$NR^{15}R^{16}$, $R^{s1}$ and $R^{s2}$ are H, $R^{15}$ and $R^{16}$ are each independently —H, methyl, ethyl, propyl, isopropyl, hydroxyethyl, hydroxypropyl, 2-hydroxy-2-methylpropyl, or 3-hydroxy-3-methylbutyl, or $R^{15}$ and $R^{16}$ together with the nitrogen atom to which they are attached form a substituted or unsubstituted 4- to 6-membered heteroalicyclic group selected from the following group:

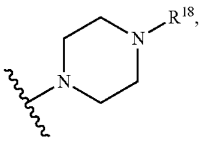

$R^{18}$ is selected from —H, methyl, or ethyl.

11. The compound of formula (I) according to claim 1, or a pharmaceutically acceptable salt thereof, wherein the compound has the following structure:

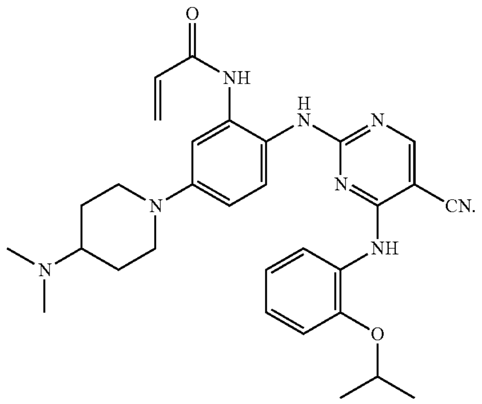

12. The compound of formula (I) according to claim 1, or a pharmaceutically acceptable salt thereof, wherein the compound has the following structure:
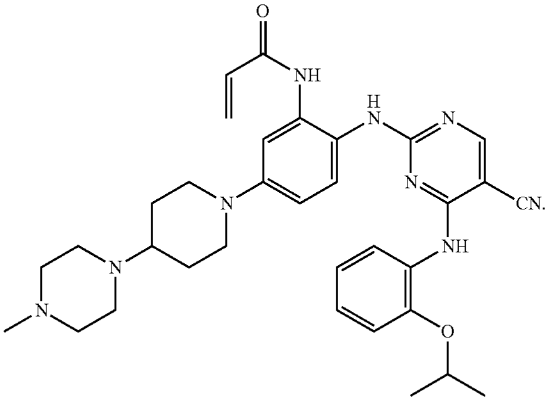
13. A compound or a stereoisomer, a tautomer, a hydrate, a solvate, or a pharmaceutically acceptable salt thereof, wherein the compound is selected from:
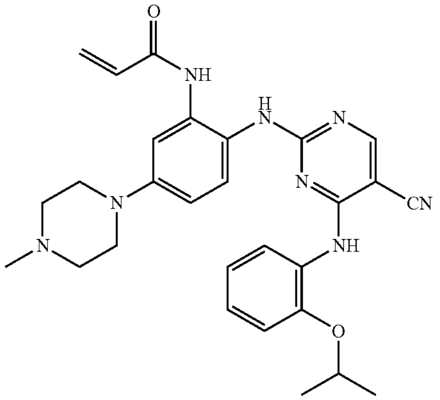
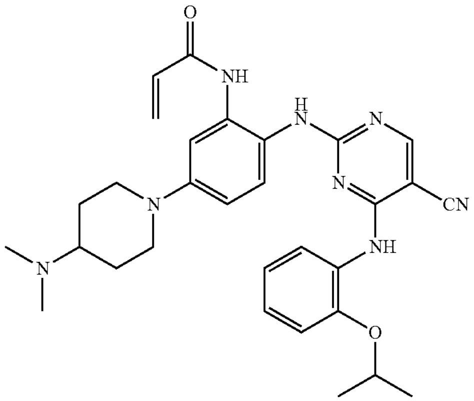
-continued
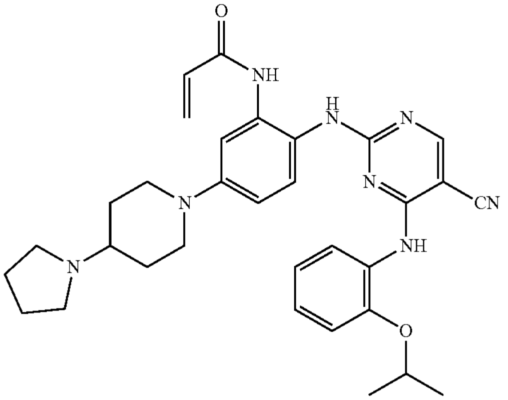
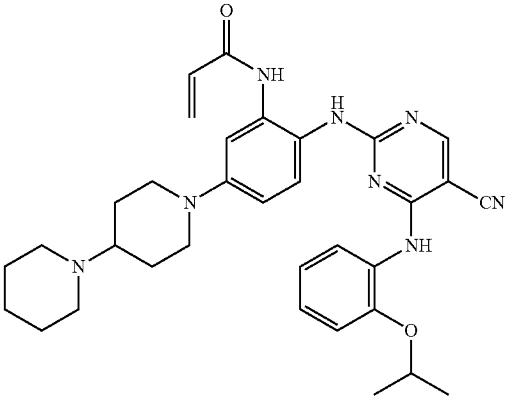
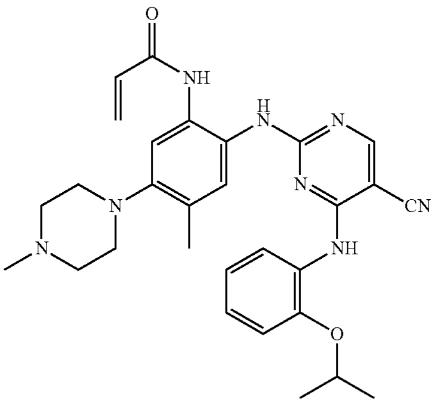
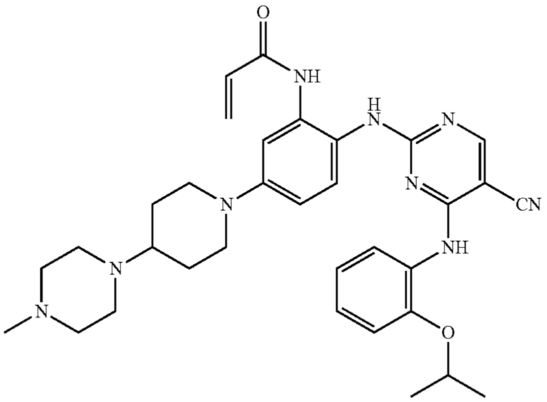

-continued
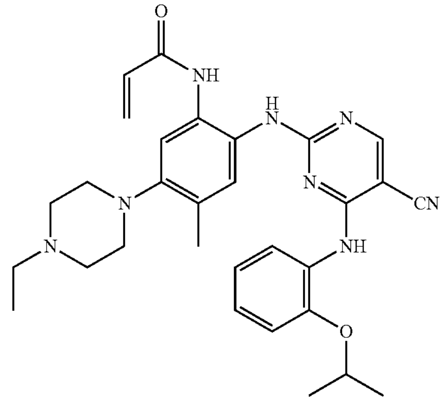
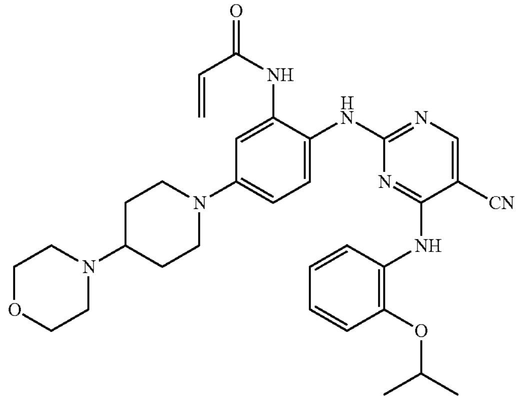
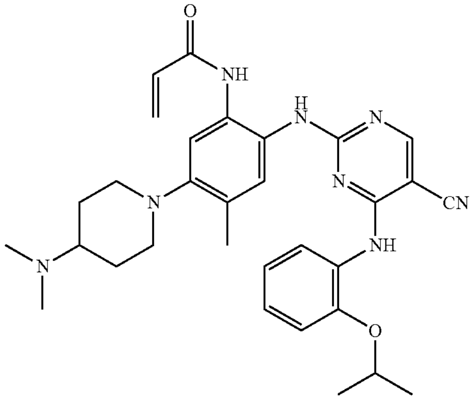
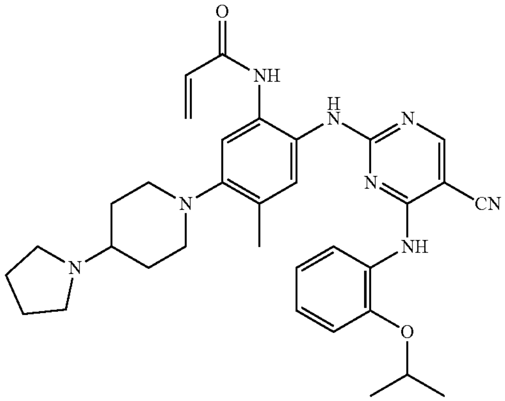
-continued
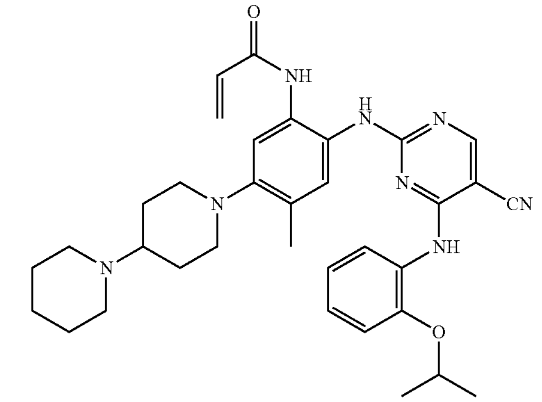
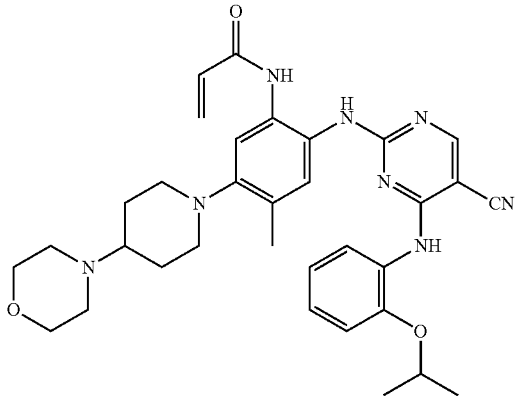
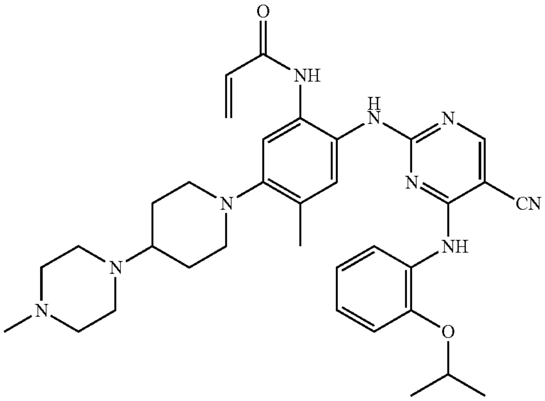
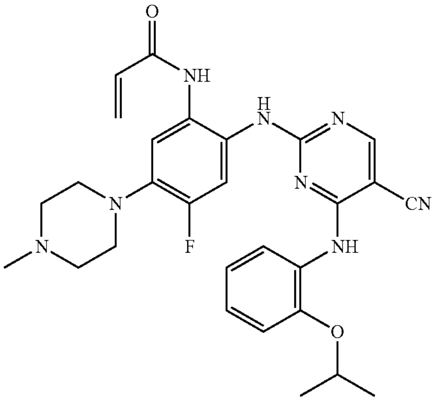

-continued
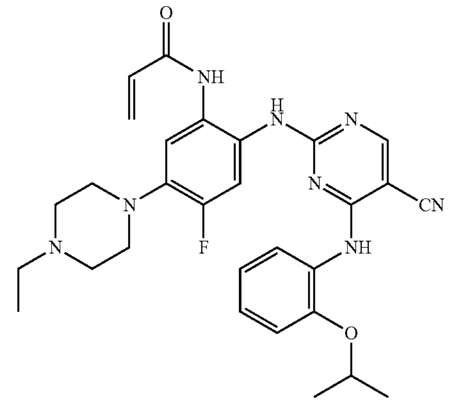
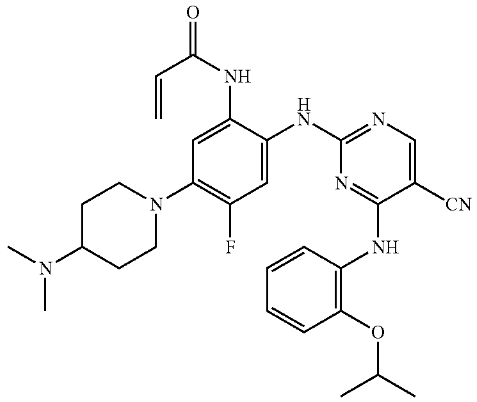
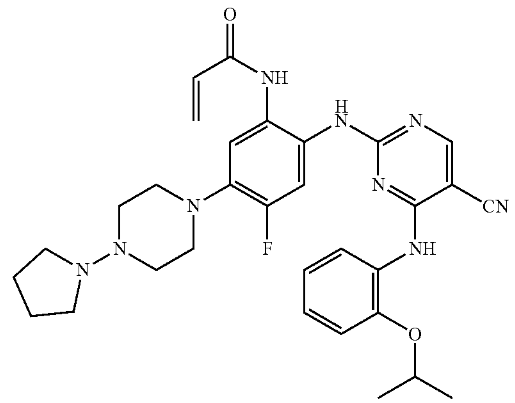
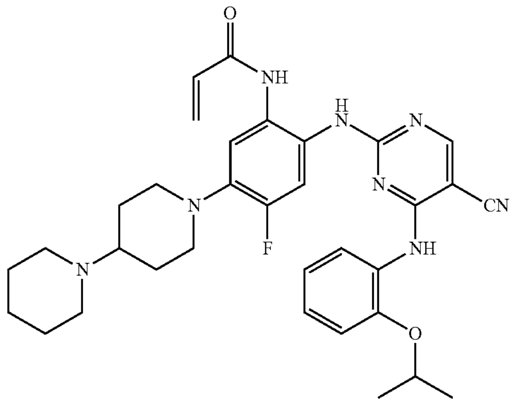
-continued
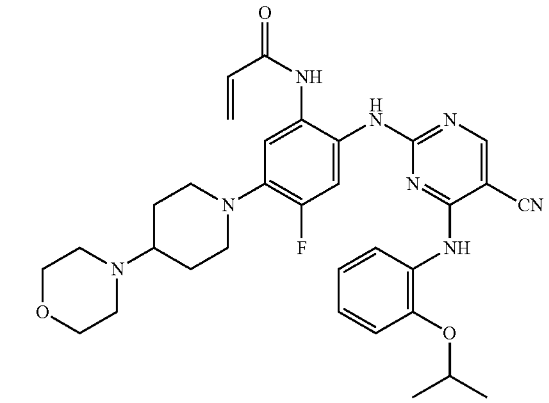
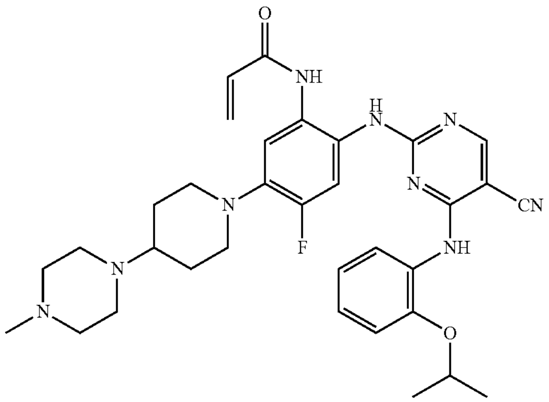
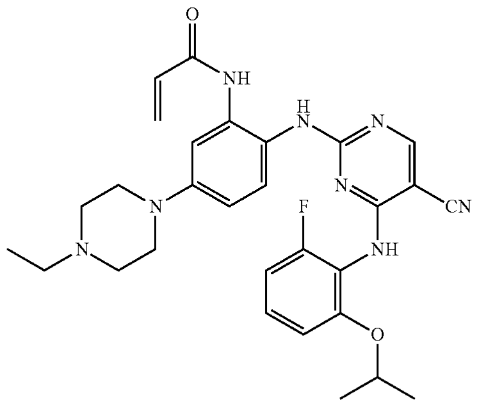
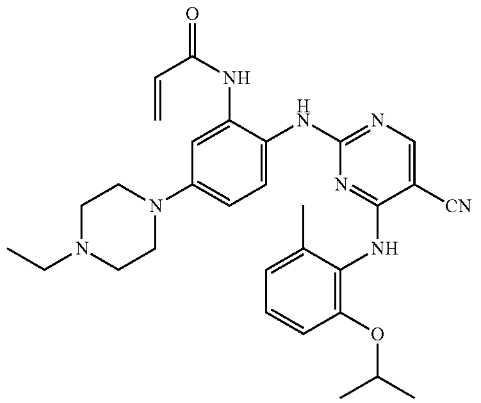

-continued
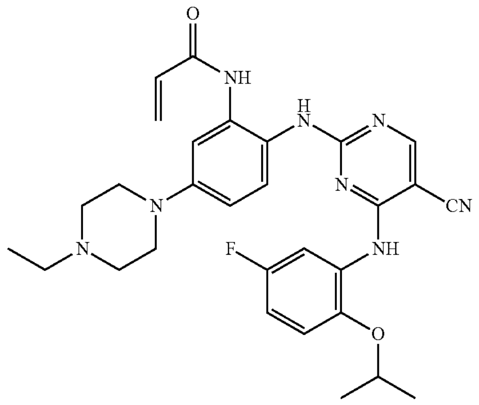
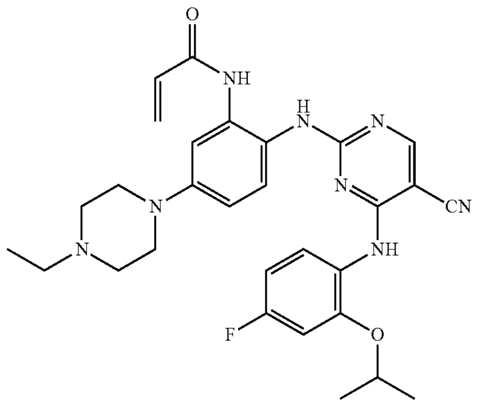
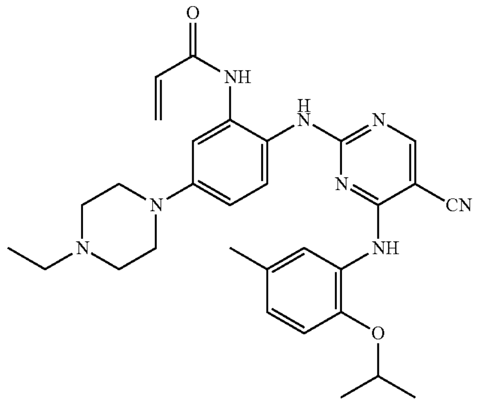
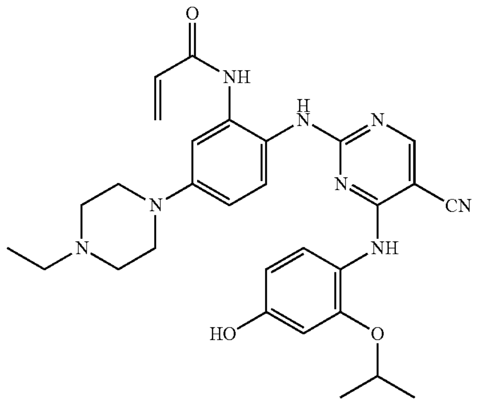
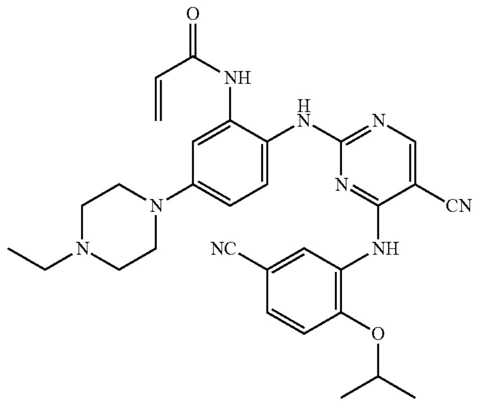
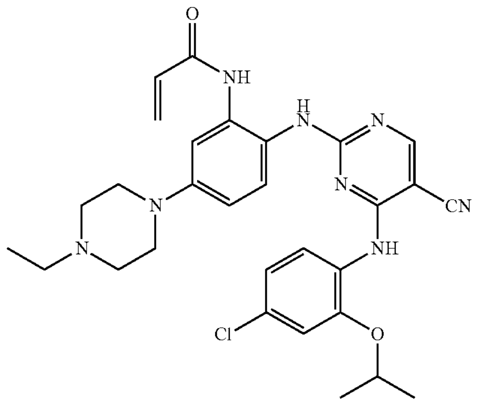
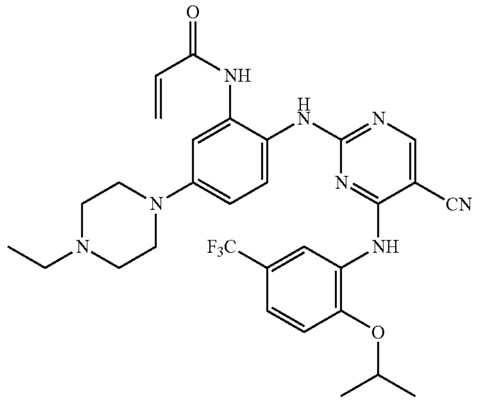
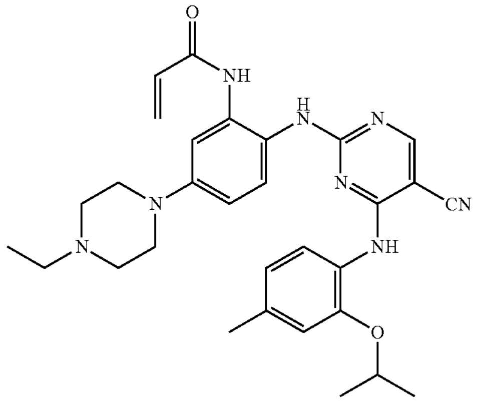
-continued -continued
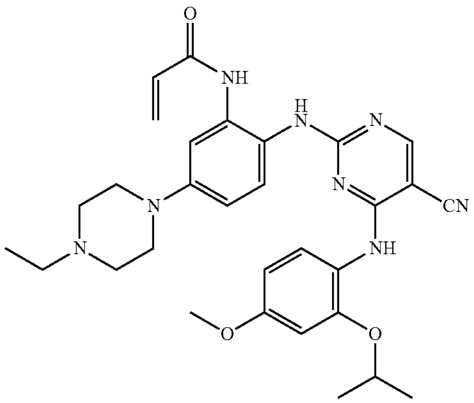
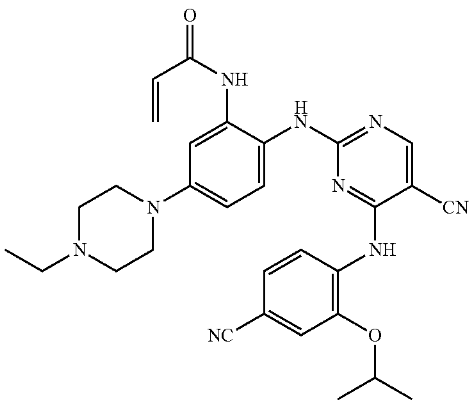
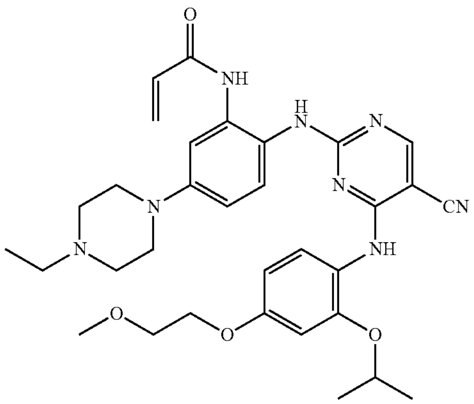
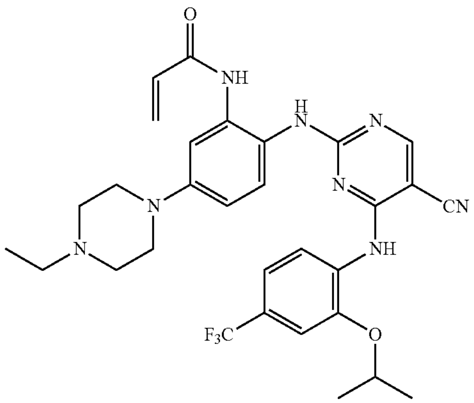
-continued
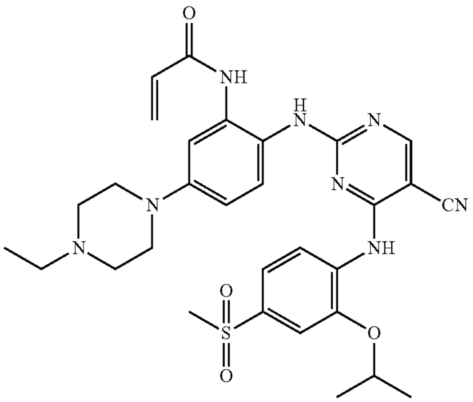
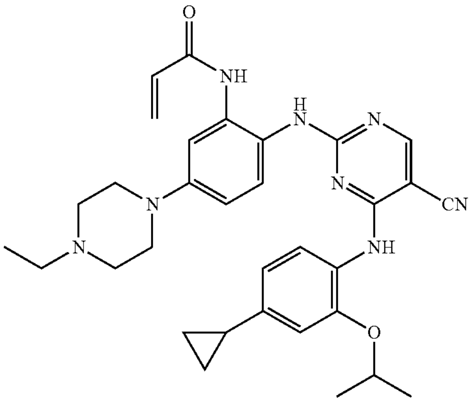
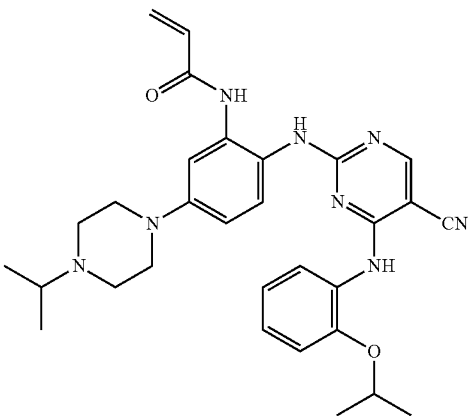
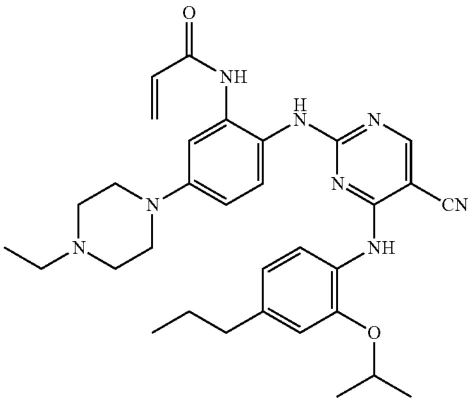

-continued
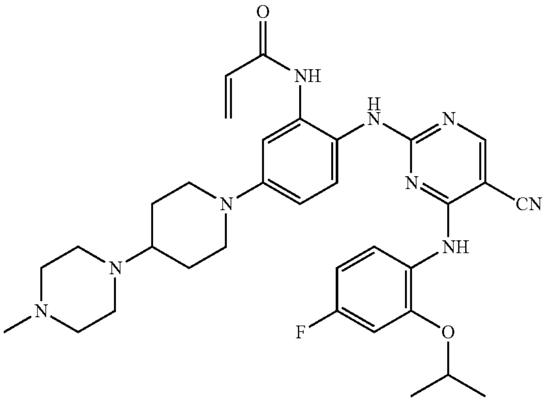
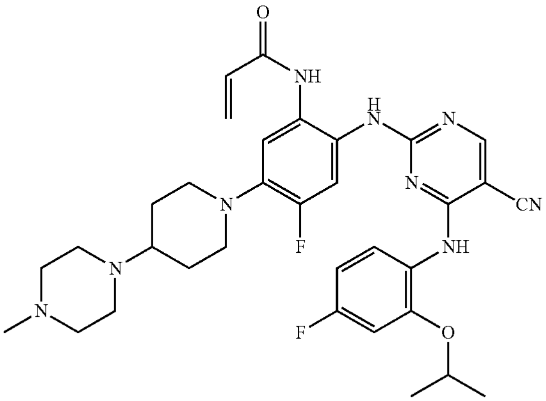
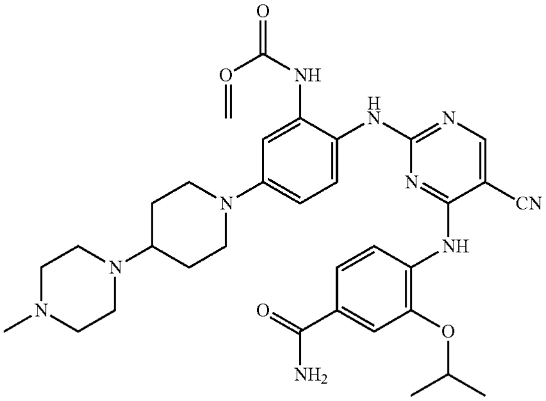
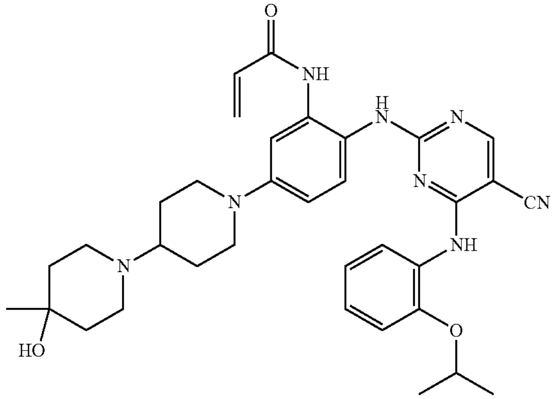
-continued
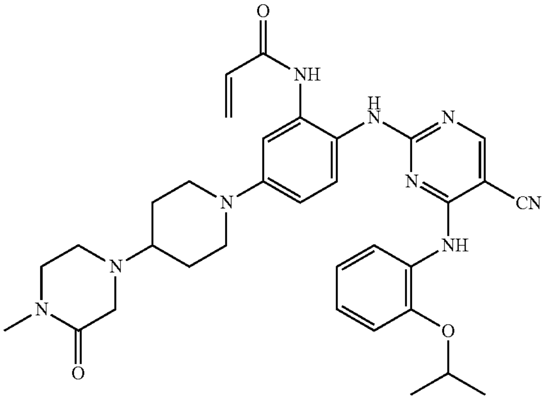
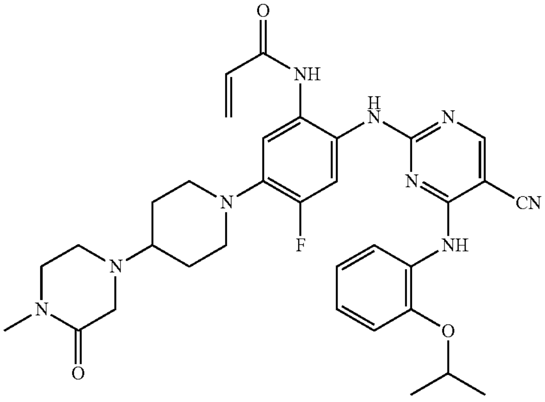
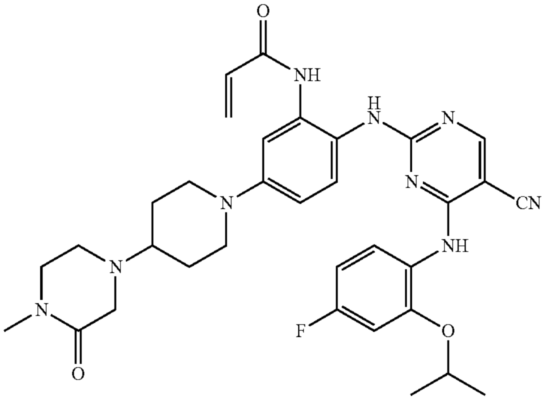
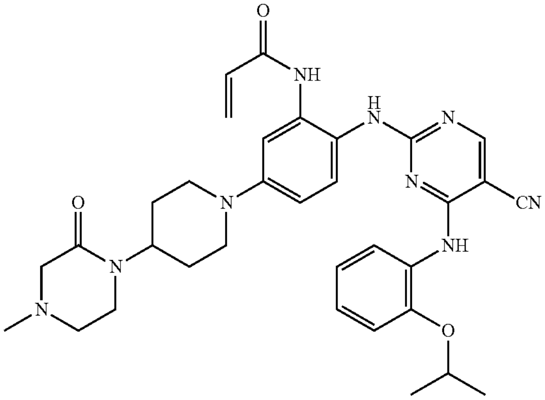

-continued
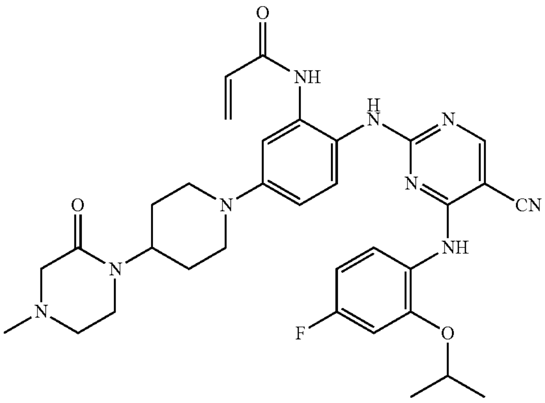
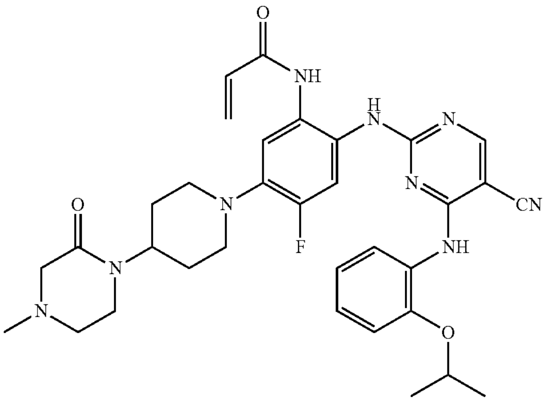
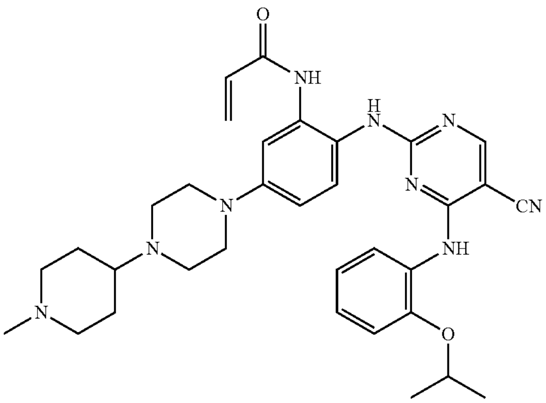
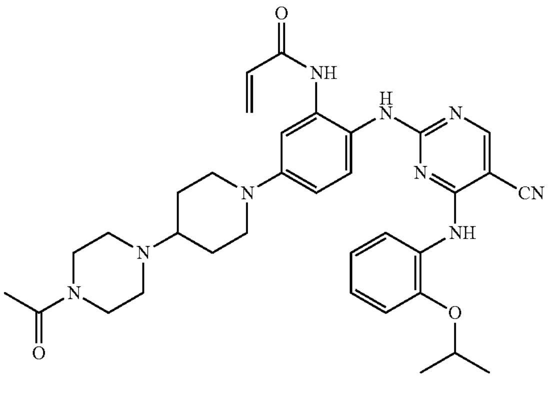
-continued
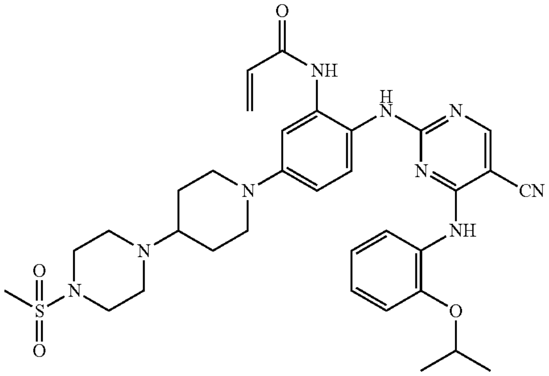
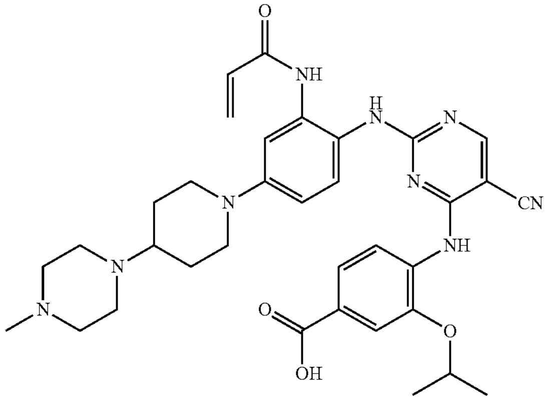
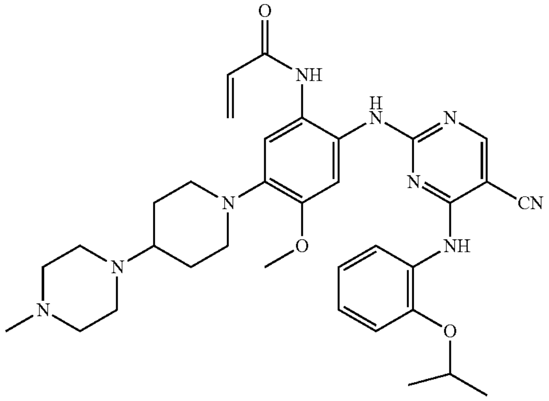
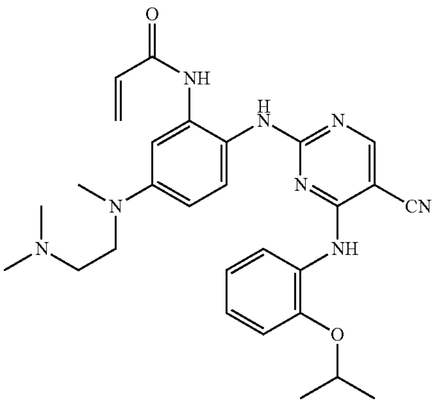

-continued
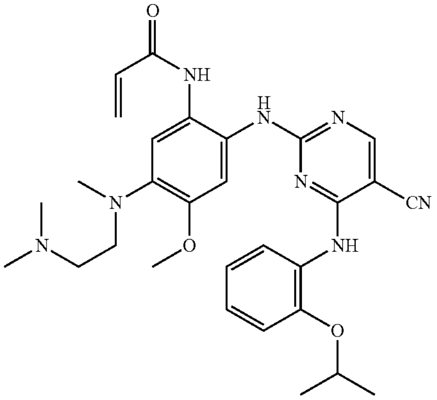
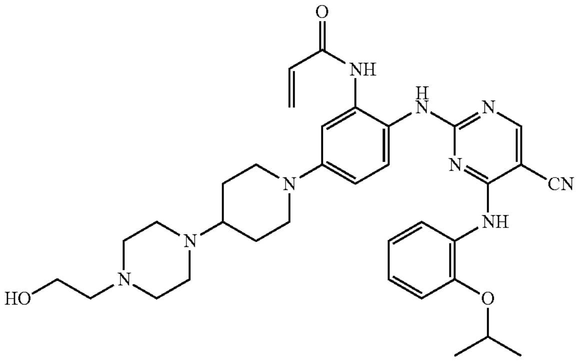
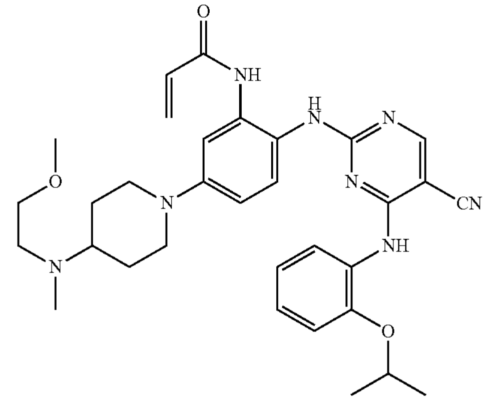
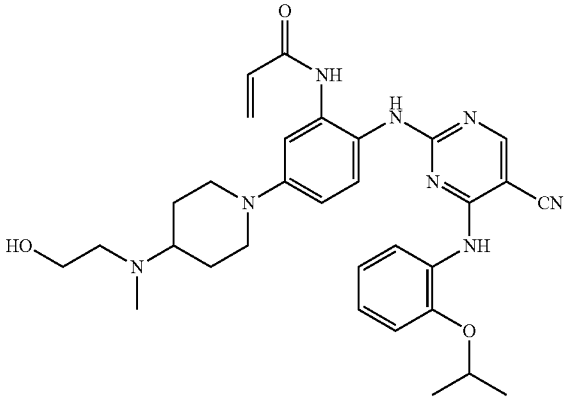
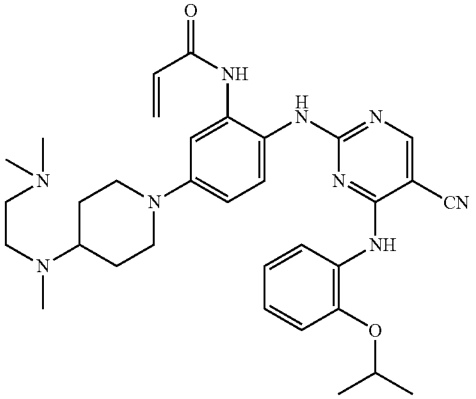
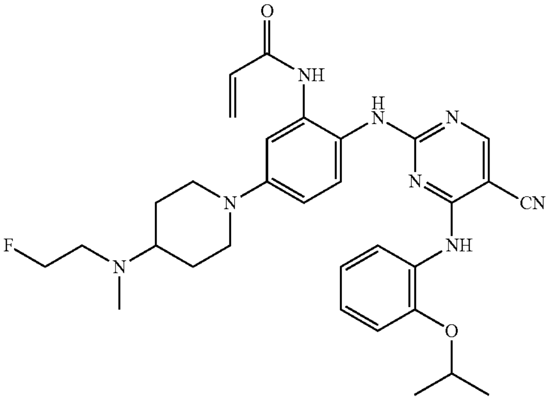
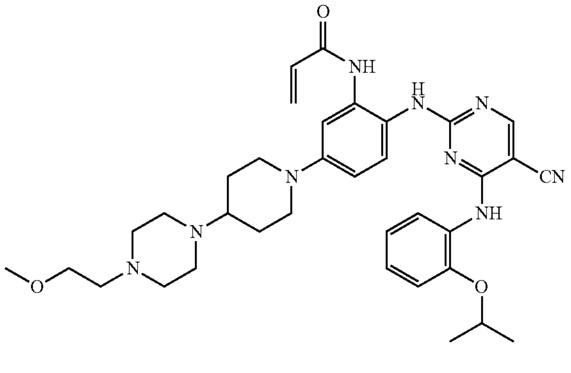
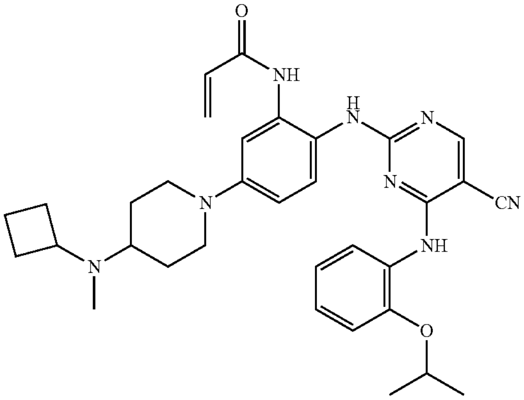
-continued -continued
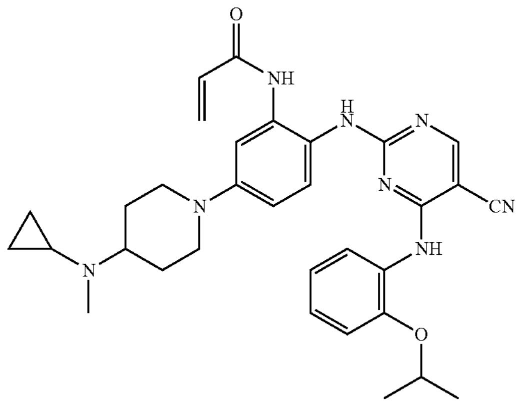
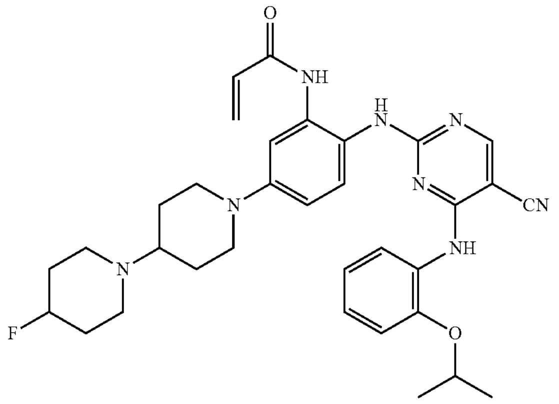
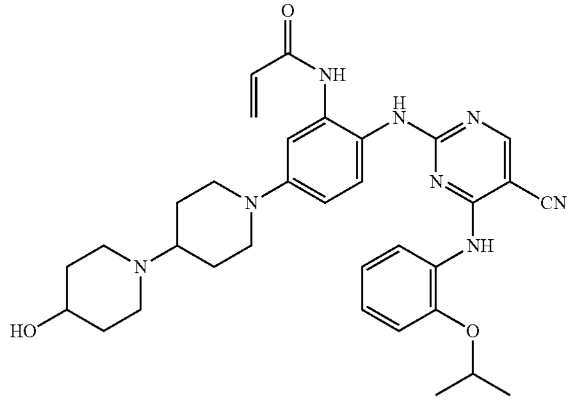
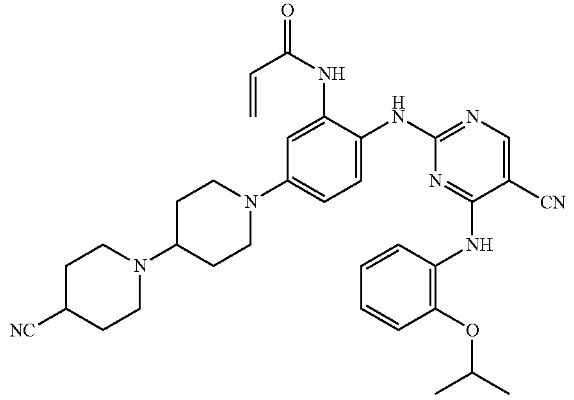
-continued
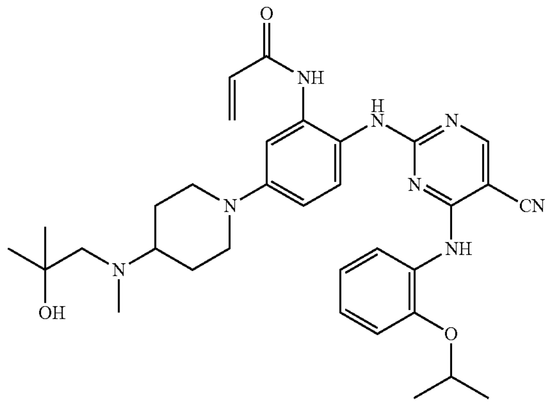
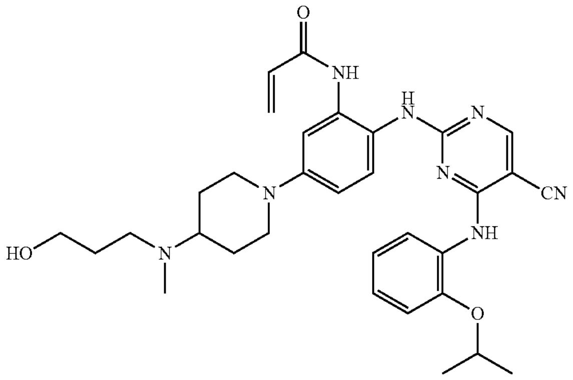
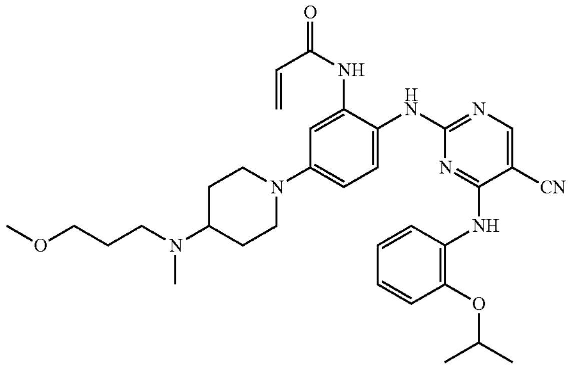
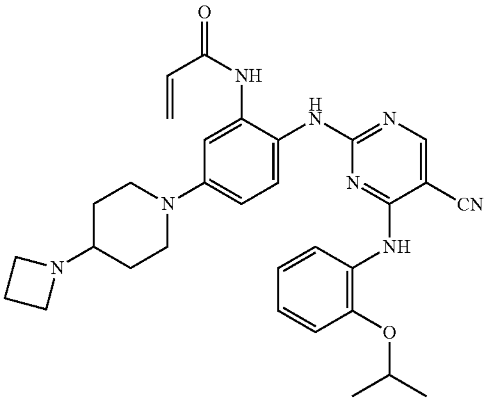

-continued
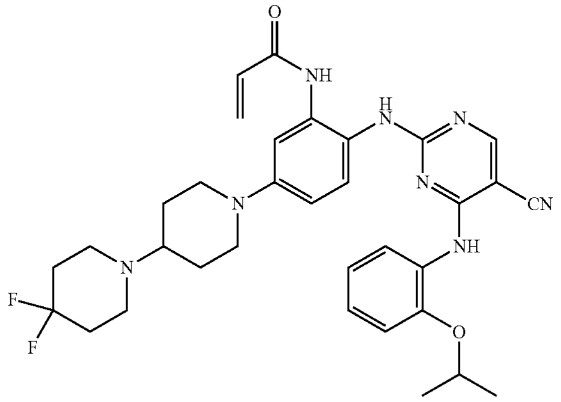
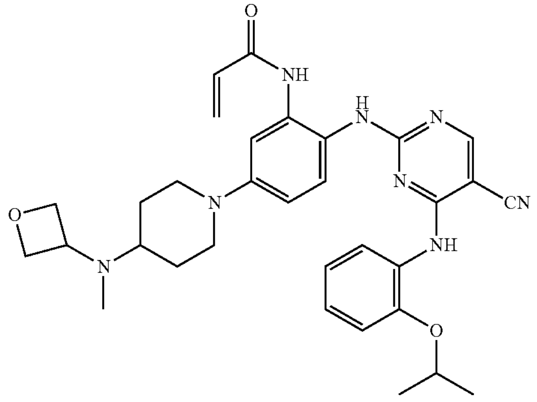
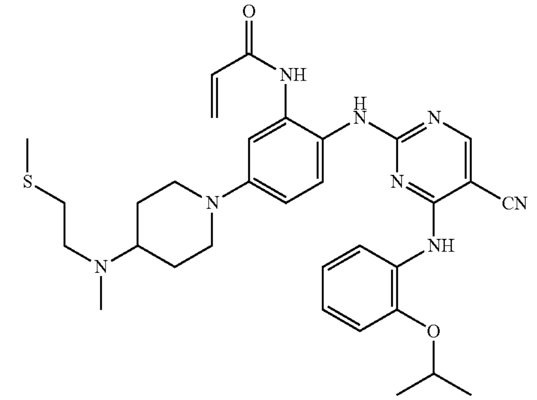
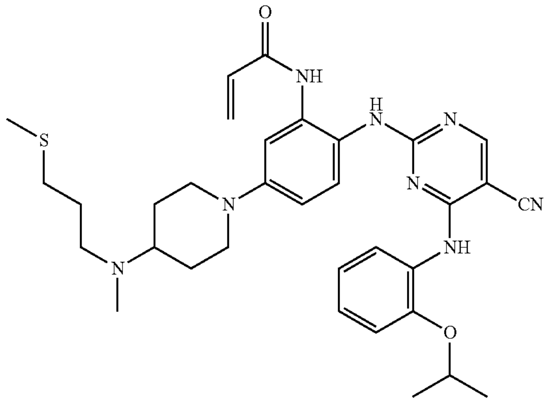
-continued
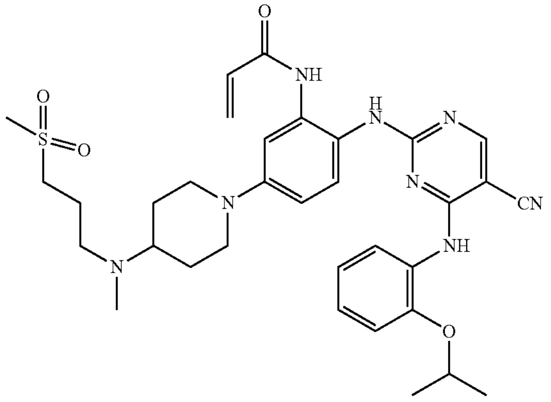
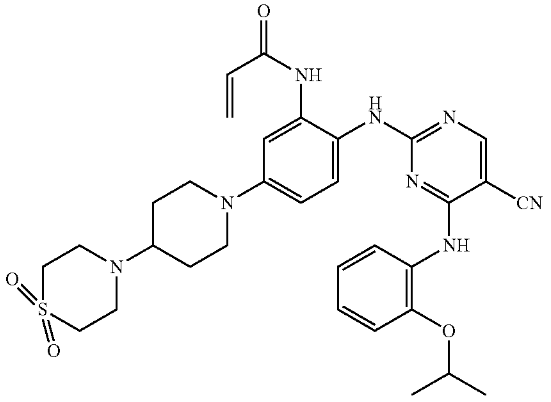
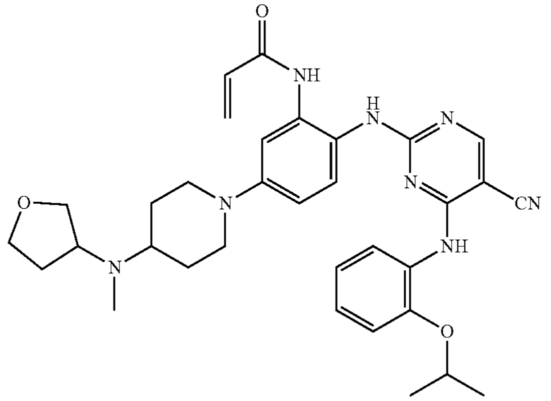
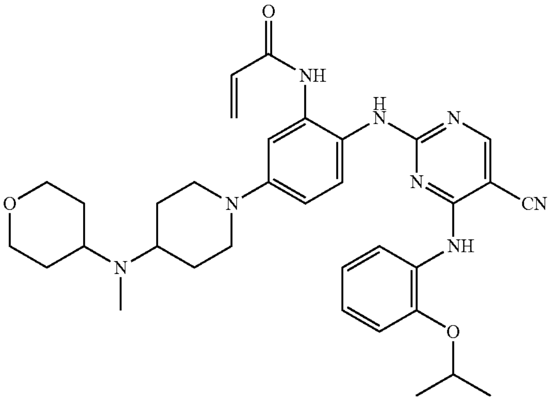

-continued
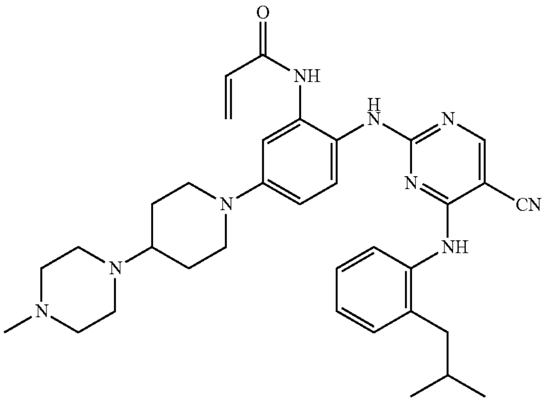
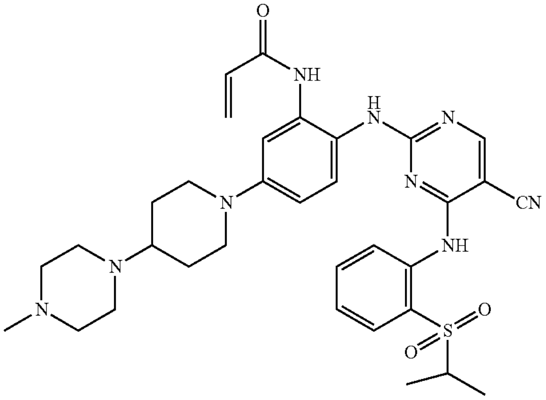
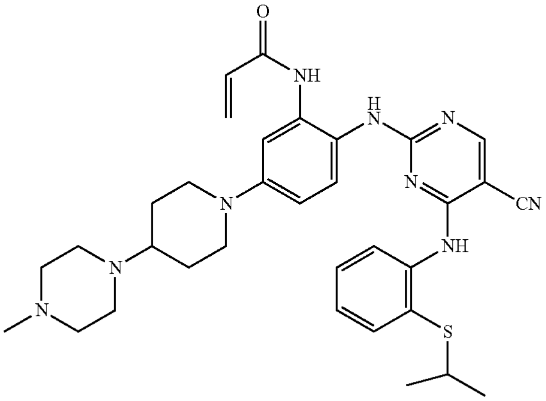
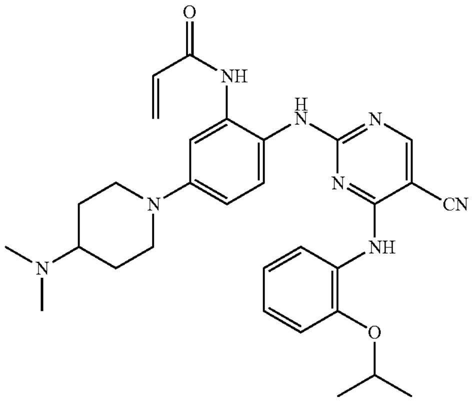
-continued
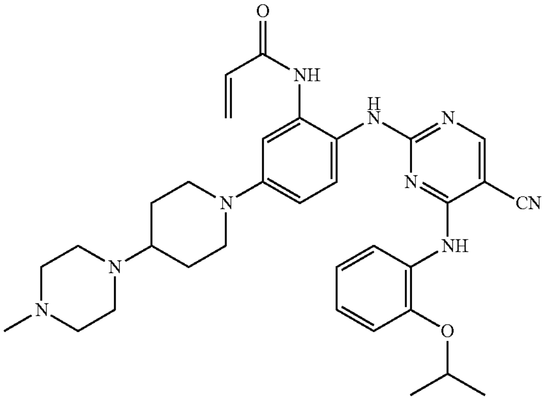
and
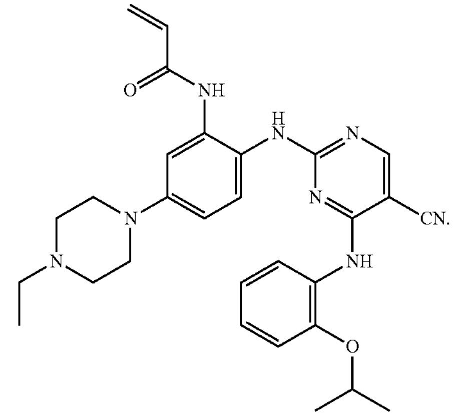
14. The compound of formula (I) according to claim 1, or a pharmaceutically acceptable salt thereof, wherein the compound has the following structure:
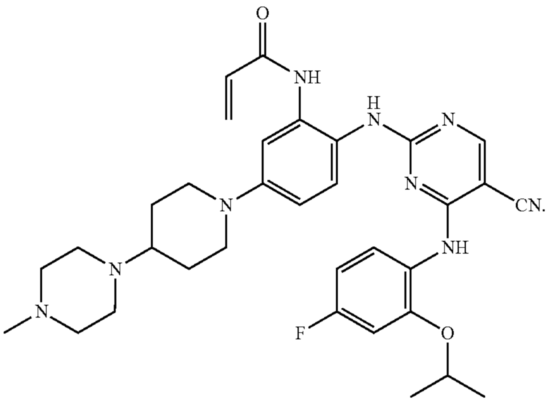
15. The compound of formula (I) according to claim 1, or a pharmaceutically acceptable salt thereof, wherein the compound has the following structure:

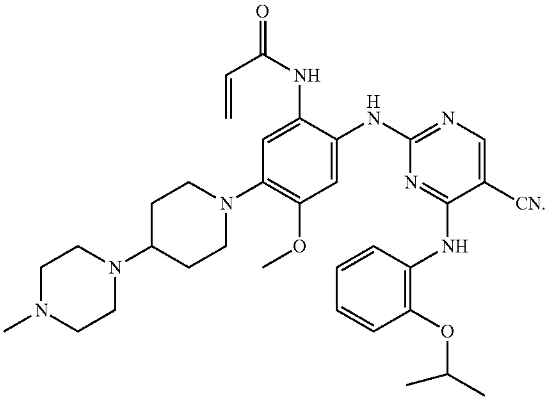

16. The compound of formula (I) according to claim 1, or a pharmaceutically acceptable salt thereof, wherein the compound has the following structure:

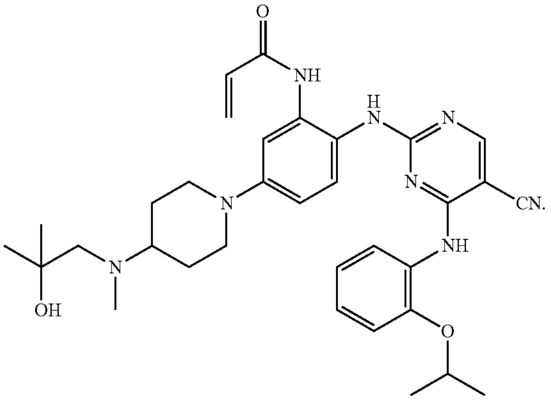

17. A pharmaceutical composition, comprising the compound according to claim 1, or a pharmaceutically acceptable salt, a hydrate, or a solvate thereof, and a pharmaceutically acceptable carrier or excipient.

18. The pharmaceutical composition according to claim 17, wherein the pharmaceutical composition further comprises one or more other therapeutic agents.

19. A method of treating a disease related to tyrosine kinase FGFR4 in a subject in need thereof, comprising administering to the subject the compound according to claim 1, or a pharmaceutically acceptable salt, a hydrate, or a solvate thereof.

20. The method according to claim 19, wherein the diseases related to tyrosine kinase FGFR4 include fundus oculi disease, xerophthalmia, psoriasis, vitiligo, dermatitis, alopecia areata, rheumatoid arthritis, colitis, multiple sclerosis, systemic lupus erythematosus, Crohn's disease, atherosclerosis, pulmonary fibrosis, liver fibrosis, bone marrow fibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myelocytic leukemia, non-Hodgkin's lymphoma, nasopharyngeal cancer, esophageal cancer, brain tumor, B-cell and T-cell lymphoma, lymphoma, multiple myeloma, biliary tract cancerous sarcoma, and cholangiocarcinoma.

* * * * *